United States Patent
Fleishman et al.

(10) Patent No.: US 10,665,324 B2
(45) Date of Patent: May 26, 2020

(54) METHOD OF COMPUTATIONAL PROTEIN DESIGN

(71) Applicant: Yeda Research and Development Co. Ltd., Rehovot (IL)

(72) Inventors: Sarel Fleishman, Rehovot (IL); Gideon Lapidoth, Rehovot (IL); Maria Gabriele Pszolla, Rehovot (IL); Christoffer Norn, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 567 days.

(21) Appl. No.: 15/323,994

(22) PCT Filed: Jul. 6, 2015

(86) PCT No.: PCT/IL2015/050696
§ 371 (c)(1),
(2) Date: Jan. 5, 2017

(87) PCT Pub. No.: WO2016/005969
PCT Pub. Date: Jan. 14, 2016

(65) Prior Publication Data
US 2017/0206308 A1    Jul. 20, 2017

Related U.S. Application Data

(60) Provisional application No. 62/021,309, filed on Jul. 7, 2014.

(51) Int. Cl.
| | | |
|---|---|---|
| *G16B 15/00* | (2019.01) | |
| *G16B 20/00* | (2019.01) | |
| *G16B 35/00* | (2019.01) | |
| *G16C 20/60* | (2019.01) | |

(52) U.S. Cl.
CPC ............ *G16B 15/00* (2019.02); *G16B 20/00* (2019.02); *G16B 35/00* (2019.02); *G16C 20/60* (2019.02)

(58) Field of Classification Search
None
See application file for complete search history.

(56) References Cited

FOREIGN PATENT DOCUMENTS

| | | |
|---|---|---|
| CN | 1672160 | 9/2005 |
| JP | 2005-526518 | 9/2005 |
| WO | WO 03/099999 | 12/2003 |
| WO | WO 2016/005969 | 1/2016 |

OTHER PUBLICATIONS

International Search Report and the Written Opinion dated Nov. 5, 2015 From the International Searching Authority Re. Application No. PCT/2015/050696.

Andreeva et al. "SCOP2 Prototype: A New Approach to Protein Structure Mining", Nucleic Acids, 42: D310-D314, Published Online Nov. 29, 2013.

Baudry et al. "Structure-Based Design and in Silico Virtual Screening of Combinatorial Libraries. A Combined Chemical-Computational Project", Journal of Chemical Education, XP055214987, 82(6): 890-894, Jun. 1, 2005.

Densmore et al. "Bio-Design Automation: Software + Biology + Robots", Trends in Biotechnology, 32(3): 111-113, Mar. 2014.

Khoury et al. "Protein Folding and De Novo Protein Design for Biotechnological Applications", Trends in Biotechnology, 32(2): 99-109, Feb. 2014.

Kiyoshi et al. Affinity Improvement of a Therapeutic Antibody by Structure-Based Computational Design: Generation of Electrostatic Interactions in the Transition State Stabilizes the Antibody-Antigen Complex, PIOS ONE, XP055213871, 9(1): e87099-1-e87099-10, Jan. 27, 2014. Abstract, p. 2.

Norel et al. "Examination of Shape Complementarity in Docking of Unbound Proteins", Computer Science Department, School of Mathematical Sciences, Tel Aviv University, Israel ff., p. 1-20, Jan. 19, 1999.

Pantazes et al. "MAPs: A Database of Modular Antibody Parts for Predicting Tertiary Structures and Designing Affinity Matured Antibodies", BMC Bioinformatics, XP055213874, 14(168): 1-13, 2013.

Pantazes et al. "OptCDR: A General Computational Method for the Design of Antibody Complementarity Determining Regions for Targeted Epitope Binding", Protein Engineering, Design & Selection, 23(11): 849-858, Sep. 16, 2010.

Shirai et al. "High-Resolution Modeling of Antibody Structures by a Combination of Bioinformatics, Expert Knowledge, and Molecular Simulations", Proteins: Structure, Function, and Bioinformatics, p. 1-12, 2014.

Smadbeck et al. "Protein Wisdom: A Workbench for in Silico De Novo Design of BioMolecules", Journal of Visualized Experiments, 77: e50476-1-e50476-26, Jul. 2013.

Weitzner et al. "Blind Prediction Performance of RosettaAntibody 3.0: Grafting, Relaxation, Kinematic Loop Modeling, and Full CDR Optimization", Proteins: Structure, Function, and Bioinformatics, p. 1-13, 2014.

Summons to Attend Oral Proceedings Pursuant to Rule 115(1) EPC and Communication From the Examining Division Dated May 8, 2019 From the European Patent Office Re. Application No. 15748315. 7. (13 Pages).

International Preliminary Report on Patentability dated Jan. 19, 2017 From the International Bureau of WIPO Re. Application No. PCT/2015/050696. (11 Pages).

(Continued)

*Primary Examiner* — Michael L Borin

(57) ABSTRACT

A method for constructing a library of amino-acid sequences having a common structural fold, and a method for designing and selecting an amino-acid sequence having a desired affinity to a molecular surface of interest of a molecular entity, using the library, are provided herein. The methods are based on a stochastic sampling of backbone conformations and amino acid conservation patterns observed in experimentally available protein structures having the common structural fold.

8 Claims, 9 Drawing Sheets
Specification includes a Sequence Listing.

(56) References Cited

OTHER PUBLICATIONS

Notification of Office Action and Search Report dated Aug. 28, 2018 From the National Intellectual Property Administration of the People's Republic of China Re. Application No. 201580047701.3 and Its Translation Into English. (14 Pages).
Barderas et al. "Affinity Maturation of Antibodies Assisted by in Silico Modeling", Proc. Natl. Acad. Sci. USA, PNAS, 105(26): 9029-9034, Jul. 1, 2008.
Campeotto et al. "One-Step Design of a Stable Variant of the Malaria Invasion Protein RH5 for Use as a Vaccine Immunogen", Proc. Natl. Acad. sci. USA, PNAS, 114(5): 998-1002, Jan. 31, 2017.
Clark et al. "Affinity Enhancement of an In Vivo Matured Therapeutic Antibody Using Structure-Based Computational Design", Protein Science, 15(5): 949-960, May 2006.
Clark et al. "An Antibody Loop Replacement Design Feasibility Study and a Loop-Swapped Dimer Structure", Protein Engineering, Design & Selection, 22(2): 93-101, Published Online Dec. 10, 2008.
Farady et al. "Improving the Species Cross-Reactivity of an Antibody Using Computational Design", Bioorganic and Medicinal Chemistry Letters, 19(14): 3744-3747, Jul. 15, 2009.
Figueroa et al. "Octarellin VI: Using Rosetta to Design a Putative Artificial (Beta/Alpha)8 Protein", PLoS ONE, 8(8): e71858-1-e71858-17, Aug. 19, 2013.
Fleishman et al. "Role of the Biomolecular Energy Gap in Protein Design, Structure, and Evolution", Cell, 149(2): 262-273, Apr. 13, 2012.
Goldenzweig et al. "Automated Structure- and Sequence-Based Design of Proteins for High Bacterial Expression and Stability", Molecular Cell, 63(2): 337-346, Jul. 21, 2016.
Gonzalo Parra et al. "Protein Frustratometer 2: A Tool to Localize Energetic Frustration in Protein Molecules, Now With Electrostatics", Nucleic Acids Research, 44(WEB Server Issue): W356-W360, Published Online Apr. 29, 2016.
Kuroda et al. "Computer-Aided Antibody Design", Protein Engineering, Design & Selection, 25(10): 507-521, Published Online Jun. 2, 2012.
Lippow et al. "Computational Design of Antibody Affinity improvement Beyond In Vivo Maturation", Nature Biotechnology, 25(10): 1171-1176, Oct. 2007.
Miklos et al. "Structure-Based Design of Supercharged, Highly Thermoresistant Antibodies", Chemistry & Biology, 19(4): 449-455, Apr. 20, 2012.
Offredi et al. "De Novo Backbone and Sequence Design of an Idealized Alpha/Beta-Barrel Protein: Evidence of Stable Tertiary Structure", Journal of Molecular Biology, 325(1): 163-174, Jan. 3, 2003.
Rohl et al. "Protein Structure Prediction Using Rosetta", Methods in Enzymology, 383: 66-93, Jan. 2004.
Smirnov et al. "Robotic QM/MM-Driven Maturation of Antibody Combining Sites", Science Advances, 2(10): e1501695-1-e1501695-9, Oct. 19, 2016.
Office Action dated Dec. 24, 2018 From the Israel Patent Office Re. Application No. 249955 and Its Translation Into English. (5 Pages).
Result of Consultation dated Oct. 28, 2019 From the European Patent Office Re. Application No. 15748315.7. (5 Pages).
Notice of Reasons for Refusal dated Jul. 19, 2019 From the Japan Patent Office Re. Application No. 2017-500880 and Its Translation Into English. (7 Pages).

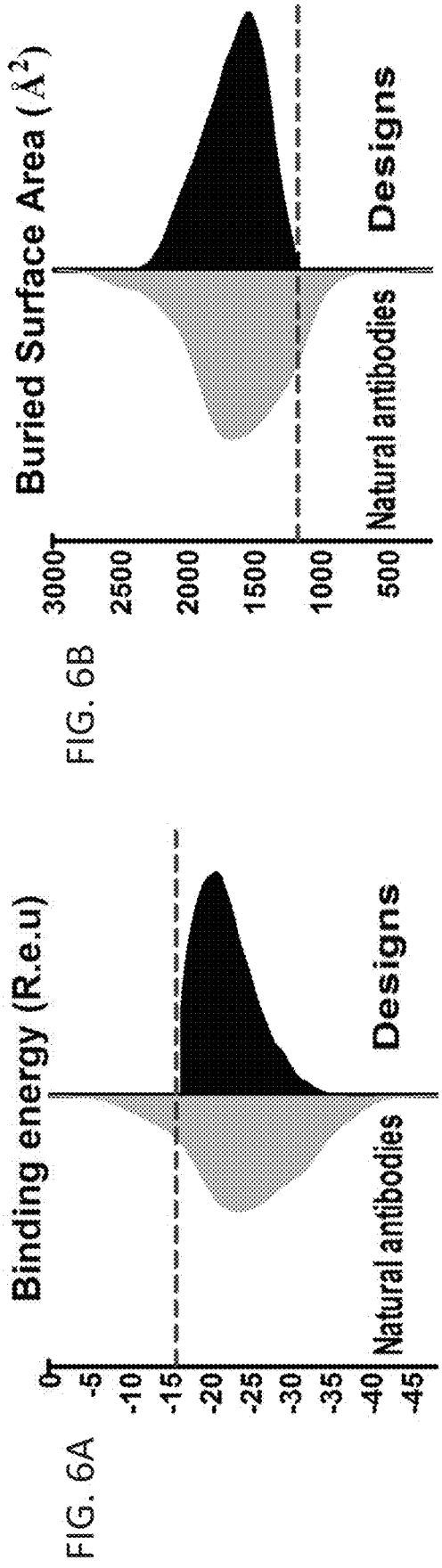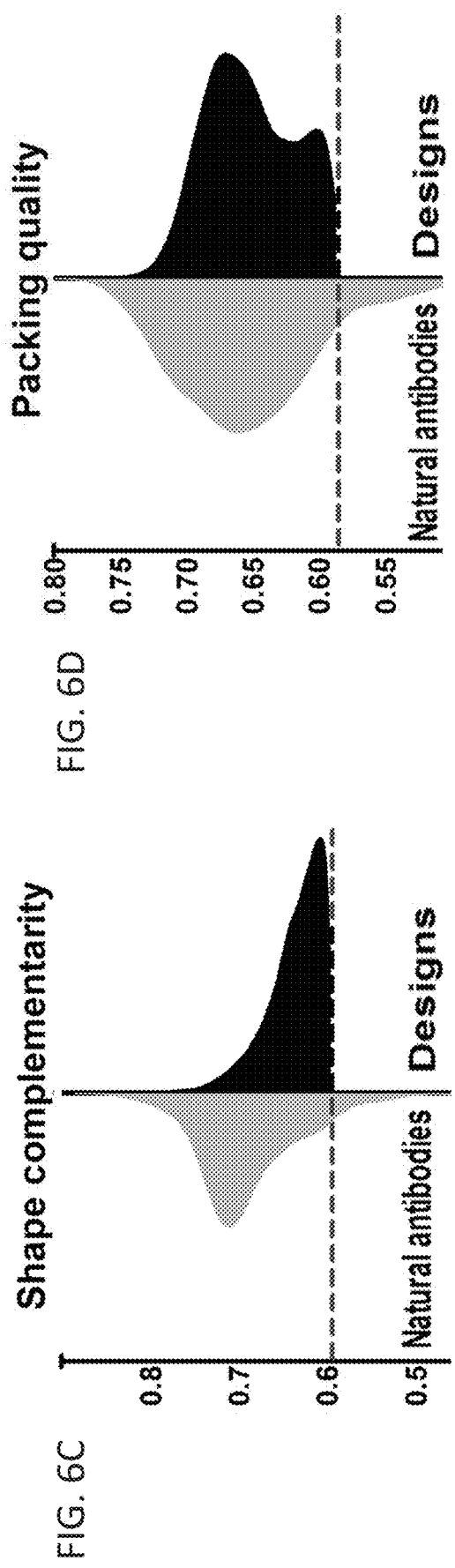

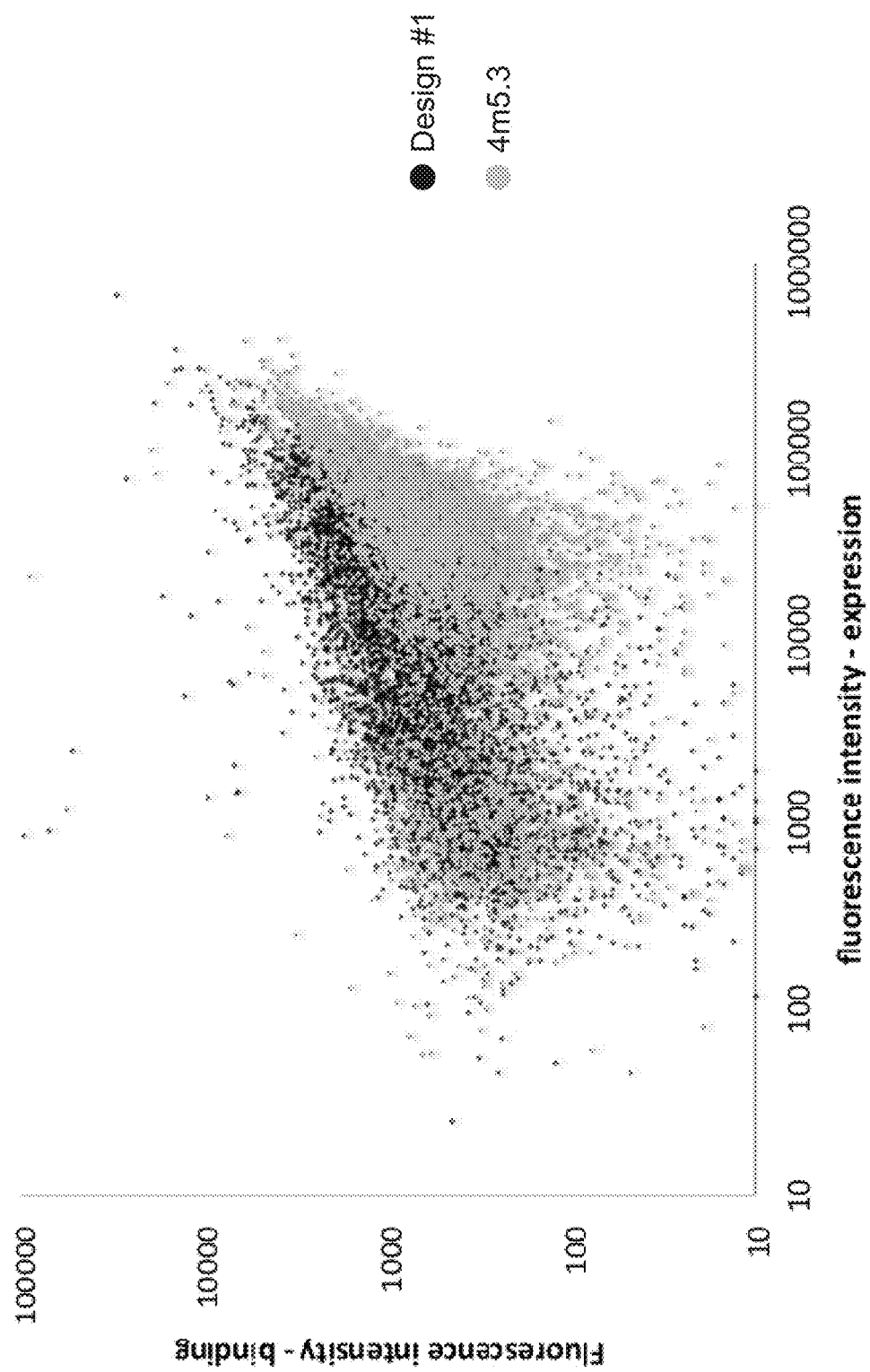

FIG. 9

SEQUENCE LISTING

<160> NUMBER OF SEQ ID NOS: 13

<210> SEQ ID NO 1
<211> LENGTH: 825
<212> TYPE: DNA
<213> ORGANISM: Artificial Sequence
<220> FEATURE:
<223> OTHER INFORMATION: Anti-ACP-AB   design 1 Nucleotide Sequence

<400> SEQUENCE: 1

```
ggtggaggcg gtagcggagg cggagggtcg gaagtgaaac tggacgaaac cggtggtggt      60
ctggttcagc cgggtggtgc gatgaaactg tcttgcgtta cctctggttt cgacttcggt     120
gactactaca tgctgtgggt tcgtcagtct ccggaaaaag gtctggaatg ggttgcggtt     180
gttggtccag acaactctta caccaactac gcggactctg ttaaaggtcg tttcaccatc     240
tctcgtgacg actctaaatc ttctgtttac ctgcagatga caacctgcg taccgaagac     300 accggtatct actactgcat gggctcttct tggtcccagg actcctcttc cgaatctgtt     360
atgaaatacc tcggtcaggg tacttctgtg accgtttctg gaggtggcgg tagcggaggc     420
```

```
ggcggttctg gaggtggcgg gagcaacgtt gttatgaccc agaccccgct gtctctgcca    480
gtttccctgg gtgaccaggc gtctatctct tgccgttctt ctcagtccct caccgcggaa    540
gcgggtctga ccgttctggc ttggttcctg cagaaaccgg gtcagtctcc aaaggtgctg    600
atctacaaag tttctaaccg tgtgtctggt gttccggacc gtttctctgg ttccggttct    660
ggtaccgact tcaccctgaa aatcaaccgc gttgaagctg aagacctcgg tgtttacttc    720
tgcgcggctt ggaccaactc taaatgggtt ttcggtggtg gcaccaagct ggaaattaag    780
ggtggcggat ccgaacaaaa gcttatttct gaagaggact tgtaa                    825
```

```
<210> SEQ ID NO 2
<211> LENGTH: 825
<212> TYPE: DNA
<213> ORGANISM: Artificial Sequence
<220> FEATURE:
<223> OTHER INFORMATION: Anti-ACP-AB   design 2 Nucleotide Sequence

<400> SEQUENCE: 2
ggtggaggcg gtagcggagg cggagggtcg gaagtgaaac tggacgaaac cggtggtggt     60
ctggttcagc cgggtggtgc gatgaaactg tcttgcgtta cctctggttt cgacttcggt    120
gactactaca tgctgtgggt tcgtcagtct ccggaaaaag gtctggaatg ggttgcggtt    180
gttggtccag acaactctta caccaactac gcggactctg ttaaaggtcg tttcaccatc    240
tctcgtgacg actctaaatc ttctgtttac ctgcagatga acaacctgcg taccgaagac    300
accggtatct actactgcat gggctcttct tggtcccagg actcctcttc cgaatctgtt    360
atgaaatacc tcggtcaggg tacttctgtg accgtttctg gaggtggcgg tagcggaggc    420
ggcggttctg gaggtggcgg gagcaacgtt gttatgaccc agaccccgct gtctctgcca    480
gtttccctgg gtgaccaggc gtctatctct tgccgttctt ctcagtccct caccgcggaa    540
aatggtctga ccgttctggc ttggttcctg cagaaaccgg gtcagtctcc aaaggtgctg    600
atctacaaag tttctaaccg tgtgtctggt gttccggacc gtttctctgg ttccggttct    660
ggtaccgact tcaccctgaa aatcaaccgc gttgaagctg aagacctcgg tgtttacttc    720
tgcgcggctt ggaccaactc taaatgggtt ttcggtggtg gcaccaagct ggaaattaag    780
ggtggcggat ccgaacaaaa gcttatttct gaagaggact tgtaa                    825
```

```
<210> SEQ ID NO 3
<211> LENGTH: 825
<212> TYPE: DNA
<213> ORGANISM: Artificial Sequence
<220> FEATURE:
<223> OTHER INFORMATION: Anti-ACP-AB   design 3 Nucleotide Sequence

<400> SEQUENCE: 3
ggtggaggcg gtagcggagg cggagggtcg gaagtgaaac tggacgaaac cggtggtggt     60
ctggttcagc cgggtggtgc gatgaaactg tcttgcgtta cctctggttt cgacttcggt    120
gactactaca tgctgtgggt tcgtcagtct ccggaaaaag gtctggaatg ggttgcggtt    180
gttggtccag acaactctta caccaactac gcggactctg ttaaaggtcg tttcaccatc    240
tctcgtgacg actctaaatc ttctgtttac ctgcagatga acaacctgcg taccgaagac    300
accggtatct actactgcat gggctcttct tggtcccagg actcctcttc cgaatctgtt    360
atgaaatacc tcggtcaggg tacttctgtg accgtttctg gaggtggcgg tagcggaggc    420
ggcggttctg gaggtggcgg gagcaacgtt gttatgaccc agaccccgct gtctctgcca    480
gtttccctgg gtgaccaggc gtctatctct tgccgttctt ctcagtccct caccgcggaa    540
```
gcgggtctga ccgttctggc ttggttcctg cagaaaccgg gtcagtctcc aaaggtgctg    600
atctacaaag tttctaaccg tgtgtctggt gttccggacc gtttctctgg ttccggttct    660
ggtaccgact tcaccctgaa aatcaaccgc gttgaagctg aagacctcgg tgtttacttc    720
tgcgcggctt ggaccaactg gaaatgggtt ttcggtggtg gcaccaagct ggaaattaag    780
ggtggcggat ccgaacaaaa gcttatttct gaagaggact tgtaa                    825

<210> SEQ ID NO 4
<211> LENGTH: 831
<212> TYPE: DNA
<213> ORGANISM: Artificial Sequence
<220> FEATURE:
<223> OTHER INFORMATION: Anti-ACP-AB   design 4 Nucleotide Sequence

<400> SEQUENCE: 4
ggtggaggcg gtagcggagg cggagggtcg gaagtgaaac tggacgaaac cggtggtggt    60
ctggttcagc cggtggtgc gatgaaactg tcttgcgtta cctctggttt cgacttcggt    120
gactactaca tgctgtgggt tcgtcagtct ccggaaaaag gtctggaatg ggttgcgcag    180
ttccgtaaca aaccgtacaa ctacgaaacc tactacgcgg actctgttaa aggtcgtttc    240
accatctctc gtgacgactc taaatcttct gtttacctgc agatgaacaa cctgcgtacc    300
gaagacaccg gtatctacta ctgcatgggc tcttcttggt cccaggactc ctcttccgaa    360
tctgttatga aatacctcgg tcagggtact tctgtgaccg tttctggagg tggcggtagc    420
ggaggcggcg gttctggagg tggcgggagc aacgttgtta tgacccagac cccgctgtct    480
ctgccagttt ccctgggtga ccaggcgtct atctcttgcc gttcttctca gtccctcacc    540
gcggaagcgg gtctgaccgt tctggcttgg ttcctgcaga aaccgggtca gtctccaaag    600
gtgctgatct acaaagtttc taaccgtgtg tctggtgttc cggaccgttt ctctggttcc    660
ggttctggta ccgacttcac cctgaaaatc aaccgcgttg aagctgaaga cctcggtgtt    720
tacttctgcg cggcttggac caactctaaa tgggttttcg gtggtggcac caagctggaa    780
attaagggtg gcggatccga acaaaagctt atttctgaag aggacttgta a             831

<210> SEQ ID NO 5
<211> LENGTH: 801
<212> TYPE: DNA
<213> ORGANISM: Artificial Sequence
<220> FEATURE:
<223> OTHER INFORMATION: Anti-ACP-AB   design 5 Nucleotide Sequence

<400> SEQUENCE: 5
ggtggaggcg gtagcggagg cggagggtcg gaagtgaaac tggacgaaac cggtggtggt    60
ctggttcagc cggtggtgc gatgaaactg tcttgcgtta cctctggttt cgacttcggt    120
gactactaca tgctgtgggt tcgtcagtct ccggaaaaag gtctggaatg ggttgcggtt    180
gttggtccag acaactctta caccaactac gcggactctg ttaaaggtcg tttcaccatc    240
tctcgtgacg actctaaatc ttctgtttac ctgcagatga caacctgcg taccgaagac    300 accggtatct attactgtac tggtgcgtct tacggtatgg aatacctggg tcagggtact    360
tctgtgaccg tttctggagg tggcggtagc ggaggcggcg gttctggagg tggcgggagc    420
aacgttgtta tgacccagac cccgctgtct ctgccagttt ccctgggtga ccaggcgtct    480
atctcttgcc gttcttctca gtccctcacc gcggaagcgg gtctgaccgt tctggcttgg    540
ttcctgcaga aaccgggtca gtctccaaag gtgctgatct acaaagtttc taaccgtgtg    600

```
tctggtgttc cggaccgttt ctctggttcc ggttctggta ccgacttcac cctgaaaatc    660
aaccgcgttg aagctgaaga cctcggtgtt tacttctgcg cggcttggac caactctaaa    720
tgggttttcg gtggtggcac caagctggaa attaagggtg gcggatccga acaaaagctt    780
atttctgaag aggacttgta a                                              801
```

<210> SEQ ID NO 6
<211> LENGTH: 320
<212> TYPE: PRT
<213> ORGANISM: Artificial Sequence
<220> FEATURE:
<223> OTHER INFORMATION: Design #6  Amino Acid coding sequence

<400> SEQUENCE: 6

```
Asp Arg Ile Asn Thr Val Arg Gly Pro Ile Thr Ile Ser Glu Ala Gly
1               5                   10                  15

Phe Thr Leu Thr His Glu His Ile Cys Gly Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Ile Gly Arg Asp Val Ser Leu Leu Ala
65                  70                  75                  80

Glu Val Ser Arg Ala Ala Asp Val His Ile Val Ala Ala Thr Gly Leu
                85                  90                  95

Trp Tyr Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Lys Val Ala Thr Thr Gly Lys Ala Thr Pro
    130                 135                 140

Phe Gln Glu Leu Val Leu Lys Ala Ala Ala Arg Ala Ser Leu Ala Thr
145                 150                 155                 160

Gly Val Pro Val Thr Thr His Thr Ala Ala Ser Gln Arg Asp Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Asp Ile Ser Tyr Leu Thr Ala
        195                 200                 205

Leu Ala Ala Arg Gly Tyr Leu Ile Ala Phe Asp Arg Phe Gly His Gln
    210                 215                 220

Gly Met Asn Gly Ala Pro Thr Asp Glu Glu Arg Ile Arg Thr Leu Val
225                 230                 235                 240

Ala Leu Leu Arg Asp Gly Tyr Glu Lys Gln Ile Leu Leu Ser Asn Asp
                245                 250                 255

Trp Leu Phe Gly Tyr Ser Ser Tyr Thr Thr Asn Ile Met Asp Val Met
            260                 265                 270

Asp Arg Tyr Asn Pro Asp Gly Met Ala His Ile Pro Leu Arg Val Ile
        275                 280                 285

Pro His Leu Arg Glu Lys Gly Val Pro Gln Glu Thr Leu Ala Gly Ile
    290                 295                 300

Thr Val Thr Asn Pro Ala Arg Phe Leu Ser Pro Thr Leu Arg Ala Ser
305                 310                 315                 320
```

```
<210> SEQ ID NO 7
<211> LENGTH: 317
<212> TYPE: PRT
<213> ORGANISM: Artificial Sequence
<220> FEATURE:
<223> OTHER INFORMATION: Design #7  Amino Acid coding sequence

<400> SEQUENCE: 7
```

Asp Arg Ile Asn Thr Val Arg Gly Pro Ile Thr Ile Ser Glu Ala Gly
1               5                   10                  15

Phe Thr Leu Thr His Glu His Ile Cys Gly Ser Ser Ala Gly Phe Leu
            20                  25                  30

Arg Ala Trp Pro Glu Phe Phe Gly Ser Arg Lys Ala Leu Ala Glu Lys
        35                  40                  45

Ala Val Arg Gly Leu Arg Arg Ala Arg Ala Ala Gly Val Arg Thr Ile
    50                  55                  60

Val Asp Val Ser Thr Phe Asp Ile Gly Arg Asp Val Ser Leu Leu Ala
65                  70                  75                  80

Glu Val Ser Arg Ala Ala Asp Val His Ile Val Ala Ala Thr Gly Leu
                85                  90                  95

Trp Tyr Asp Pro Pro Leu Ser Met Arg Leu Arg Ser Val Glu Glu Leu
            100                 105                 110

Thr Gln Phe Phe Leu Arg Glu Ile Gln Tyr Gly Ile Glu Asp Thr Gly
        115                 120                 125

Ile Arg Ala Gly Ile Ile Lys Val Ala Thr Thr Gly Lys Ala Thr Pro
    130                 135                 140

Phe Gln Glu Leu Val Leu Lys Ala Ala Arg Ala Ser Leu Ala Thr
145                 150                 155                 160

Gly Val Pro Val Thr Thr His Thr Ala Ala Ser Gln Arg Asp Gly Glu
                165                 170                 175

Gln Gln Ala Ala Ile Phe Glu Ser Glu Gly Leu Ser Pro Ser Arg Val
            180                 185                 190

Cys Ile Gly His Ser Asp Asp Thr Asp Leu Ser Tyr Leu Thr Ala
                195                 200                 205

Leu Ala Ala Arg Gly Tyr Phe Val Ser Phe Asp Arg Ile Ala Leu Ile
210                 215                 220

Lys Tyr Ala Pro Glu Ser Ala Arg Ile Ala Leu Ile Leu Tyr Leu Val
225                 230                 235                 240

Ser Glu Gly Phe Glu Asn Gln Ile Leu Val Ser Gly Asp Trp Leu Phe
                245                 250                 255

Gly Phe Ser Ser Tyr Thr Thr Asn Ile Met Asp Asn Met Asp Arg Val
            260                 265                 270

Asn Pro Asp Gly Met Ala Phe Ile Pro Leu Arg Val Ile Pro Tyr Leu
        275                 280                 285

Arg Glu Lys Gly Val Pro Gln Glu Thr Leu Ala Gly Ile Thr Val Thr
    290                 295                 300

Asn Pro Ala Arg Phe Leu Ser Pro Thr Leu Arg Ala Ser
305                 310                 315

```
<210> SEQ ID NO 8
<211> LENGTH: 328
<212> TYPE: PRT
<213> ORGANISM: Artificial Sequence
<220> FEATURE:
<223> OTHER INFORMATION: TIM-barrel fold Design #8  Amino Acid coding
      sequence

<400> SEQUENCE: 8
```

```
Met Arg Ile Pro Leu Val Gly Lys Asp Ser Ile Glu Ser Lys Asp Ile
1               5                   10                  15

Gly Phe Thr Leu Ile His Glu His Leu Arg Val Phe Ser Glu Ala Val
            20                  25                  30

Arg Gln Gln Trp Pro His Leu Tyr Asn Glu Asp Glu Phe Arg Asn
        35                  40                  45

Ala Val Asn Glu Val Lys Arg Ala Met Gln Phe Gly Val Lys Thr Ile
    50                  55                  60

Val Asp Pro Thr Val Met Gly Leu Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Trp Ile Phe Val Asp Leu Pro Phe Tyr Phe Leu Asn Arg Ser Ile Asp
                100                 105                 110

Glu Ile Ala Asp Leu Phe Ile His Asp Ile Lys Glu Gly Ile Gln Gly
            115                 120                 125

Thr Leu Asn Lys Ala Gly Phe Val Lys Ile Ala Ala Asp Gln Pro Gly
    130                 135                 140

Ile Thr Lys Asp Val Glu Lys Val Ile Arg Ala Ala Arg Ala Ser
145                 150                 155                 160

Lys Glu Thr Gly Cys Pro Ile Ile Ser His Ser Asn Ala His Asn Asn
                165                 170                 175

Asp Gly Glu Ala Gln Gln Glu Ile Leu Ala Cys Glu Gly Val Asp Pro
            180                 185                 190

Cys Lys Ile Leu Ile Gly His Leu Gly Asp Thr Asp Asn Leu Asp Tyr
            195                 200                 205

Ile Arg Lys Ile Ala Gln Arg Gly Ser Phe Ile Gly Ile Asp Arg Ile
        210                 215                 220

Pro His Ser Gly Ile Gly Ala Glu Gly Asn Ala Ser Ala Ser Ala Leu
225                 230                 235                 240

Phe Gly Asn Arg Ser Trp Gln Glu Arg Ala Ser Val Ile Lys Ala Met
                245                 250                 255

Ile Asp Asp Gly Tyr Ala Asp Lys Ile Leu Met Ser His Asp Tyr Cys
            260                 265                 270

Cys Thr Phe Asp Val Gly Ala Ala Lys Pro Glu Tyr Lys Pro Ser Met
    275                 280                 285

Ala Pro Arg Trp Ser Ile Thr Val Ile Phe Glu Asp Thr Ile Pro Phe
    290                 295                 300

Leu Lys Arg Asn Gly Val Asn Glu Val Leu Ala Thr Ile Phe Lys
305                 310                 315                 320

Glu Asn Pro Lys Lys Phe Phe Ser
                325
```

<210> SEQ ID NO 9
<211> LENGTH: 327
<212> TYPE: PRT
<213> ORGANISM: Artificial Sequence
<220> FEATURE:
<223> OTHER INFORMATION: TIM-barrel fold Design #9 Amino Acid coding sequence

<400> SEQUENCE: 9

```
Met Arg Ile Pro Leu Val Gly Lys Asp Ser Ile Glu Ser Lys Asp Ile
1               5                   10                  15

Gly Phe Thr Leu Ile His Glu His Leu Arg Val Phe Ser Glu Ala Val
```

20                  25                  30
Arg Gln Gln Trp Pro His Leu Tyr Asn Glu Asp Glu Glu Phe Arg Asn
                35                  40                  45

Ala Val Asn Glu Val Lys Arg Ala Met Gln Phe Gly Val Lys Thr Ile
        50                  55                  60

Val Asp Pro Thr Val Met Gly Leu Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Trp Ile Phe Val Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Gly
        115                 120                 125

Thr Leu Asn Lys Ala Gly Phe Ile Lys Leu Ala Ser Ser Lys Gly Arg
    130                 135                 140

Ile Thr Pro Tyr Glu Glu Lys Val Leu Arg Ala Ala Arg Ala Gln
145                 150                 155                 160

Lys Glu Thr Gly Ala Pro Ile Ile Ser His Thr Gln Glu Gly Gln Gln
                165                 170                 175

Gly Pro Gln Gln Ala Glu Leu Leu Lys Gln Gly Ala Asp Pro Glu
            180                 185                 190

Lys Ile Leu Ile Gly His Ser Asp Asp Thr Asp Leu Asp Trp Ile
        195                 200                 205

Arg Lys Met Ala Ala Leu Gly Ser Phe Ile Gly Phe Asp Arg Ile Pro
    210                 215                 220

His Ser Gly Ile Gly Ala Glu Asp Asn Ala Ser Ala Thr Ala Leu Phe
225                 230                 235                 240

Gly Asn Arg Ser Asp Gln Glu Arg Ala Arg Ile Ile Lys Ala Met Ile
                245                 250                 255

Asp Glu Gly Phe Ala Asn Lys Val Ile Met Ser His Asp Tyr Cys Cys
            260                 265                 270

Thr Phe Asp Val Gly Thr Ala Lys Pro Glu Tyr Lys Pro Ser Ala Ala
        275                 280                 285

Pro Arg Trp Ser Ile Thr Leu Met Phe Glu Asp Thr Ile Pro Phe Leu
    290                 295                 300

Lys Arg Asn Gly Val Asn Glu Glu Val Ile Ala Thr Ile Phe Lys Glu
305                 310                 315                 320

Asn Pro Lys Lys Phe Phe Ser
                325

<210> SEQ ID NO 10
<211> LENGTH: 327
<212> TYPE: PRT
<213> ORGANISM: Artificial Sequence
<220> FEATURE:
<223> OTHER INFORMATION: TIM-barrel fold Design #10  Amino Acid coding
      sequence

<400> SEQUENCE: 10

Met Arg Ile Pro Leu Val Gly Lys Asp Ser Ile Glu Ser Lys Asp Ile
1               5                   10                  15

Gly Phe Thr Leu Ile His Glu His Leu Arg Val Phe Ser Glu Ala Val
                20                  25                  30

Arg Gln Gln Trp Pro His Leu Tyr Asn Glu Asp Glu Glu Phe Arg Asn
            35                  40                  45

```
Ala Val Asn Glu Val Lys Arg Ala Met Gln Phe Gly Val Lys Thr Ile
 50                  55                  60
Val Asp Pro Thr Val Met Gly Leu Gly Arg Asp Ile Arg Phe Met Glu
 65                  70                  75                  80
Lys Val Val Lys Ala Thr Gly Ile Asn Leu Val Ala Gly Thr Gly Ile
                     85                  90                  95
Trp Ile Phe Val Asp Leu Pro Phe Tyr Phe Leu Asn Arg Ser Ile Asp
                    100                 105                 110
Glu Ile Ala Asp Leu Phe Ile His Asp Ile Lys Glu Gly Ile Gln Gly
                    115                 120                 125
Thr Leu Asn Lys Ala Gly Phe Ile Lys Val Ala Thr Thr Gly Lys Ala
    130                 135                 140
Thr Pro Asp Glu Glu Lys Val Ile Arg Ala Ala Arg Ala Ser Lys
145                 150                 155                 160
Glu Thr Gly Cys Pro Ile Ile Thr His Thr Ala Ala Ser Gln Arg Asp
                    165                 170                 175
Gly Glu Glu Gln Ala Glu Ile Glu Glu Cys Gly Gly Pro Pro Cys
                180                 185                 190
Arg Ile Met Ile Gly His Ser Asp Asp Thr Asp Asp Leu Asp Trp Ile
            195                 200                 205
Arg Lys Leu Ala Gln Lys Gly Tyr Phe Ile Gly Phe Asp Arg Met Pro
    210                 215                 220
His Ser Gly Ile Gly Ala Glu Asp Asn Ala Ser Ala Thr Ala Leu Phe
225                 230                 235                 240
Gly Thr Arg Ser Asp Gln Thr Arg Asn Glu Ala Ile Lys Arg Ile Ile
                245                 250                 255
Asp Asp Gly Tyr Ala Glu Lys Ile Leu Met Ser His Asp Tyr Cys Cys
                260                 265                 270
Thr Ile Asp Val Gly Ala Ala Lys Pro Glu His Lys Pro Ser Ala Ala
            275                 280                 285
Pro Arg Trp Ser Ile Thr Leu Ile Phe Glu Asp Thr Ile Pro Phe Leu
    290                 295                 300
Lys Arg Asn Gly Val Asn Glu Glu Val Ile Ala Thr Ile Phe Lys Glu
305                 310                 315                 320
Asn Pro Lys Lys Phe Phe Ser
                325

<210> SEQ ID NO 11
<211> LENGTH: 329
<212> TYPE: PRT
<213> ORGANISM: Artificial Sequence
<220> FEATURE:
<223> OTHER INFORMATION: TIM-barrel fold Design #11  Amino Acid coding
      sequence

<400> SEQUENCE: 11

Met Arg Ile Pro Leu Val Gly Lys Asp Ser Ile Glu Ser Lys Asp Ile
  1               5                  10                  15
Gly Phe Thr Leu Ile His Glu His Leu Arg Val Phe Ser Glu Ala Val
                 20                  25                  30
Arg Gln Gln Trp Pro His Leu Tyr Asn Glu Asp Glu Glu Phe Arg Asn
             35                  40                  45
Ala Val Asn Glu Val Lys Arg Ala Met Gln Phe Gly Val Lys Thr Ile
         50                  55                  60
Val Asp Pro Thr Val Met Gly Leu Gly Arg Asp Ile Arg Phe Met Glu
 65                  70                  75                  80
```

```
Lys Val Val Lys Ala Thr Gly Ile Asn Leu Val Ala Gly Thr Gly Ile
                85                  90                  95

Trp Ile Phe Val Asp Leu Pro Phe Tyr Phe Leu Asn Arg Ser Ile Asp
                100                 105                 110

Glu Ile Ala Asp Leu Phe Ile His Asp Ile Lys Glu Gly Ile Gln Gly
                115                 120                 125

Thr Leu Asn Lys Ala Gly Met Ile Ala Glu Ile Gly Thr Ser Glu Gly
                130                 135                 140

Glu Met Ala Pro Glu Glu Lys Leu Leu Arg Ala Ala Gln Ala
145                 150                 155                 160

Ala Asn Glu Thr Gly Arg Pro Ile Thr Thr His Thr Ala Ser Gln
                165                 170                 175

Arg Val Gly Asp Glu Val Ala Arg Val Leu Glu Glu Gly Gly Val Pro
                180                 185                 190

Pro Cys Lys Val Cys Ile Gly His Ser Asp Asp Thr Asp Asp Leu Asp
                195                 200                 205

Trp Ile Arg Lys Leu Ala Ala Arg Gly Tyr Phe Ile Gly Phe Asp Arg
                210                 215                 220

Ile Gly His Ser Gly Ile Gly Ala Glu Asp Asn Ala Ser Ala Ser Ala
225                 230                 235                 240

Leu Ala Gly Asn Arg Ser Asp Gln Thr Arg Ala Glu Cys Val Lys Arg
                245                 250                 255

Met Ala Asp Glu Gly Phe Ala Glu Lys Ile Met Val Ser His Asp Tyr
                260                 265                 270

Cys Cys Thr Ile Asp Val Gly Thr Ala Lys Pro Glu Tyr Lys Pro Ser
                275                 280                 285

Ala Ala Pro Arg Trp Ser Ile Thr Leu Ile Phe Glu Asp Thr Ile Pro
                290                 295                 300

Phe Leu Lys Arg Asn Gly Val Asn Glu Glu Val Ile Ala Thr Ile Phe
305                 310                 315                 320

Lys Glu Asn Pro Lys Lys Phe Phe Ser
                325

<210> SEQ ID NO 12
<211> LENGTH: 329
<212> TYPE: PRT
<213> ORGANISM: Artificial Sequence
<220> FEATURE:
<223> OTHER INFORMATION: TIM-barrel fold Design #12  Amino Acid coding
      sequence

<400> SEQUENCE: 12

Met Arg Ile Pro Leu Val Gly Lys Asp Ser Ile Glu Ser Lys Asp Ile
1               5                   10                  15

Gly Phe Thr Leu Ile His Glu His Leu Arg Val Phe Ser Glu Ala Val
                20                  25                  30

Arg Gln Gln Trp Pro His Leu Tyr Asn Glu Asp Glu Glu Phe Arg Asn
                35                  40                  45

Ala Val Asn Glu Val Lys Arg Ala Met Gln Phe Gly Val Lys Thr Ile
                50                  55                  60

Val Asp Pro Thr Val Met Gly Leu Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Trp Ile Phe Val Asp Leu Pro Phe Tyr Phe Leu Asn Arg Ser Ile Asp
```

```
            100                 105                 110
Glu Ile Ala Asp Leu Phe Ile His Asp Ile Lys Glu Gly Ile Gln Gly
            115                 120                 125

Thr Leu Asn Lys Ala Gly Met Ile Ala Glu Ile Gly Thr Ser Glu Gly
            130                 135                 140

Glu Cys Ala Pro Glu Gln Lys Ala Leu Arg Ala Ala Ala Gln Ala
145                 150                 155                 160

Ala Asn Glu Thr Gly Arg Pro Ile Thr Thr His Thr Ala Ala Ser Gln
                165                 170                 175

Arg Thr Gly Glu Glu Gln Ala Arg Val Leu Glu Cys Gly Gly Val Pro
            180                 185                 190

Gly Cys Lys Ile Cys Ile Gly His Met Cys Gly Asn Thr Asp Leu Glu
            195                 200                 205

Gln His Arg Lys Leu Ala Asp Arg Gly Tyr Phe Leu Gly Phe Asp Arg
            210                 215                 220

Ile Gly His Ser Gly Ile Gly Leu Glu Asp Asn Ala Ser Ala Ser Ala
225                 230                 235                 240

Leu Met Gly Asn Arg Ser Trp Gln Glu Arg Ala Glu Leu Ile Lys Ala
                245                 250                 255

Ile Ile Asp Glu Gly Tyr Ala Asp Lys Ile Met Val Ser His Asp Tyr
            260                 265                 270

Cys Cys Thr Ile Asp Val Gly Ala Ala Lys Pro Glu Tyr Lys Pro Lys
            275                 280                 285

Met Ala Pro Arg Trp Ser Ile Thr Leu Ile Phe Glu Asp Thr Ile Pro
            290                 295                 300

Phe Leu Lys Arg Asn Gly Val Asn Glu Glu Val Ile Ala Thr Ile Phe
305                 310                 315                 320

Lys Glu Asn Pro Lys Lys Phe Phe Ser
                325

<210> SEQ ID NO 13
<211> LENGTH: 314
<212> TYPE: PRT
<213> ORGANISM: Sulfolobus solfataricus

<400> SEQUENCE: 13

Met Arg Ile Pro Leu Val Gly Lys Asp Ser Ile Glu Ser Lys Asp Ile
1               5                   10                  15

Gly Phe Thr Leu Ile His Glu His Leu Arg Val Phe Ser Glu Ala Val
            20                  25                  30

Arg Gln Gln Trp Pro His Leu Tyr Asn Glu Asp Glu Phe Arg Asn
            35                  40                  45

Ala Val Asn Glu Val Lys Arg Ala Met Gln Phe Gly Val Lys Thr Ile
50                  55                  60

Val Asp Pro Thr Val Met Gly Leu Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Tyr Ile Tyr Ile Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Gly
            115                 120                 125

Thr Leu Asn Lys Ala Gly Phe Val Lys Ile Ala Ala Asp Glu Pro Gly
            130                 135                 140
```

-continued

```
Ile Thr Lys Asp Val Glu Lys Val Ile Arg Ala Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Glu Gly Val Asp Pro
            180                 185                 190

Gly Lys Ile Leu Ile Gly His Leu Gly Asp Thr Asp Asn Ile Asp Tyr
        195                 200                 205

Ile Lys Lys Ile Ala Asp Lys Gly Ser Phe Ile Gly Leu Asp Arg Tyr
    210                 215                 220

Gly Leu Asp Leu Phe Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Cys Cys Thr Ile Asp Trp Gly Thr Ala Lys Pro Glu Tyr Lys Pro
            260                 265                 270

Lys Leu Ala Pro Arg Trp Ser Ile Thr Leu Ile Phe Glu Asp Thr Ile
            275                 280                 285

Pro Phe Leu Lys Arg Asn Gly Val Asn Glu Glu Val Ile Ala Thr Ile
        290                 295                 300

Phe Lys Glu Asn Pro Lys Lys Phe Phe Ser
305                 310
```

METHOD OF COMPUTATIONAL PROTEIN DESIGN

RELATED APPLICATIONS

This application is a National Phase of PCT Patent Application No. PCT/IL2015/050696 having International filing date of Jul. 6, 2015, which claims the benefit of priority under 35 USC § 119(e) of U.S. Provisional Patent Application No. 62/021,309 filed on Jul. 7, 2014. The contents of the above applications are all incorporated by reference as if fully set forth herein in their entirety.

SEQUENCE LISTING STATEMENT

The ASCII file, entitled 68711SequenceListing.txt, created on Jan. 5, 2017, comprising 29,700 bytes bytes, submitted concurrently with the filing of this application is incorporated herein by reference.

FIELD AND BACKGROUND OF THE INVENTION

The present invention, in some embodiments thereof, relates to computational chemistry and computational protein design and, more particularly, but not exclusively, to a method of computationally constructing a library of amino-acid sequences having a common structural fold; and a method of designing and selecting an amino-acid sequence having a desired affinity to a molecular surface of interest of a molecular entity. These methods can be used, for example, for designing binding proteins having structural stability and high binding affinity towards predetermined molecular targets. The present invention, in some embodiments thereof, further relates to computational chemistry and, more particularly, but not exclusively, to a method of producing an amino-acid sequence having a desired affinity to a molecular surface of interest and to an amino acid sequence having a desired affinity to a molecular surface of interest.

Molecular recognition underlies many central biological processes, hence, an ability to design novel protein interactions holds great promise for creating highly specific and potent molecules for use in the chemical industry as well as therapeutics, diagnostics, and research probes. Recent strategies in protein binder design have used naturally occurring proteins as scaffolds onto which binding surfaces were designed, while relying either on a single protein scaffold, or several hundred different scaffolds to achieve the structural characteristics required for binding. In all cases the designed scaffolds were treated as rigid structural elements with minimal perturbation of their backbone degrees of freedom. Some of these strategies resulted in the experimentally validated design of homooligomers, inhibitors, and protein affinity purification reagents.

A computational exercise in designing a de novo protein having a sequence of, for example, some 220 naturally occurring amino acids (roughly equivalent to an antibody Fv domain), would require $20^{220}=10^{286}$ unique amino acid permutations to define the amino acid sequence of one protein; a feat current computation machines are yet unequipped to handle. Current computational design methodologies use naturally occurring rigid scaffolds to design de novo molecular function; however, these approaches are fundamentally limited by the number of suitable scaffolds of known three-dimensional structures. In addition, several general limitations have been made about successfully designed binding surfaces according to the abovementioned strategies:
1. They comprise surfaces rich in secondary-structure content (α-helices and β-sheets);
2. Interactions with the target are largely mediated by hydrophobic amino acid side-chains; and
3. The buried surface area upon binding is at or smaller than the average for naturally occurring protein-protein interactions, estimated at 1600 Å$^2$. The design of large and polar surfaces, essential to make computational binder design general, remains an unmet challenge.

Some common protein folds, which have been identified in many proteins, some of which are seemingly unrelated to each other in terms of genealogy, organism and function, which are also known as conserved domain folds, offer a unique opportunity to study the fundamentals of sequence-structure-function relationships, albeit several observations of proteins sharing a common fold but serving an unrelated function still challenges modern science. Nonetheless, some studies have attempted to harness the common structural fold to assist in computational protein design.

One of the most fascinating conserved protein folds is known as the TIM-barrel, or α/β protein fold. Observations of this fold, which is shared by many proteins and many organisms, have assisted in the development of the convergent evolution theory pertaining to similar features in species of different lineages. Likewise, TIM-barrels have been contemplated as suitable scaffolds for de novo protein design.

Offredi, F. et al. [*J Mol Biol.*, 2003, 325(1), p. 163-74], used structural data from crystal structures of TIM-barrel fold protein to define geometrical rules of an "ideal" fold having a 4-fold symmetry, and following definition of the backbone geometry, attempted a sequence search to find the sequence that would stabilize the conformation.

Figueroa, M. et al. [*PLoS One*, 2013, 8(8), p. e71858] used the Rosetta suite to design a TIM-barrel protein using a model known as "Octarellin V" as the starting backbone model, and constructed the loop regions from six-residue fragments of PDB proteins displaying a select secondary structure pattern using the Rosetta loop-building protocol. Final structures were evaluated based on hydrogen bonding between β-strands, packing at the β-strand-α-helix interface and Rosetta all-atom energy function.

One of the most studied families of proteins in the context of protein binding interactions, structure prediction and molecular design is the family of antibodies. Antibodies comprise two types of polypeptide, referred to as the light chain and the heavy chain. The light chain and heavy chain are composed of distinct domains with similar structures, the light chain comprising two such domains, and the heavy chain comprising four such domains. Each domain comprises a "sandwich" characterized by two β-sheets composed of anti-parallel β-strands, with a disulfide bond linking the two β-sheets. The domain at the N-terminal end of each of the heavy chain and the light chain is variable in amino acid sequence. These "variable domains" provide the wide diversity of different antibodies. The other domains compose the "constant region" of the heavy and light chains.

An antigen-binding region of an antibody is formed from one light chain variable domain in combination with one heavy chain variable domain. In a variable domain, variability in amino acid sequence is restricted primarily to 3 "complementarity-determining regions (CDRs)" (also known as "hypervariable regions", and individually termed CDR1, CDR2 and CDR3), separated by relatively conserved "framework regions". Thus, an antigen-binding region contains three light chain CDRs (termed L1, L2 and L3) and three heavy chain CDRs (termed H1, H2 and H3). The three CDRs in each domain are clustered at the target binding surface of the antibody, each CDR being associated with a loop linking two β-strands. The conserved framework regions form a rigid structure characterized by structural homology, which provides the antibody with stability and affects the CDRs conformational rigidity.

Much of the variability in CDRs is a result of V(D)J (Variable, Diverse, and Joining gene segments) recombination, wherein an immune cell genome undergoes recombination such that one of about 44 V gene segments is randomly combined with one of 6 J gene segments. In addition, in the heavy chain gene, one of 27 D gene segments is located between the selected V and J gene segments. The V gene segment is the largest, coding for CDR1 and CDR2, as well as for a portion of the CDR3, whereas the D and J gene fragments code for portions of CDR3 (L3 or H3 in the case of the J fragment, H3 in the case of the D fragment). V(D)J recombination allows for a wide variety of light chain and heavy chain sequences. Additional variability results from combinations of different heavy and light chains, and from processes, which result in addition and/or deletion of nucleotides or other mutations in the light chain and heavy chain genes.

Despite their tremendous diversity, the CDRs (with the exception of the H3 CDR) fall into a handful of discrete conformations termed "canonical conformations". For example, in hundreds of antibody molecular structures, only seven conformational variants are observed for the L2 CDR. The canonical conformations are characterized by key conserved residue identities that maintain the backbone conformation.

The key challenge in the design of backbone fragments for function is that the designed surface needs both to function (bind its target) and to be conformationally stable. As mentioned above, antibodies are constructed of sequence blocks that alternate highly conserved with highly variable segments, and the molecular structures of antibodies show that the conserved segments belong to a structurally homologous and rigid structure known as the framework, which provides the necessary stability to the antibody, whereas the variable segments cluster at the target binding surface, and were therefore termed the complementarity-determining regions (CDRs).

A key attraction for antibody engineering lies in antibodies' modular architecture, suggesting that a large combinatorial complexity of well-folded backbones could be tapped. As early as the 1980s, observations on the structural modularity of antibodies proposed that synthetic antibodies could be constructed by combining fragments of naturally occurring antibodies. From this insight, investigators have devised a method for antibody humanization, in which CDRs from a mouse antibody were grafted onto a human antibody framework to generate a humanized functional antibody, opening the way to safe therapeutic antibody engineering. These early advances raised excitement that the complete design of antibodies from first principles is achievable, but until recently, computational tools for protein design had not matured sufficiently to realize this objective.

Recent work on computational antibody design aimed at increasing binding affinity [Clark, L A. et al., *Protein Sci.*, 2006, 15(5), p. 949-60; Lippow, S M. et al., *Nat. Biotechnol.*, 2007, 25(10), p. 1171-6; Clark, L A. et al., *Protein Eng Des Sel.*, 2009, 22(2), p. 93-101], identify favorable positions for experimental random mutagenesis [Barderas, R. et al., *Proc. Natl. Acad. Sci. USA*, 2008, 105(26), p. 9029-34], modify binding specificity [Farady, C. J. et al., *Bioorg. Med. Chem. Lett.*, 2009, 19(14), p. 3744-7] and increase thermo-resistance [Miklos, A. E. et al., *Chem. Biol.*, 2012, 19(4), p. 449-55].

A de novo antibody design strategy was suggested by Pantazes et al. that capitalizes on observations that antibody CDRs exhibit canonical conformations.

Pantazes and Maranas [*Protein. Eng. Des. Sel.*, 2010, 23, 849-858] describe a general computational method ("OptCDR") for designing binding portions of antibodies by first determining which combinations of canonical structures are most likely to favorably bind a selected antigen, and then performing simultaneous refinement of the CDR backbones and optimal amino acid selection for each position.

Pantazes and Maranas [BMC Bioinformatics 2013, 14:168] also describe a method of predicting antibody structure by using experimentally determined antibody structures to compile a database of 929 modular antibody parts (MAPs), which can be combined to create $2.3 \cdot 10^{10}$ unique antibodies. The MAPS are described as being analogous to V, D and J gene fragments.

Weitzner B. D. et al. [*Proteins*, epub. Feb. 12, 2014], teach initial model is constructed by grafting the individual antibody CDRs onto a chain specific framework, wherein the H3 is modeled de novo while sampling rigid body orientation using the Rosetta docking algorithm.

Shirai H. et al. [*Proteins*, epub. Apr. 22, 2014], teach identifying an antibody Fv domain framework template based on the H3 subtype, the construction of a database of conformations of all canonical loops including H3 associated with position-specific scoring matrices (PSSMs), choosing the most appropriate cluster for a given sequence based on it PSSM score, and subsequently constructing models minimized with harmonic backbone constraints to the template model.

However, even if a method that can theoretically encompass and effectively and systematically sample all the conformational combinatorial space that can be generated by permutations at the gene level, such method would not be able to account for the myriad of random mutations which are observed in naturally occurring antibodies.

Additional background art include U.S. Patent Application Nos. 20030059827, 20110224100, 20130244940, 20130296221 and 20140005125, Smadbeck, J., Peterson, M. B., Khoury, G. A., Taylor, M. S., Floudas, C. A. "*Protein WISDOM: A Workbench for In silico De novo Design of BioMolecules*", *J. Vis. Exp.*, (77), e50476, and the review "*Protein folding and de novo protein design for biotechnological applications*" by Khoury, G. A., Smadbeck, J Kieslich, C. A., and Floudas, C. A., *Trends in Biotechnology*, 2014, 32(2), p. 99-109, which is incorporated by reference in its entirety as if fully set forth herein.

SUMMARY OF THE INVENTION

According to an aspect of some embodiments of the present invention there is provided a method of computationally constructing a library of amino-acid sequences having a common structural fold, the method comprising the following steps:

(i) providing one or more source structures having the common structural fold, whereas the common structural fold having conserved structural regions defining a structural framework and diverse structural regions, and the structural framework having locations of highest structural conservation;

(ii) segmenting all or some of the source structures into structurally homologous segments, each of the structurally homologous segments being defined by two locations of the locations of highest structural conservation, so as to obtain a plurality of groups of structurally homologous segments, each of the groups being defined by the two locations of highest structural conservation;

(iii) selecting a template structure having the common structural framework and having specific positions corresponding to the locations of highest structural conservation;

for each of the segment groups:

(iv) splitting at least one structurally homologous segment of the structurally homologous segments at a site within the structurally homologous segment so as to obtain a split segment;

(v) superimposing respective positions of the split segment onto corresponding positions of the specific positions corresponding to the locations and displacing a corresponding segment in the template structure (vi) weight fitting the split segment for segment closure so as to obtain a weight fitted and reclosed segment in the template structure (vii) optionally repeating steps (iv)-(vi), while splitting at a different site or aborting further manipulation of the structurally homologous segment;

(viii) repeating steps (iv)-(vii) for at least one additional structurally homologous segment, so as to obtain at least one additional weight fitted and reclosed segment corresponding to each of the groups; and (ix) combinatorially using a plurality of the weight fitted and reclosed segments corresponding to each of the groups for reconstructing a plurality of reconstructed structures, each of the reconstructed structures having the common structural fold having conserved structural regions defining the structural framework and the diverse structural regions and positions corresponding to the locations of highest structural conservation;

thereby computationally constructing the library of amino-acid sequences having the common structural fold.

According to some embodiments of the invention, further includes, optionally defining in the plurality of source structures terminal segments, each of the terminal segments being defined by one location of the locations of highest structural conservation and a terminal location of the common structural fold, so as to define the terminal segments; and regarding at least one of the terminal segments as a split segment in step (v).

According to some embodiments of the invention, the splitting site is in a diverse structural region.

According to some embodiments of the invention, the splitting site is selected randomly.

According to some embodiments of the invention, the method further comprises, prior to step (ix), sorting each the weight fitted and reclosed segment corresponding to each of the groups into at least one structural cluster, and selecting a representative weight fitted and reclosed segment for the structural cluster, whereby each the weight fitted and reclosed segment of step (ix) is the representative weight fitted and reclosed segment.

According to some embodiments of the invention, sorting is conducted by a segment length.

According to some embodiments of the invention, sorting is further conducted by a root mean squared deviation of aligned polypeptide backbone positions.

According to an aspect of some embodiments of the present invention there is provided a method of designing and selecting an amino-acid sequence having a desired affinity to a molecular surface of interest of a molecular entity, the method comprising computationally constructing a library of amino-acid sequences having a common structural fold according to methods as presented herein, and further comprising:

(x) matching at least one of the reconstructed structures onto the molecular surface of interest, so as to design a plurality of reconstructed structures-molecular surface complexes each having a matching score, and optionally repeating step (x) for the reconstructed structure in the complex;

(xi) optionally substituting at least one of the weight fitted reclosed segment in the reconstructed structure of at least one of the complexes with another corresponding weight fitted reclosed segment and repeating step (x) so as to design a substituted-reconstructed structure-molecular surface complex having a matching score; and (xii) based on the matching score, selecting the amino-acid sequence having the desired affinity to the molecular surface of interest of the molecular entity.

According to an aspect of some embodiments of the present invention there is provided a method of producing an amino-acid sequence having a desired affinity to a molecular surface of interest, the method comprising:

designing and selecting the amino-acid sequence having the desired affinity to the molecular surface of interest according to a method as presented herein, in any one of the embodiments thereof; and expressing the amino-acid sequence in an expression system, thereby producing the amino-acid sequence having the desired affinity to the molecular surface of interest.

According to an aspect of some embodiments of the present invention there is provided an amino acid sequence having a desired affinity to a molecular surface of interest produced by a method as presented herein, in any one of the embodiments thereof.

According to some embodiments of any embodiment and aspect of the invention, the positions used in any of the methods presented herein are positions on a polypeptide backbone positions.

According to some embodiments of any embodiment and aspect of the invention, the polypeptide backbone positions are selected from the group consisting of an atom and a predefined position between atoms.

According to some embodiments of any embodiment and aspect of the invention, the atom is selected from the group consisting of an alpha carbon, a backbone carbonyl carbon, a backbone carbonyl oxygen and a backbone nitrogen.

According to some embodiments of any embodiment and aspect of the invention, weight fitting includes at least one operation selected from the group consisting of modulation of backbone dihedral angles, amino acid side-chain packing and change of amino acids.

According to some embodiments of any embodiment and aspect of the invention, modulation of backbone dihedral angles of the split segment is constrained by at least one dihedral angle of the structurally homologous segment corresponding to the split segment.

According to some embodiments of any embodiment and aspect of the invention, the change of amino acids is effected for amino acids of the split segment, and for amino acids in the template structure being at least partly inside a shell surrounding the split segment.

According to some embodiments of any embodiment and aspect of the invention, the change of amino acids is dictated by rules.

According to some embodiments of any embodiment and aspect of the invention, the rules comprise a position-specific scoring matrix.

According to some embodiments of any embodiment and aspect of the invention, the matching procedure includes at least one operation selected from the group consisting of rigid body orientation, modulation of backbone dihedral angles, amino acid side-chain packing and change of amino acids.

According to some embodiments of any embodiment and aspect of the invention, the rigid body orientation is effected by a reduced representation docking operation and/or a complete representation docking operation.

According to some embodiments of any embodiment and aspect of the invention, the change of amino acids is effected for amino acids of another corresponding fitted reclosed segment, and for amino acids in the template structure being at least partly inside a shell surrounding the another corresponding fitted reclosed segment.

According to some embodiments of any embodiment and aspect of the invention, the matching score is selected from the group consisting of binding energy, buried surface area, shape complementary and any combination thereof.

According to some embodiments of any embodiment and aspect of the invention, the method further includes a fold stability scoring, and selecting a structure in step (xii) is also based on the fold stability scoring.

According to some embodiments of any embodiment and aspect of the invention, the common structural fold is of an antibody.

According to some embodiments of any embodiment and aspect of the invention, the common structural fold is selected from the group consisting of an immunoglobulin or a part thereof, Ankyrin Repeat, Armadillo Repeat, Beta Grasp, Beta Trefoil, Greek Key, Jellyroll, Keyroll, Plait, Rossmann fold, Tetratrico peptide Repeat and TIM Barrel.

According to an aspect of some embodiments of the present invention there is provided a method of predicting a structure of a target protein having an amino-acid sequence, comprising:

(i) providing a plurality of source structures having the common structural fold and an amino-acid sequence identical in length to that of the target protein, the common structural fold having conserved structural regions defining a structural framework and diverse structural regions, the structural framework having locations of highest structural conservation;

(ii) replacing the amino-acid sequence of each of the plurality of source structures with the amino-acid sequence of the target protein, and segmenting structures of the plurality of source structures into structurally homologous segments, each of the structurally homologous segments being defined by two locations of the locations of highest structural conservation, so as to obtain a plurality of groups of structurally homologous segments, each the groups being defined by two locations of the locations of highest structural conservation;

(iii) selecting a template structure having the common structural framework and having specific positions corresponding to the locations;

for each of the groups:

(iv) splitting at least one structurally homologous segment of the structurally homologous segments at a site within the structurally homologous segment so as to obtain a split segment;

(v) superimposing respective positions of the split segment onto corresponding positions of the specific positions corresponding to the locations and displacing a corresponding segment in the template structure;

(vi) weight fitting the split segment for segment closure so as to obtain a weight fitted and reclosed segment in the template structure while maintain the amino-acid sequence of the target protein;

(vii) optionally repeating steps (iv)-(vi), while splitting at a different site or aborting further manipulation of the structurally homologous segment;

(viii) repeating steps (iv)-(vii) for at least one additional structurally homologous segment, so as to obtain at least one additional weight fitted and reclosed segment corresponding to each of the groups;

(ix) combinatorially using a plurality of the weight fitted and reclosed segments corresponding to each of the groups for reconstructing a plurality of reconstructed structures, each of the reconstructed structures having the common structural fold having conserved structural regions defining the structural framework and the diverse structural regions and positions corresponding to the locations of highest structural conservation; and (x) calculating an energy score for each of the reconstructed structures, wherein the structure of the target protein is having a low energy score.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 6A-D present curve plots showing the energy and structure criteria used to filter designed antibody structures in the final steps of the method presented herein, wherein the designed antibodies are filtered based to four parameters: predicted binding energy (FIG. 6A), buried surface area (FIG. 6B), shape complementarity between antibody structure and ligand (FIG. 6C), and packing quality between the variable light and heavy domain domains and the ligand (FIG. 6D), whereas the cutoff values are represented by dashed lines and derived from a set of 303 natural protein binding antibodies, while antibody designs (black curve) that passed all filters are compared with the natural protein-binding antibodies (gray curve);

FIG. 7 presents a scatter plot of yeast surface display with cells stained for expression levels and binding, wherein the template structure denoted "4m5.3" is marked by grey scatter dots and the designed structure denoted "Design #1" (SEQ ID NO. 1) is marked by black scatter dots;

FIGS. 8A-B present titration curves of anti-ACP design before and after introduction of point mutations (Design #1-5; SEQ ID NOs. 1-5, FIG. 8A) and the titration curves of anti-ACP design (Design #1 SEQ ID NO. 1) with its designed substrate ACP (marked by circles in FIG. 8B) and negative controls (TEM, marked by squares in FIG. 8B); and FIG. 9 presents sequence alignment of five TIM-barrel fold designs (SEQ ID NOs. 8-12), with designed altered substrate specificity, compared with the sequence of the original enzyme which served as the design template (lactonase from *Sulfolobus solfataricus*; SEQ ID NO. 13).

DESCRIPTION OF SPECIFIC EMBODIMENTS OF THE INVENTION

Figure 1:
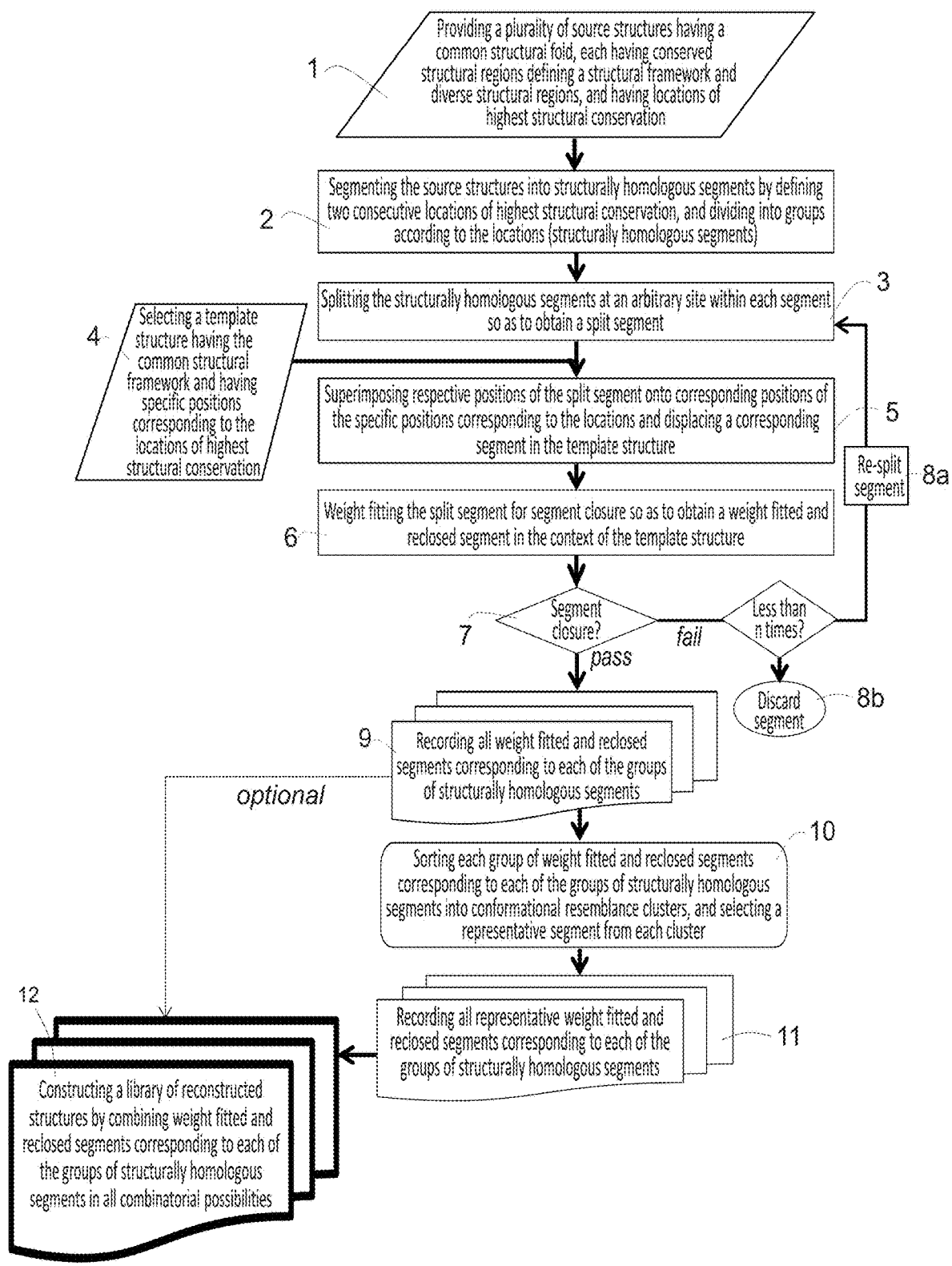
FIG. 1 is a schematic flowchart illustration of an exemplary algorithm for executing the method of computationally constructing a library of amino-acid sequences having a common structural fold, according to some embodiments of the present invention.

The present invention, in some embodiments thereof, relates to computational chemistry and computational protein design and, more particularly, but not exclusively, to a method of computationally constructing a library of amino-acid sequences having a common structural fold; and a method of designing and selecting an amino-acid sequence having a desired affinity to a molecular surface of interest of a molecular entity. These methods can be used, for example, for designing binding proteins having structural stability and high binding affinity towards predetermined molecular targets, or to de novo designed enzymes with de novo functions. The present invention, in some embodiments thereof, further relates to computational chemistry and, more particularly, but not exclusively, to a method of producing an amino-acid sequence having a desired affinity to a molecular surface of interest and to an amino acid sequence having a desired affinity to a molecular surface of interest.

The principles and operation of the embodiments of the present invention may be better understood with reference to the examples and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed hereinabove, previous methods for de novo design of antibodies relied on known canonical conformations, and then docked and designed to bind the target epitope by permutations of amino acid sequences at the epitope binding site, mainly the regions known as CDRs. While such computational methods may provide antibody structures which exhibit high affinity to the target in silico, these methods fail to address the issue of antibody stability, which is influenced by contributions of the entire backbone of the antibody and be sensitive to minute and subtle differences in backbone conformation as well as amino acid sequence throughout the backbone.

It can be reasoned that a key to solving the challenge of designing large and polar binding surfaces lies with the design of the protein backbone, since the backbone provides many additional conformational degrees of freedom that have so far been untapped by binder-design strategies. Designing backbones for function (e.g., stability and binding), however, is an unsolved problem due to the complication inherent in correctly balancing the contributions to free energy from polar groups and due to the large conformation space open to the protein backbone.

It is evident that at the current computational resources, the feat of defining the entire conformational combinatorial space multiplied by sequence permutation space, even if down-scaled by canonical conformations and amino acid sequence permutation limitations set at the gene level, and then attempting to rate each of the inhabitants of that space according to binding affinity, is impractical if not impossible. Furthermore, even if a method that can theoretically encompass and effectively and systematically sample all the conformational combinatorial space that can be generated by permutations at the gene level was made practical, such method would not be able to account for the myriad of random mutations which are observed or could occur in antibodies.

While conceiving the present invention, the inventors have contemplated an approach of sampling backbone conformations and sequence information from all natural folds (e.g., antibodies), including highly homologous ones, for which a set of three dimensional atomic coordinates, i.e., 3D structure, is available, in order to base the design on structures that have evolved over millennia and thereby improve the design of the folds (e.g., antibodies) with high binding affinity and high structural stability.

The underlying assumption for this approach is that nature has the advantages of evolutionary time scales and testing grounds to sample and select for the most effective scaffolds that outweigh even the most ambitious brute force computational technique currently feasible. Further still, relying on naturally occurring structures would use not only the predictable scaffolds and sequences, but also the unpredictable random mutations that occur in natural antibodies.

While reducing the present invention to practice and by way of exemplification, the inventors have developed a method that relies on the modular structure of naturally occurring immune-system antibodies to construct de novo molecular binders, and have tested this method using benchmark recapitulation tests whose results show that this method is capable of arriving at structures that resemble naturally occurring structures and improves all binding and structural parameters compared to structures that have been constructed using previous design methods. The presently disclosed method has been applied and validated on a diverse set of naturally occurring, high-affinity antibody-bound complexes having a known three-dimensional structure, by removing all sequence and backbone-conformation information from the members of the set, and recapitulating their natural binding modes, natural backbone conformations and sequences, especially in cases where the natural binding surface is large.

The present inventors have further envisioned that this method can be implemented to design molecular binding proteins which are members of families of structurally similar proteins (FSSP), namely proteins that belong to families exhibiting, at least in parts thereof, one or more naturally reoccurring, hence, conserved, folds such as, but not limited to, antibodies and domains thereof, alpha/beta hydrolases, TIM barrel proteins and the likes.

According to some embodiments of the present invention, the method provided herein is useful for designing highly stable proteins that can bind at high affinity, in principle, any target molecule at any given conformation. In the exemplary case of antibodies, the method exploits the observation that the backbones of hypervariable fragments are often interchangeable with one another to generate new backbone-fragment combinations, for a theoretical total complexity on the order of $10^{13}$; thus, the method uses backbone conformations, encoded by the V(D)J gene segments of the antibody variable domain, which are combined with one another to create a highly diverse set of antibody scaffolds. This pre-computation step creates an unprecedented combinatorial space of backbones and large sequence datasets that are predicted to be stable and have high-affinity for their targets. The scaffolds are then docked against the target molecule. The designed antibody is refined by an iterative process that replaces backbone conformation fragments with ones observed in natural antibodies, and designs the amino acid sequence for optimal binding and antibody stability. Throughout the design process, according to some embodiments of the present invention, sequence constraints derived for each conformation segment are used to enforce sequence-structure rules. Finally, models are selected by energy and conformation criteria derived from a set of natural antibody-bound complexes.

The protein design method presented herein, when applied to antibodies, addresses several related challenges, including:

1. Incorporating knowledge from conformation and sequence databases to constrain design choices;

2. Encoding long-range residue correlations between the variable segments, which largely lack stabilizing secondary-structure elements, and the framework, which forms a tightly packed and stable structural foundation;

3. Efficient sampling of the large backbone and sequence combinatorial space of antibodies; and 4. Designing antibody conformations and sequences that optimize both antibody stability and target-molecule binding. In the following sections different elements of the algorithm are described, as well as how they address current design challenges.

A Method of Computationally Constructing a Library of Amino-Acid Sequences Having a Common Structural Fold:

Hence, according to an aspect of some embodiments of the present invention, there is provided a method of computationally constructing a library of amino-acid sequences having a common structural fold, which is executed according to steps described below. The library, according to some embodiments of the present invention, is designed to sample effectively and concisely the vast conformational space occupied by the members of the family of naturally occurring proteins sharing this common structural fold, and can therefore be used to provide a basis for a de novo protein design as described hereinbelow.

FIG. 1 presents a schematic flowchart illustration of an exemplary algorithm for executing the method of computationally constructing a library of amino-acid sequences having a common structural fold, according to some embodiments of the present invention. The description following below refers to some of the operations in the algorithm presented in FIG. 1. As will be understood from the description below, some of the operations in the algorithm can be executed in alternative order and alternative number of cycles.

According to some embodiments of the present invention, the method comprises, in step (i) thereof, providing a plurality of source structures having the common structural fold (Box 1 in FIG. 1).

In the context of embodiments of the present invention, the term "source structures" refers to a collection of experimentally elucidated 3D structures of proteins which share a common polypeptide backbone fold in at least one domain thereof, regardless of their sequence homology to one another in that domain. In general, the collection of source structures can be formed from some or all experimentally elucidated protein structures. Alternatively, the source structures may include a subset of all available 3D structures, or even a small part thereof. Hence, according to some embodiments of the present invention, the number of source structures is more than 500, more than 100, more than 50, more than 10, more than 5, or more than 2.

According to some embodiments of the invention, a common structural fold is characterized by having conserved structural regions defining structural framework regions and diverse structural regions, wherein the structural framework regions typically exhibit high structural conservation, while typically some locations in the structural framework regions exhibit the highest structural conservation. These locations are referred to herein as "locations of highest structural conservation". Structural conservation can be conceptualized via FIG. 2.

Figure 2:
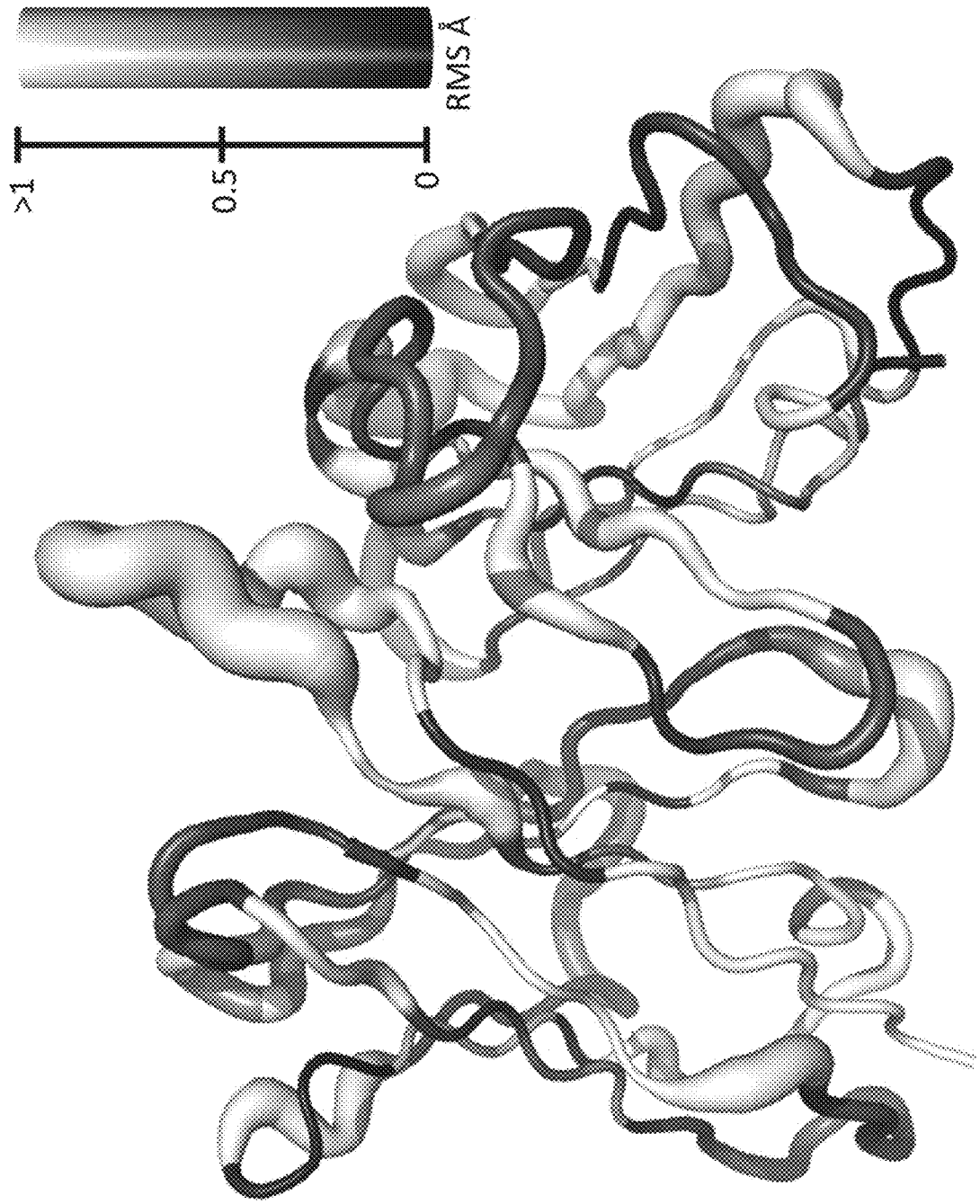
FIG. 2 presents an illustration of the variation in structural similarity of backbone atoms positions, showing a trace of the backbone as a tube of varying thickness and shade, corresponding to the variations in backbone atoms positions in the 3D structures of a group of protein which are members of a family of structurally similar proteins, wherein the structures are superimposed on one-another so as to afford an optimal overall structural fit (scale showing RMSD in Cα atom positions ranging from 0 Å (white) to 1 Å (black))

FIG. 2 presents an illustration of the variation in structural similarity of backbone atoms positions, showing a trace of the backbone as a tube of varying thickness and shade, corresponding to the variations in backbone atoms positions in the 3D structures of a group of protein (e.g., 40 non-redundant antibody Fv structures in this exemplary illustration) which are members of a family of structurally similar proteins (FSSP), wherein the structures are superimposed on one-another so as to afford an optimal overall structural fit (scale showing RMSD in Cα atom positions ranging from 0 Å (white) to 1 Å (black)).

As can be seen in FIG. 2, some regions along the backbone of most structures diverge in their 3D structure, filling a thicker envelope around an average path, while other regions fill a tighter, thinner envelope around the average path. In a collection of source structures, according to some embodiments of the present invention, the "thinner" regions are said to exhibit a high structural conservation. Typically, the thinner regions correspond to structural framework regions and the thicker regions correspond to diverse structural regions.

According to some embodiments of the present invention, the thinnest locations along the collection of superimposed polypeptide backbone chains are referred to herein as "locations of highest structural conservation". The terms "thin" and "thick", stemming from the graphical illustration presented in FIG. 1, can also be expressed in terms of root mean squared deviation (RMSD) of a plurality of aligned polypeptide backbone positions, typically given in Ångström (Å) units, wherein "thin" has a relatively small value compared to "thick". When referring to a specific structure in the plurality of superimposed structures, a location of highest structural conservation corresponds to a specific position, and vice versa, a specific position of highest structural conservation corresponds to a location of highest structural conservation.

According to some embodiments of the present invention, the selection of the source structures and/or the selection of segments, may be carried out while imposing a selection criteria so as to bias the outcome of the methods to afford sequences that are more likely to resemble a exhibit one or more traits. The selection criteria can be based on the source organism (to ensure, for example, compatibility with an expression system or a desired final host), amino-acid sequence length (entirely or per segment or loop length, etc.]. Such use of a selection criterion, based on a specific enzymatic activity of the source structures, is demonstrated in Example 5, where bias was applied to select blade 7 conformations that are of PTE enzyme homologue source in construction of the conformation library.

According to some embodiments of the present invention, a "position" in the polypeptide backbone is represented by a backbone atom or a predefined position between backbone atoms, wherein the backbone atom is typically an alpha carbon atom, a backbone carbonyl carbon atom, a backbone carbonyl oxygen atom or a backbone nitrogen atom.

According to embodiments of the present invention, the source structures are used to construct a backbone conformation database, populated by a plurality of polypeptide chain segments. Without being bound by any particular theory, it is assumed that the stability of a protein conformation relies on both positive and negative design elements. A key advantage of computational design of proteins belonging to a very diverse family sharing a common fold, is that one can extract statistics regarding amino acid choices on a per-position basis that encodes at least some of these elements to guide the design process. Moreover, by correlating natural backbone conformation and sequences it is possible to classify sets of natural segment sequences that fold into particular conformation classes.

According to embodiments of the present invention, the segmentation of the polypeptide chain involves regions constituting the domain on which the recognition and binding takes place. According to embodiments of the present invention, the method is based on structural alignments of experimentally determined 3D structures and segmentation of the polypeptide chain based on consideration of structurally conserved regions (hence, segmentation to structurally homologous segments). That is different than previously known computational methods, which are based on amino-acid sequence homology alignments and segmentation of the polypeptide chain based on consideration of conserved regions.

Thus, according to some embodiments of the present invention, the method comprises, in step (ii) thereof, segmenting each of the structures of the source structures into structurally homologous segments, each of which is defined by two locations of highest structural conservation, so as to obtain a plurality of groups of structurally homologous segments. Each of the groups of structurally homologous segments is therefore defined by the two locations of highest structural conservation (Box 2 in FIG. 1).

Optionally, the segmentation further includes one or more terminal segments, which include the ends of the polypeptide chain (termini or tails) of each of the structures, wherein a polypeptide chain terminus is referred to herein as "terminal location". Each of the groups of terminal segments, also referred to herein as tail segments, is therefore defined by one location of highest structural conservation and one terminal location. It is noted that the terminal locations do not necessarily share high structural homology.

Hence, in the context of embodiments of the present invention, the term "segment" refers to a continuous section of the polypeptide chain of any one of the source structures, which starts and ends at or near two locations. A "structurally homologous segment" is defined as a segment which starts and ends at or near two locations of highest structural conservation. A "terminal segment" is defined as a segment that starts/ends at or near one location of highest structural conservation and ends/starts at one terminal location.

In the context of step (ii), according to some embodiments of any of the embodiments of the present invention, the polypeptide chain of each of the source structures is segmented into "structurally homologous segments". Optionally, in the context of step (ii), according to some embodiments of any of the embodiments of the present invention, the polypeptide chain of each of the source structures is segmented into "structurally homologous segments", and is further segmented into "terminal segments".

An exemplary use of the provided methods, according to some embodiments of the present invention, has been applied to design a de novo Fv fragment of an antibody, and demonstrated a benchmark recapitulation experiment in the Examples section that follows. In these exemplary embodiments, only Fv domains having a light κ chain have been included in the collection of source antibodies (i.e., the source structures). Specifically, 788 variable light κ chains and 785 variable heavy-chain structures were used as source antibodies in the benchmark recapitulation experiment for testing the results obtained by the method presented herein.

In the exemplary demonstration of the methods presented herein using antibodies, the source antibodies include the binding domain which is the Fv domain and each of the two chains that constitute the Fv domain of all source antibodies, namely each of the light chain and the heavy chain, were segmented into two structurally homologous segments by identifying two consecutive locations of highest structural conservation; for example, the two cysteine residues of the variable domain which forms the structurally conserved intra-chain disulfide bond, and a third structurally conserved position which is close to the second cysteine, thereby forming four structurally homologous segments for each Fv domain.

Specifically, in the exemplary demonstration of the methods presented herein, according to some embodiments of the invention, demonstrated for Fv of antibodies in the Examples section that follows, the segmentation follows a division into four segments: L1-L2 (referred to as "$V_L$") and H1-H2 (referred to as "$V_H$"), each spanning all amino acids between the two structurally conserved cysteine residues of the light and heavy variable domains, L3 and H3, each starting at the first amino acid after the second cysteine and ending at position 100 of the variable light κ domain and position 103 of the variable heavy domain, using the Chothia position numbering scheme (see, Table 2 below).

According to some embodiments of the present invention, the construction of the backbone conformation database involves bringing all segments into a unified relative coordinates system. According to some embodiments of the present invention, the method comprises, in step (iii) thereof, selecting a template structure having the same common structural framework as of the source structures, and therefore having specific positions corresponding to the locations of highest structural conservation, and bringing all structurally homologous segments into the coordinates system of the template structure (Box 4 in FIG. 1).

In some of any of the embodiments of the present invention, the template structure is selected arbitrarily and/or randomly from the source structures. According to some embodiments of the present invention, the template structure serves for grafting thereto the structurally homologous segments from the source structures. According to some embodiments of the present invention, during the de novo protein design the template structure is used as the reference structure to which the designed protein is compared using some structural features as references.

According to some embodiments of the present invention, all structurally homologous segments are brought to share common start and end points, since some of the structurally homologous segments may have a different conformation and oftentimes a different length. Alternatively, all structures are structurally aligned based on spatial alignment of some or all locations of highest structural conservation.

According to some of these embodiments, the following procedure is carried out, according to some embodiments of the present invention, to bring all structurally homologous segments to share a common start and end points, and optionally further share the locations of highest structural conservation of one, some or all of the terminal segments:

According to some embodiments of the present invention, the method comprises, in step (iv) thereof, splitting at least one structurally homologous segment at a site therein so as to obtain a split segment (Box 3 in FIG. 1);

Optionally, if the method further includes one or more terminal segments, the terminal segment is not split, but rather the terminal segment enters the procedure as a split segment, while all other steps in the procedure apply as presented herein, namely a terminal segment is regarded as a split segment in step (v);

According to some embodiments of the present invention, the method comprises, in step (v) thereof, for each of the groups of structurally homologous segments, superimposing the respective positions of highest structural conservation of the split segment onto the corresponding specific positions of the template structure, and displacing the corresponding segment from the template structure (Box 5 in FIG. 1);

And according to some embodiments of the present invention, the method comprises, in step (vi) thereof, weight fitting the split segment in order to achieve segment closure while allowing the main chain of the segment to form a chemically sound conformation with little or no internal strain, and thereby obtain a weight fitted and reclosed segment in the template structure (Box 6 in FIG. 1). For terminal segments, weight fitting does not include closure.

The term "weight fitting", according to some embodiments of any of the embodiment of the present invention, refers to a one or more computational structure refinement procedures or operations, aimed at optimizing geometrical, spatial and/or energy criteria by minimizing polynomial functions based on predetermined weights, restraints and constrains (constants) pertaining to, for example, sequence homology scores, backbone dihedral angles and/or atomic positions (variables) of the refined structure. According to some embodiments, a weight fitting procedure includes one or more of a modulation of backbone dihedral angles, change to the length of the fitted segment (either increase or decrease), an amino acid side-chain packing and a change of amino acid sequence, whereas the terms "modulation of backbone dihedral angles", "amino acid side-chain packing" and "change of amino acid sequence" are also used herein to refer to, inter alia, well known optimization procedures and operations which are widely used in the field of computational chemistry and biology. For a review of general optimization approaches, see for example, "Encyclopedia of Optimization" by Christodoulos A. Floudas and Panos M. Pardalos, Springer Pub., 2008. An exemplary optimization procedure, according to some embodiments of the present invention, is the cyclic-coordinate descent (CCD), discussed hereinbelow, which is used herein with the default all-atom energy function implemented in the Rosetta software suite for macromolecular modeling.

In some embodiments of the present invention, the restraints and constrains (weights) in a weight fitting are considered the rules that dictate the computational procedures. For example, when refining the backbone atomic positions and dihedral angles of any given polypeptide segment having a first conformation, so as to drive towards a different second conformation while attempting to preserve the dihedral angles observed in the second conformation as much as possible, the computational procedure would use harmonic restraints that bias, e.g., the Ca positions, and harmonic restraints that bias the backbone-dihedral angles from departing freely from those observed in the second conformation, hence allowing the minimal conformational change to take place per each structural determinant while driving the overall backbone to change into the second conformation.

Constrains can also be applied in a procedure that changes the amino acid sequence of a protein. These constraints may also be used to preserve, at least to some extent, some parts of the sequence which is inherited from a predecessor sequence. One of the most common constraints employed to amino acid sequence alterations stem (locations) from highly conserved sequence patterns at specific positions, which are typically exhibited in FSSP. According to some embodiments of the present invention, the rules by which a change of amino acids is dictated during a weight fitting process include position-specific scoring matrix values, or PSSMs.

A "position-specific scoring matrix" (PSSM), also known in the art as position weight matrix (PWM), or a position-specific weight matrix (PSWM), is a commonly used representation of recurring patterns in biological sequences, based on the frequency of appearance of a character (monomer; amino acid; nucleic acid etc.) in a given position along the sequence. PSSMs are often derived from a set of aligned sequences that are thought to be structurally and functionally related and have become widely used in many software tools for computational motif discovery. In the context of amino acid sequences, a PSSM is a type of scoring matrix used in protein BLAST searches in which amino acid substitution scores are given separately for each position in a protein multiple sequence alignment. Thus, a Tyr-Trp substitution at position A of an alignment may receive a very different score than the same substitution at position B, subject to different levels of amino acid conservation at the two positions. This is in contrast to position-independent matrices such as the PAM and BLOSUM matrices, in which the Tyr-Trp substitution receives the same score no matter at what position it occurs. PSSM scores are generally shown as positive or negative integers. Positive scores indicate that the given amino acid substitution occurs more frequently in the alignment than expected by chance, while negative scores indicate that the substitution occurs less frequently than expected. Large positive scores often indicate critical functional residues, which may be active site residues or residues required for other intermolecular or intramolecular interactions. PSSMs can be created using Position-Specific Iterative Basic Local Alignment Search Tool (PSI-BLAST), which finds similar protein sequences to a query sequence, and then constructs a PSSM from the resulting alignment. Alternatively, PSSMs can be retrieved from the National Center for Biotechnology Information Conserved Domains Database (NCBI CDD) database, since each conserved domain is represented by a PSSM that encodes the observed substitutions in the seed alignments. These CD records can be found either by text searching in Entrez Conserved Domains or by using Reverse Position-Specific BLAST (RPS-BLAST), also known as CD-Search, to locate these domains on an input protein sequence.

As discussed hereinabove, PSSM scores are used in the method presented herein during various weight fitting and other refinement and design calculations in two ways, according to some embodiments of the present invention. First, design sequence choices are restricted only to identities above a certain conservation threshold according to the PSSM. The cutoffs are determined separately for the binding surface (exemplary PSSM score greater or equal to 0 for all protein residues with Cβ's within a 10 Å distance cut-off of the molecular surface of interest of a molecular entity), diverse structural regions (greater or equal to 1), and structural framework regions, locations and positions (greater or equal to 2); effectively, positions that are associated with binding are allowed more freedom to vary from the consensus than positions in the core of the protein and its framework. Second, the all-atom energy function used in sequence design is modified to include a term that biases the sequence towards the more likely identities according to the PSSM, and also in these cases, the bias towards the sequence consensus is stronger away from the binding site.

According to some embodiments of the present invention, a structurally homologous segment is split into two sub-segments, each of which is grafted on specific positions in a template structure corresponding to respective positions of the split segment, while replacing the corresponding segment in the template structure, and thereafter the split and superimposed segment undergoes weight fitting in the context of the template structure.

The weight fitting includes refining the backbone dihedral angles of the split segment having a first conformation so as to drive it towards closure, which means it will then have a slightly different conformation. As stated hereinabove, weight fitting does not include closure in the case of terminal segments. The weight fitting process attempts to preserve the original dihedral angles as much as possible, hence the computational procedure constrains the variability of the dihedral angles to those observed in the source structure, thereby allowing the minimal change to take place per each dihedral angle while driving the split segment to closure, thereby obtaining a weight fitted and reclosed segment in the context of the template structure. This process is effected iteratively while changing the amino acid sequence of the split segment subject to PSSM-derived constraints. Changes in the amino acid sequence allow small changes in the backbone conformation to take place by allowing amino acid side-chain packing to be optimized together with the backbone dihedral angles.

According to some embodiments of the present invention, the weight fitting process also changes amino acids in the designed structure, which are at least partly present inside a shell surrounding the split segment. According to some embodiments, the shell is characterized by a radius of 2 Å to 20 Å, or alternatively a radius of 2 Å, 3 Å, 4 Å, 5 Å, 6 Å, 7 Å, 8 Å, 9 Å, 10 Å, 11 Å, 12 Å, 15 Å or 20 Å. According to some embodiments, the shell radius is 6 Å.

Following is a brief description of an exemplary weight fitting process, according to some embodiments of the present invention, which is non-limiting with regards to the definition of "weight fitting" in the context of the present invention. Structurally homologous segments are sorted by length, and for each length sub-group of each group of structurally homologous segments, backbone dihedral angles (Φ, Ψ and Ω) are extracted from the source structures ("original" backbone conformation), and replace those in the corresponding segment in the template structure with the source dihedral angles, while introducing a main-chain split site in a randomly chosen position of the grafted segment. It is noted that a main-chain split is not introduced in terminal segments. In other words, the segments from all non-template structure are cut at an arbitrary position away from the structural framework regions and away from the positions of highest structural conservation (the ends of the segment), placed on the template structure instead of the corresponding segment in the template structure, by superimposing the corresponding positions, and then the dihedral angles of the two parts of the split segment are allowed to shift incrementally according to constraints, while simultaneously changing the amino acid sequence of the segment, subject to PSSM-derived constraints, as described herein. Terminal segments are placed onto the template structure by superimposing the conserved position replacing the corresponding terminal segment on the template structure.

According to some embodiments, each of the split and grafted segments is weight fitted onto the template structure using cyclic-coordinate descent (CCD), followed by small, and shear moves, as implemented, for example, in the "CCD mover" implemented in the Rosetta software suite. Terminal segments are weight fitted onto the template structure using only small and shear moves, implemented in the Rosetta software suit using a script such as the "TailSegmentMover" script presented in the Examples section that follows below. During refinement, the standard all-atom energy function, which is dominated by van der Waals packing, hydrogen bonding and implicit solvation, is modified by the addition of a harmonic term favoring the closing of the main-chain split site, and harmonic restraints that bias the Cα positions, penalizing differences in the main-chain Cα positions in the weight fitted segment relative to the original positions in the source structure, and an harmonic term for the backbone-dihedral angles, penalizing differences in the dihedral angles relative to the original angles observed in the source structure. Adjusting the segment conformation alternates backbone movements with combinatorial amino acid side-chain packing. During packing steps the procedure allows amino acid sequence changes in the entire modeled segment, and in a 6 Å shell surrounding the segment, subject to segment's PSSM-derived constraints. Each CCD step or TailSegment-Mover is repeated several hundreds of times, depending on the available computing power and other practical considerations, and at the end of each CCD procedure, the root mean square deviation (RMSD) of the modeled segment from the source segment is calculated, and if it exceeds 1 Å or if, for example, the main-chain gap score (an exemplary criteria for main chain continuity defined within the Rosetta software suite; this does not apply to terminal segments) at the split site is too large (e.g., greater or equal to 0.5), the procedure is repeated once more for that segment. If after several hundreds of times the score is still unacceptable, the procedure is re-run for another closure trial using a different arbitrarily and randomly chosen split site.

According to some embodiments of the present invention, the method comprises, in step (vii) thereof, optionally repeating steps (iv)-(vi) (Box 7 in FIG. 1), while splitting the segment at a different site (Box 8a in FIG. 1) or aborting further manipulation of this structurally homologous segment (Box 8b in FIG. 1).

Thus, segments that fail to close properly after a preselected number of weight fitting cycles (attempts at attaining closure) are discarded from further consideration (Box 8b in FIG. 1). It has been found that the weight fitting procedure is highly effective in adjusting a source segment backbone conformation in the context of the template structure. In the case presented in the Examples section below, this weighted fitting for segment closure procedure successfully closes segments of up to 74 amino acids long in no more than 6 split site attempts with an average number of iterations of 1.2.

According to some embodiments of the present invention, the method comprises, in step (viii) thereof, repeating steps (iv)-(vii) for at least one additional structurally homologous segment, so as to obtain at least one additional weight fitted and reclosed segment corresponding to each of the groups.

Once the split segment attains closure by a weight fitting procedure, it is referred to as a weight fitted and reclosed segment. According to some embodiments of the present invention, the new backbone dihedral angles thereof are recorded in a torsion database, which forms a part of the library.

The product of the abovementioned process is a collection of weight fitted and reclosed segments, which have been grafted on the template structure; hence, each segment from any group of segments can be combined with segments from all other groups of segments to form a complete reconstructed structure (Box 9 in FIG. 1).

According to some embodiments of the present invention, a structurally homologous segment is defined by two consecutive locations of highest structural conservation, while a terminal segment is defined by one terminal location and one location of highest structural conservation which may be the location of highest structural conservation nearest to the terminal location in the continuous polypeptide chain. In such embodiments, there is essentially no overlap of amino acids between the segments; namely no amino acid position is shared by two consecutive segments. In some embodiments, the two locations of highest structural conservation are selected to have some overlap of a number of amino acid residues, ranging from 1-20, 1-10 or 1-5 amino acid overlap between two consecutive segments, namely some amino acids near the ends of adjacent segments are shared by the two adjacent segments.

As discussed hereinabove, backbone-conformation sampling is computationally very demanding, and despite some success backbone redesign has led to conformations that deviated from the original computed models. By designing proteins in a conformationally highly diverse family, one can make use of naturally occurring conformation variants for each backbone segment, where the conformations are likely to be stable within the host protein fold. To make computationally efficient use of the richness of backbone conformations observed in natural proteins, the conformations of all structurally homologous, weight fitted and reclosed segments of the source structures are stored in a database for use during the protein design process.

According to some embodiments of the present invention, the method comprises, in step (ix) thereof, optionally using the weight fitted and reclosed segments, corresponding to each of the groups, for combinatorially reconstructing a plurality of reconstructed structures, each of which is having the common structural fold having conserved structural regions defining the structural framework and the diverse structural regions and positions corresponding to the locations of highest structural conservation. It is this plurality of reconstructed structures which is referred to herein as the library of amino-acid sequences having the common structural fold (Box 12 in FIG. 1). In this optional step, the library is exhaustive and comprises essentially all the possible combinations for combining all the weight fitted and reclosed segments generated in the previous steps of the method.

According to some embodiments of the present invention, the method can be used to generate variations only to a particular region in the structure of a given protein, by selecting a one or more particular segments that overlap with the region of interest. That is, rather than creating a plurality of reconstructed structures of all possible segment combinations, the method is used by choosing instead one or more segments of interest in a protein, to create a plurality of reconstructed structures which are varied in conformation only in the segments of interest. This mode of use of the method is exemplified in Example 4 (one segment) and Example 5 (4 segments) hereinbelow.

In order to streamline the computational load in executing the methods presented herein, a sampling and reduction procedure may be carried out, according to some embodiments of any embodiment of the present invention.

According to some embodiments of the present invention, the method of computationally constructing a library of amino-acid sequences having a common structural fold further comprises, prior to step (ix), sorting each of the weight fitted and reclosed segments corresponding to each of the groups of structurally homologous segments into at least one structural cluster (Box 10 in FIG. 1), and selecting a representative weight fitted and reclosed segment from the structural cluster, whereby each of the weight fitted and reclosed segment of step (ix) is the representative weight fitted and reclosed segment (Box 11 in FIG. 1).

According to some embodiments of the present invention, in this optional step of the method presented herein, which is also referred to herein as the "sampling and reduction procedure", the contents of each of the groups of structurally homologous segments is represented by a set of representative segments. These representative segments are then recombined into all permutations to form the library of amino-acid sequences having a common structural fold (Box 12 in FIG. 1).

According to some embodiments of the present invention, in the context of the method of computationally constructing a library of amino-acid sequences having a common structural fold, the term "sorting" refers to a procedure by which at least some of the weight fitted and reclosed segments in each of the groups of structurally homologous segments, are sorted by length. According to some embodiments of the invention, the term "sorting" further encompasses clustering the length-sorted weight fitted and reclosed segments by a root mean squared deviation (RMSD) of aligned polypeptide backbone positions.

According to some embodiments of the present invention, a PSSM is assigned for the entire reconstructed structure comprising the current sampled conformation segments, thereby synchronizing the sequence constraints with the currently sampled backbone conformation. This procedure is advantageous since during the weight fitting step, residues outside the weight fitted segment, within a 2-20 Å shell, may have also changed, thus the PSSM is made consistent with all of the conformation segments, including segments that were not subject to fitting at that step. These sequence-related PSSM constraints considerably reduce the combinatorial sequence-optimization problem.

Albeit reduced, a library produced by the method presented herein, may contain a number of reconstructed structures that exceeds the number of experimentally available structures having the same common structural fold; and furthermore, the reconstructed structures of the library are more diverse conformationally compared to experimentally available structures.

A Method of Designing and Selecting One or More Amino-Acid Sequences Having a Desired Affinity to a Molecular Surface of Interest:

The library of amino-acid sequences having a common structural fold, compiled according to the method presented herein, that comprises reconstructed structures which has been optimized to sample the conformational space of known structures, is used to test interactions with a molecular surface of interest of a molecular entity. The members of the library are further designed and assessed for affinity to the molecular surface of interest and further assessed for structural viability, using a method for designing and selecting qualified amino acid sequences designed for desired affinity to the molecular surface of interest and molecular stability.

According to another aspect of some embodiments of the present invention, there is provided a method of designing and selecting an amino-acid sequence having a desired affinity to a molecular surface of interest of a molecular entity.

Figure 3:
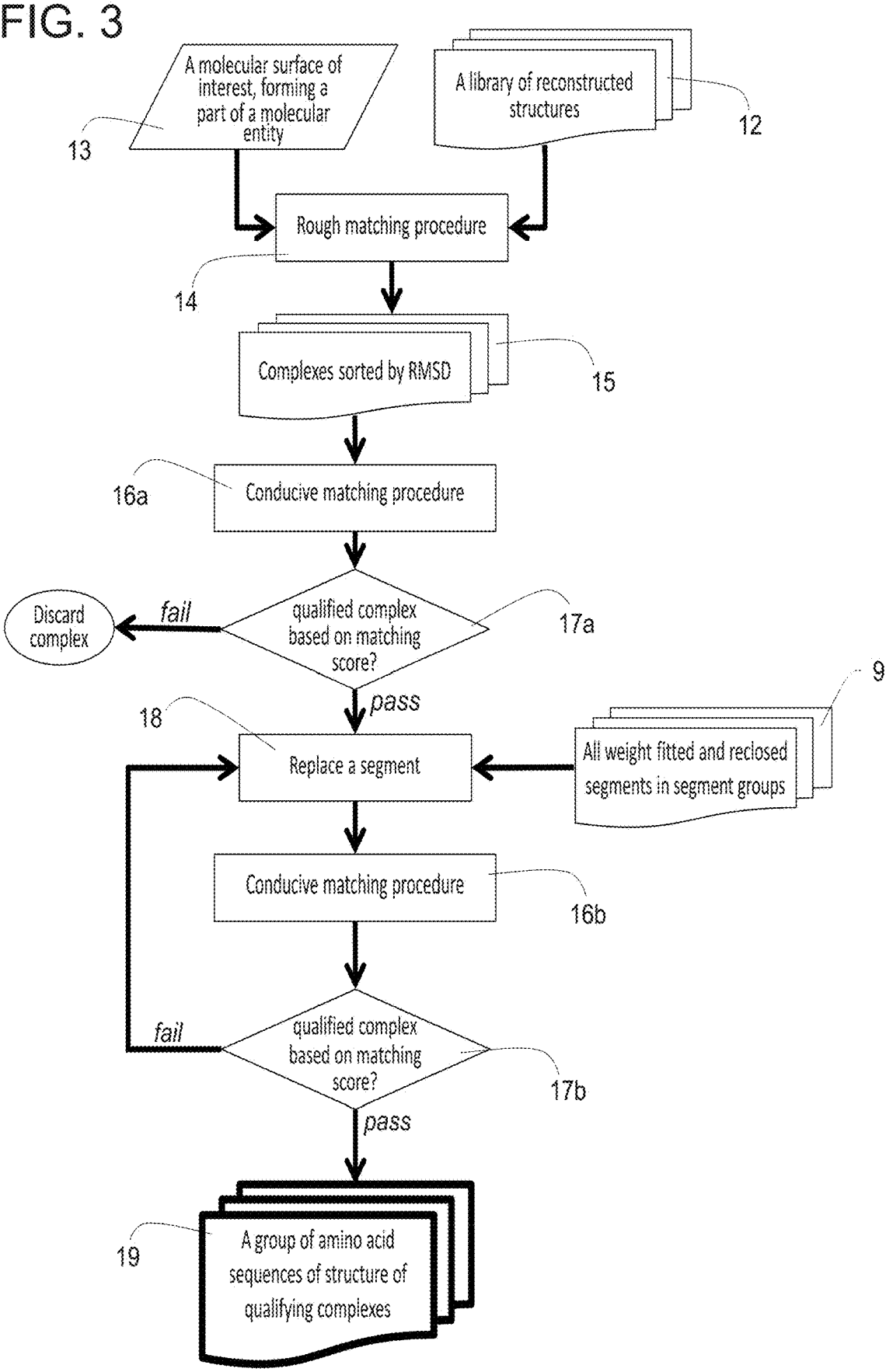
FIG. 3 is a schematic flowchart illustration of an exemplary algorithm for executing the method of designing and selecting an amino-acid sequence having a desired affinity to a molecular surface of interest of a molecular entity, according to some embodiments of the present invention.

FIG. 3 is a schematic flowchart illustration of an exemplary algorithm for executing the method of designing and selecting an amino-acid sequence having a desired affinity to a molecular surface of interest of a molecular entity, according to some embodiments of the present invention. The description following below refers to some of the operations in the algorithm presented in FIG. 3. As will be understood from the description below, some of the operations in the algorithm can be executed in alternative order and alternative number of cycles.

According to some embodiments of the present invention, the method comprises, in step (x) thereof, matching at least one of the reconstructed structures, forming the library presented hereinabove (Box 12 in FIG. 2), onto the molecular surface of interest (Box 13 in FIG. 2), so as to design a plurality of reconstructed structures-molecular surface complexes, each having a matching score. According to some embodiments, step (x) may further comprise an optional reiteration of step (x), using the complex resulting in a previous iteration.

As used herein in the context of embodiments of the present invention, the term "matching" refers to a procedure which includes a rigid body orientation optimization at any given grid resolution, also known as docking or surface complementarity rigid body orientation refinement, and may further include one or more additional operations, such as, without limitation, modulation (optimization) of backbone dihedral angles, amino acid side-chain packing optimization and a change of amino acids or sequence optimization.

According to some embodiments, the matching procedure includes the operation of rigid body orientation optimization defining any sub-set of atoms of the bodies, which optimizes the surface complementarity at the interface between the reconstructed structure and the molecular surface, treating each of the complex counterparts as rigid bodies. This rigid body surface complementarity optimization is performed at a predetermined atom sub-set, which can be a reduced set of atoms, representing the backbone and a virtual atom representing the centroid of the sidechain atoms (referred to herein as "reduced representation docking"), or a set of atoms representing the entire structure of both bodies (referred to herein as "complete representation docking").

According to some embodiments of the invention described herein, a matching procedure includes a reduced representation docking operation which searches for an optimal match the reconstructed structure to the molecular surface of interest, treating both as rigid bodies with invariant amino acid sequence (rigid body orientation refinement). Such matching procedure is referred to herein as a "rough matching procedure" (Box 14 in FIG. 2).

Alternatively, in some embodiments of the invention described herein, a matching procedure includes a rigid body orientation refinement based on a complete representation docking operation, and further includes structure optimization operations that include, without limitation, optimizing the amino acid sequence (sequence design), optimizing backbone and side-chain conformations and optimizing atomic position, essentially aimed at affording a structure with optimal structural complementarity with respect to the molecular surface of interest. Such matching procedure is referred to herein as a "conducive matching procedure".

Any one of the operations of the matching procedure may be conducted while using rules for the optimization, such as constraints and restraints discussed hereinabove, e.g., harmonic restraints on movements of atomic positions and PSSM values for change of amino acids. In addition, since some optimization operations alter the amino acid sequence of the reconstructed structure at various regions, a new set of sequence constraint rules (e.g., PSSM) may be reassigned to the entire resulting structure.

The rigid body orientation operation typically results in a plurality of reconstructed structures-molecular surface complexes being different from each other by the relative orientation between the reconstructed structure and the molecular surface of interest which forms a part of a chemical entity (Box 15 in FIG. 2).

According to some embodiments of the present invention, the matching procedure is a rough matching procedure, which includes a reduced representation docking operation. According to some embodiments, the resulting plurality of matched complexes resulting from a rough matching procedure may further be sorted into clusters of relative orientation similarity by RMSD (typically clustered by a range criteria denoted in Å), and a cluster representative complex is selected from each relative orientation cluster for further processing within the matching procedure step, namely another cycle of the matching procedure, such as a conducive matching procedure which may include other optimization operations.

According to some embodiments, a conducive matching procedure (another cycle of step (x)) is effected for select complex structures resulting in a rough matching procedure (Box 16a in FIG. 2).

According to some embodiments of the present invention, the conducive matching procedure may include a complete representation docking operation, which is effected in combination with other optimization operations, such as change of amino acids in the reconstructed structure of the current complex, which is referred to herein as "sequence design". The sequence design is typically dictated by rules, such as PSSM values, e.g., the reassigned PSSM value for the entire reconstructed structure. According to these embodiments, sequence design is carried out for the reconstructed structure amino acid residues which are present, according to some embodiments of the present invention:

at the interface between the reconstructed structure and the molecular surface of interest;

at regions of the reconstructed structure that fall within a shell surrounding the interface;

at regions of the reconstructed structure that fall within a shell surrounding a segment; and/or the entire reconstructed structure or any part(s) thereof.

According to some embodiments, the shell is characterized by a radius of 2 Å to 20 Å, or alternatively a radius of 2 Å, 3 Å, 4 Å, 5 Å, 6 Å, 7 Å, 8 Å, 9 Å, 10 Å, 11 Å, 12 Å, 15 Å or 20 Å. According to some embodiments, the shell radium is 6 Å.

According to some embodiments, the matching procedure further includes a matching assessment procedure, which produces one or more a matching scores for each of the optimized complexes resulting in the current cycle of the matching procedure.

The term "matching score" encompasses a variety of complex attributes assessments which include, without limitation, buried surface area (buried in the interface between the structure and the molecular surface of interest), shape complementary between the structure and the molecular surface of interest and binding energy or affinity between the structure and the molecular surface of interest, and any combination thereof.

Another criterion which is used for complex assessment is the fold stability pertaining to the reconstructed structure, which is considered in the context of a free protein when unbound to the molecular surface of interest. According to some embodiments, fold stability of the reconstructed structure may be determined by the packing quality, which is assessed according to the calculated free energy of the reconstructed structure.

Each of the matching score criteria is assigned a cutoff value to be used as a selection filter, namely a minimal buried surface area, a minimal shape complementary, a minimal binding free energy, a minimal packing quality and a minimal packing quality (Box 17a in FIG. 2).

According to some embodiments of the present invention, an alternative step (x) includes a conducive matching procedure, wherein a reconstructed structure-molecular surface complex is being assigned a matching score, e.g., a score for buried surface, and if its matching score is found acceptable by a predetermined cutoff criterion of choice, e.g., passes the minimal buried surface cutoff value (Box 17a in FIG. 2), the qualified complex may be subjected to an optional substitution of at least one of the weight fitted reclosed segment in the reconstructed structure of the current complex with a another corresponding weight fitted reclosed segment (Box 9 in FIG. 2), referred to herein as a "replaced segment" (Box 18 in FIG. 2).

According to some embodiments of the present invention, a qualified complex is drawn randomly from a plurality of qualified complexes, subjected to step (xi) and the resulting complex is subjected to an additional cycle of step (x), for example, another conducive matching cycle (Box 16b in FIG. 2). According to some embodiments, the random drawing of qualified complexes may be executed by a Mote Carlo routine for random selection.

According to some embodiments of the present invention, optional step (xi) includes substituting at least one of the weight fitted reclosed segment in the reconstructed structure of a randomly drawn qualified complex, with another corresponding weight fitted reclosed segment and repeating step (x) so as to design a substituted-reconstructed structure-molecular surface complex (Box 18 in FIG. 2).

According to some embodiments of the present invention, the repeated cycle of step (x), which is conducted for a substituted-reconstructed structure, is a conducive matching procedure, as described hereinabove (Box 16b in FIG. 2). In some embodiments, the sequence design, which forms a part of a conducive matching procedure, may be effected for the entire replaced segment, and optionally for other regions of the substituted-reconstructed structure, such as regions that fall within a shell surrounding the interface between the molecular surface of interests and the substituted-reconstructed structure, regions of the substituted-reconstructed structure that fall within a shell surrounding the entire replaced segment, or alternatively the entire substituted-reconstructed structure or any part(s) thereof. According to some embodiments of the present invention, a conducive matching procedure may include any optimization operation which is aimed at optimizing the affinity of the substituted-reconstructed structure to the molecular surface of interest of a molecular entity and for the stability of the fold of the substituted-reconstructed structure. Such additional optimization operations include, without limitation, changing amino acid identities and conformations either singly or in a combination of amino acid, including only rotameric conformations (conformational isomerism) or off-rotamer conformations, or restricting/complementing with conformations observed in naturally occurring structures of the same FSSP, changing the backbone conformation of the replaced segment using backbone minimization, CCD, peptide fragment insertion, kinematic loop closure or any backbone conformation refinement operation, changing and optimizing the relative conformation of other segments with respect to one another using constraints stemming from orientations observed in naturally occurring antibody structures, and the likes.

According to embodiments of the present invention, complexes that undergo a conducive matching procedure are assigned a matching score that includes, without limitation, at least one of a buried surface area score, a shape complementary score and a binding energy score, as well as a fold stability score, and any combination thereof. According to some embodiments of the present invention, a matching score includes any combination of attributes which can be used to evaluate the affinity of the substituted-reconstructed structure to a molecular surface of interest of a molecular entity and evaluate the stability of the fold of the substituted-reconstructed structure, which include, in any combination and without limitation, charge complementarity, polarity and hydrophobicity score pertaining to the binding interface surface, conformational rigidity score as assessed by molecular dynamics, Brownian dynamics score, normal mode analysis (NMA) of protein mobility score, humanization score (reflecting a similarity to human-native amino acid sequences), amino acid sequence compatibility to a given expression system, avoidance of undesired portion of the amino acid sequence, and the likes.

According to some embodiments of the present invention, a combined matching score is used to evaluate the qualifying complexes that have undergone the design optimization matching procedure, and select the amino-acid sequences having the desired affinity to the molecular surface of interest of the molecular entity, which correspond to the reconstructed and optimized structures of the qualifying complexes.

According to some embodiments, step (xii) includes selecting the amino-acid sequence having the desired affinity to the molecular surface of interest of the molecular entity, based on one or more of the matching scores described hereinabove (Box 17b in FIG. 2).

The plurality of amino acid sequences belonging to the qualifying complexes resulting from step (xii) constitute a group of sequences having the desired affinity to the molecular surface of interest of the molecular entity (Box 19 in FIG. 2) as well as other desired attributed arising from various attribute scoring combinations.

Common Structural Folds:

As discussed hereinabove, the method of computationally constructing a library of amino-acid sequences having a common structural fold and the method of designing and selecting an amino-acid sequence having a desired affinity to a molecular surface of interest of a molecular entity, according to some embodiments of the present invention, can be applied to any of the families of structurally similar proteins (FSSP) for which experimentally obtained 3D structures are available.

Examples of a few widely known FSSPs include, without limitation, "alpha/beta hydrolase", "Beta Grasp" (Ubiquitin like fold), "Greek Key", "Jellyroll", "Keyroll", "Plait" (Ferredoxin like fold), "Rossmann fold", "Beta Trefoil", "Ankyrin Repeat", "Armadillo Repeat", "Tetratricopeptide Repeat", and "TIM Barrel", as these naturally ubiquitous folds are known in the art. It is noted herein that while the method presented herein is exemplified primarily in the context of antibodies, it is to be understood that the same concepts are applicable for other common protein folds, motifs and domains, which are shared by several naturally occurring macromolecules.

Table 1 below presents a non-limiting list of common protein folds, as compiled by the SCOP2 server [Murzin A. G. et al., "SCOP: a structural classification of proteins database for the investigation of sequences and structures", J. Mol. Biol., 1995, 247, 536-540; Andreeva, A. et al., "SCOP2 prototype: a new approach to protein structure mining", Nucleic Acids Res., 2014, 42(Database issue), p. D310-4], which can be used to identify source structures in an FSSP.

TABLE 1

| Fold name (SCOP2) | Fold description |
| --- | --- |
| DRBD-type 3-helical bundle | 3-helices, bundle, up-and down anticlockwise topology, closed or partly opened, right-handed twist |
| GroES-like | contains barrel, partly opened, $n^* = 4$, $S^* = 8$ |
| Globin-like | core: 6 helices, folded leaf, partly opened |
| Supersandwich | sandwich, 18 strands in 2 sheets |
| EF/AMT-type beta(6)-barrel | barrel, closed, $n = 6$, $S = 10$, greek-key; antiparallel sheet, clockwise order: 143256 |
| Canonical Rossmann fold | 3 layers, alpha/beta/alpha, parallel beta-sheet of 6 strands, order 321456 |
| SD/FR insert domain-like fold | beta(2)-alpha-beta-alpha(n)-beta-alpha(n)-beta; antiparallel beta-sheet, order: 21543, folded into half-barrel and capped at both ends with helices |
| LDH C-terminal subdomain-like fold | alpha-beta(3)-alpha, meander beta-sheet twisted into a half-barrel, order 123, with helices packed at the opposite ends |
| Rossmann(2 × 2)oid | 3 layers: a/b/a, parallel beta-sheet of 4 strands |
| FMT/AAG-type beta(6)-barrel | barrel, open, $n^* = 6$, $S^* = 10$, greek-key; antiparallel beta-sheet, clockwise order: 125436 |
| Di-heme elbow | mini-fold of two helical CxxCH motifs, covalently attached to a stack of two heme groups |
| Ferredoxin-like | beta-alpha-beta(2)-alpha-beta; 2 layers, a/b; antiparallel beta-sheet, order: 4132 |
| TPM/PMT domain-like | 3 layers, a/b/a; parallel sheet of 5 strands, order 51423 |
| Rossmann(2 × 3)oid (Flavodoxin-like) | 3 layers, a/b/a, parallel beta-sheet of 5 strand, order 21345 |
| Folate-binding halfdomain-like | beta(2)-alpha-beta(3)-alpha; 2 layers, alpha/beta, antiparallel beta-sheet, order: 12543 |
| Glutamyl tRNA-reductase dimerization domain | 6 helices, homodimer of 3-helical domains |
| Voltage-gated potassium channels | oligomeric transmembrane alpha-helical proteins |
| GSR C-terminal domain-like | extended variant of SufE/NifU-like fold: beta(5)-alpha(3), 2 layers, a/b; antiparallel beta-sheet, order 12543 |
| FAD/NAD(P)-binding domain | core: 3 layers, b/b/a, central parallel beta-sheet of 5 strands, order 32145, top antiparallel beta-sheet of 3 strands |
| Formyltransferase-type | 3 layers: a/b/a, mixed beta-sheet of 7 strands, order 3214567, strand 6 is antiparallel to the rest |
| Thioredoxin fold | core: 3 layers, a/b/a, mixed beta-sheet of 4 strands, order: 2134, strand 3 is antiparallel to the rest |
| Rossmann(3 × 2)oid | core: 3 layers, a/b/a, parallel beta-sheet of 5 strands, order 32145 |
| Flavoreductase insert-domain like | beta(4)-alpha-beta; 2 layers, a/b; antiparallel beta-sheet, order: 51432 |
| ClpP-type beta-alpha superhelix | core: 4 turns of (beta-beta-alpha)n right-handed superhelix, capped at C-end by an antiparallel beta-strand |
| HI0933-type beta(6)-barrel | barrel, closed, $n = 6$, $S = 12$, greek-key; clockwise order: 143256 |
| TrkA C-terminal domain-like | beta-X-beta(2)-X-beta-alpha; antiparallel beta-sheet, order: 1423, folded into a half barrel and capped by helix at one end; topological similarity to the HPr-like fold |

TABLE 1-continued

| Fold name (SCOP2) | Fold description |
|---|---|
| Spectrin repeat-like | 3 helices, bundle, up-and down anticlockwise topology, closed, left-handed twist |
| TIM beta/alpha-barrel | (beta-alpha)8; parallel beta-sheet barrel, closed, n = 8, S = 8, strand order 12345678 (anticlockwise); the first seven superfamilies have similar phosphate-binding sites |
| Canonical FwdE/GAPDH domain-like fold | alpha-beta-alpha-beta(3), 2 layers, alpha/beta sandwich, mixed sheet, strand 2 is parallel to strand 1, psi-loop between strands 2 and 3 |
| S13-like H2TH domain | array of 3-5 helices with two 'kissing' loops |
| FAD/NAD(P)-binding domain, circularly permuted variant 1 | core: 3 layers, b/b/a, central parallel beta-sheet of 5 strands, order 15234, top antiparallel beta-sheet of 3 strands |
| GDI isoprenoid-binding domain-like | 5 helices, array, two kissing loops |
| Long alpha-hairpin | 2 helices, antiparallel left-handed coiled-coil |
| Class II aaRS/BPL domain-like | core: beta-X-beta(2)-alpha-beta(4); mixed, mostly antiparallel beta-sheet, order 1237654, strands 1 and 2 are parallel to each other |
| P-loop containing nucleoside triphosphate hydrolases | 3 layers: a/b/a, parallel or mixed beta-sheets of variable sizes |
| PRTase-like | 3 layers, a/b/a, mixed beta-sheet of 6 strands, order 321456, strand 3 is antiparallel to the rest |
| TNF-like | sandwich, 10 strands in 2 sheets, jelly-roll |
| GyrI-type alpha(2),beta(6)-barrel | duplication of beta-alpha-beta(2) motif: antiparallel beta sheet forms barrel (n = 6, S = 12), strand order 132564 (anticlockwise) |
| FadR effector domain-like | core: 6 helices: closed bundle, greek-key, internal pseudo twofold symmetry, mirror topology to the DEATH domain-like fold |
| DtxR dimerization domain-like | 3 helices, arranged into a bowl-like structure; forms a compact homodimer around a single hydrophobic core |
| Resolvase-like | Core: 3 layers: a/b/a, mixed beta-sheet of 5 strands, order 21345, strand 5 is antiparallel to the rest |
| Protein kinase-like (PK-like) | consists of two alpha + beta subdomains that sandwich the ATP binding site |
| Profilin-like | core: beta(2)-alpha(n)-beta(3); antiparallel beta-sheet, order: 21543, 2 layers: a/b; extra N-terminal and/or C-terminal helices form third layer |
| Double-stranded beta-helix | one turn of helix is made by two pairs of antiparallel strands linked with short turns has appearance of a sandwich of distinct architecture and jelly-roll topology |
| GATA zinc finger-like | contains a beta-hairpin between the two pairs of zinc ion ligands and one or more turns of helix at the C-terminus |
| DEATH domain-like | 6 helices: closed bundle, greek-key, internal pseudo twofold symmetry; mirror topology to the FadR effector domain-like fold |
| Immunoglobulin-like beta-sandwich | sandwich, 7 strands in 2 sheets, greek-key some members of the fold have additional strands |
| Chorismate lyase-like | duplication of alpha(2)-beta(3) motif, antiparallel beta sheet, order 123654 |
| Cytochrome b5-like | beta-alpha-beta(2)-alpha(1,2)-(beta)-alpha(2)-beta, 3 layers: a/b/a, antiparallel beta-sheet, order: 1532(4) |
| Urocanase catalytic domain-like | alpha(2)-beta(3)-X-beta-alpha(2)-beta-alpha-beta-alpha-beta(2)-alpha, X is the insertion of a Rossmann-like domain; 3 layers, a/b/a; mixed beta-sheet, order: 21378645, strands 2, 4 and 8 are antiparallel to the rest |
| Fpg N-terminal domain-like | pseudobarrel, capped on both ends by alpha-helices |
| NDP Glycotransferase-like | 3 layers: a/b/a, mixed beta-sheet of 7 strands, order 3214657, order 3214657, strand 6 is antiparallel to the rest |
| NosL/MerB-like | unusual fold, comprises two structural repeats of beta(2)-alpha-beta motifs, forming separate beta-sheets, probable duplication |
| FPGS-type ribokinase-like fold | core: 3 layers: a/b/a, mixed beta-sheet of 8 strands, order 21345678, order 21345678, strand 7 is antiparallel to the rest |
| SBP2HA-like | hypothetical single-domain ancestral fold of type 2 solute binding proteins; 3 layers, a/b/a; mixed beta-sheet of 5 strands, order 21354, strand 5 is antiparallel to the rest |
| Single-stranded right-handed beta-helix | superhelix turns are made of parallel beta-strands and (short) turns |
| Tetracyclin repressor C-terminal domain-like | multihelical ligand-binding and dimerisation domain |
| Galactose-binding domain-like | sandwich, 9 strands in 2 sheets, jelly-roll |
| HAND domain of the nucleosome remodeling ATPase ISWI | 4 helices, irregular array |
| GHKL domain-like | 2 layers: alpha/beta; 8-stranded mixed beta-sheet, order: 87126345, strands 1 and 7 are parallel to each other |
| Ribonuclease H-like motif | 2 layers: a/b, mixed beta-sheet of 5 strands, order 32145, strand 2 is antiparallel to the rest; usually followed by one or more helices forming a third layer on the other side of the beta-sheet or swapping between different domains |

TABLE 1-continued

| Fold name (SCOP2) | Fold description |
| --- | --- |
| DCoH-like | beta(2)-alpha-beta(2)-alpha, 2 layers, alpha/beta; antiparallel beta-sheet, order 1243 |
| ATP-grasp platform-like | beta(3)-alpha-beta(2); 2 layers, a/b; antiparallel beta-sheet, order: 32145 |
| Pili subunit-like | alpha-beta(4); 2 layers, a/b, helix is packed along the strands of antiparallel beta-sheet, order 1234, meander |
| Nudix | beta(3)-alpha-beta(3)-alpha, 3 layers: alpha/beta/alpha, mixed beta-sheet, order: 6(2,3)154, strands 1 and 5 are parallel to each other; contains bifurcation: strands 2 and 3 both H-bond to strands 1; topological similarity to beta-grasp motif |
| Ribosomal protein S5 domain 2-like | core: beta(3)-alpha-beta-alpha, 2 layers: alpha/beta, mixed beta sheet, order: 1243, strand 2 is antiparallel to the rest; psi-loop between strands 2 and 3; left-handed crossover between strands 3 and 4 |
| RIFT-type beta(6)-barrel | barrel, closed, n = 6, S = 10, greek-key; antiparallel beta-sheet, order 125436 (anticlockwise) |
| alpha/beta-Hydrolases | core: 3 layers, a/b/a, mixed beta-sheet of 8 strands, order 12435678, strand 2 is antiparallel to the rest |
| Restriction endonuclease-like | alpha-beta(3)-alpha-beta; 3 layers, a/b/a, mixed beta-sheet, order: 1234, strands 2 is antiparallel to the rest |
| FPGS C-terminal domain-like | 3 layers: a/b/a, mixed beta-sheet of 6 strands, order 126345, strand 1 is antiparallel to the rest |
| Hemerythrin-type up-and-down 4-helical bundle | 4 helices, bundle, up-and down anticlockwise topology, closed or partly opened, left-handed twist |
| Type II GAT domain-like | beta-alpha-beta(2)-alpha-beta(7)-alpha-beta(3); 4 layers: alpha/beta/beta/alpha, 13 strands in two antiparallel beta-sheets; S1 order: 3241A9B; S2 order: 5678CD |
| MoeB-like | 3 layers, a/b/a, mixed beta-sheet of 8 strands, order 32145678, strands 6 and 8 are antiparallel to the rest |
| Trypsin-type beta(6)-barrel | barrel, closed, n = 6, S = 8, greek-key; antiparallel beta-sheet, order: 123654 (clockwise) |
| Sec63 N-terminal domain-like | 6-7 helices, irregular array of short and longer helices, one central helix |
| alpha-alpha superhelix | multihelical, 2 (curved) layers: alpha/alpha, right-handed superhelix |
| POU domain-like | core: 4 helices, folded leaf, closed |
| Methyltransferase-like | core: 3 layers, a/b/a, mixed beta-sheet of 7 strands, order 3214576, strand 7 is antiparallel to the rest |
| Concanavalin-like | sandwich, 12-14 strands in 2 sheets, complex topology |
| SH3-like barrel | barrel, partly opened, n* = 4, S* = 8, meander the last strand is interrupted by a turn of 3-10 helix |
| Thiolase-like | consists of two similar subdomains related by pseudo dyad; 5 layers: a/b/a/b/a, two similar mixed beta-sheet of 5 strands each, order: 32451, strand 5 is antiparallel to the rest |
| CBS-domain pair | duplication: tandem repeat of two beta-X-beta-alpha-beta(2)-alpha motifs of similar sequences, 4 layers: a/b/b/a |
| STAT-type 4-helical bundle | 4 helices, bundle, left-handed twist, right-handed superhelix |
| MgtE membrane domain-like | 5 transmembrane helices, bundle, right-handed twist |
| HPr-like | beta-alpha-beta(2)-alpha-beta-alpha, 2 layers: a/b, antiparallel sheet |
| beta-Grasp | core: beta(2)-alpha-beta(2), 2 layers, a/b; mixed beta-sheet, order: 2143, order: 2143, strands 1 and 4 are parallel to each other |
| Creatinase/aminopeptidase catalytic domain-like | duplication: composed of two very similar alpha(2)-beta(3) units related by a pseudo twofold axis; unusual pairing of the two beta-sheets at a "wrong" positive angle and few H-bonds between the edge strands |
| OB-fold | beta(5)-barrel, closed or partly opened n = 5, S = 10 or S = 8, greek-key; mixed beta-sheet, order 12354 (anticlockwise), strands 3 and 5 are parallel to each other |
| Mor dimerisation domain-like | monomer: alpha(2)-beta; dimer: 4-helical bundle, right-hand twist, capped at one end by beta-ribbon |
| Dimerisation interlock | dimer of alpha-alpha V-shaped units interlocked together with the formation of a 4-helical bundle |
| PROX1 subdomain-type 4-helical bundle | 4 helices, bundle: up-and-down anticlockwise topology, right-hand twist, diamond cross-section, diagonal contact between helices 1 and 3; pseudo twofold symmetry |
| Circularly permuted folate-binding halfdomain-like | beta-alpha-beta(3)-alpha-beta; 2 layers, alpha/beta, antiparallel beta-sheet, order: 51432 |
| Tetrapyrrole methylase C-terminal lobe-like | 3 layers, a/b/a; mixed sheet of 5 strands, order 12534, strands 4 & 5 are antiparallel to the rest |
| Enolase N-terminal domain-like | beta(3)-alpha(3); 2 layers, a/b; meander antiparallel beta-sheet, order: 123, packed against a 3-helical bundle |
| YejL-like interlock | 6 helices, intertwined dimer of three-helical units, bundle |
| FUR dimerisation domain-like | dimer of beta(2)-alpha-beta units; mixed beta-sheet, order 213, strand 2 is antiparallel to the rest; forms a single beta-sheet in the dimer with antiparallel H-bonding of strands 3 and 3' |

TABLE 1-continued

| Fold name (SCOP2) | Fold description |
|---|---|
| Rubredoxin-like | metal ion-binding fold comprising two beta-hairpins; each hairpin contains at its tip two metal ion-coordinating residues, usually, cysteines |
| Nucleotidyltransferase-like | core: alpha-beta-turn-beta-X-beta-(alpha); mixed beta-sheet, order: 123, strand 1 is antiparallel to the rest |
| Histone-fold | core: 3 helices; long middle helix is flanked at each end with shorter helices |
| GltS central domain-like | 3 layers, a/b/a; parallel beta-sheet, order 15432; probable rudiment form of a beta/alpha(8) barrel, resulted from the deletion of the most of the N-terminal half |
| SAM domain-like | 4-5 helices; bundle of two orthogonally packed alpha-hairpins; DNA- and protein-interacting domain |
| PH domain-like beta(6)-barrel | barrel, partly opened; n* = 6, S* = 12; meander; capped by the C-terminal alpha-helix |
| Frataxin-like | alpha-beta(5)-alpha; 2 layers: alpha/beta; meander antiparallel sheet, order 12345 |
| Pair of EF Hands-like | core: 4 helices; open array of 2 alpha-hairpins |
| SMAD/FHA domain-like | sandwich; 11 strands in 2 sheets; greek-key |
| E2 binding domain-like (Circularly permuted variant of the ubiquitin-like topology) | beta-alpha-beta(2)-X-beta(2), 2 layers, a/b; antiparallel beta-sheet 15423; the C-terminal strand occupies the position of the N-terminal strand of the ubiquitin-like proteins but runs in the opposite direction |
| RAP-type triple barrel | heterodimer of two related subunits; forms two similar barrels, n = 8, S = 10 each, which are fused together with the formation of a third barrel, n = 6, S = 8 |
| RRF domain-like | alpha-beta(2)-alpha-beta(2); 2 layers, a/b; antiparallel beta-sheet, order: 1243 |
| Mu transposase-type beta(6)-barrel | barrel; n = 6, S = 8, greek-key; antiparallel beta-sheet, clockwise order: 145632 |
| CycX/PrpD domain-like | 6 helices, up-and-down bundle, right-handed twist; the even-numbered helices are packed around a pseudo three-fold symmetry axis, surrounded by the odd-numbered helices |
| MurF/HprK domain-like | 3 layers, a/b/a; mixed beta-sheet of 5 strands, order 15432, strand 1 is antiparallel to the rest; partial similarity to the swiveling domain fold |
| SCP-like | alpha-beta(3)-X-beta-alpha(2)-beta-alpha; 2 layers: a/b, crossover loop X makes the third layer; antiparallel beta-sheet of 5 strands; order: 32145 |
| 'Hot dog' fold | core: beta-alpha-beta(4); 2 layers, a/b; antiparallel beta-sheet, order 13452 |
| Lambda cro protein-like | beta-alpha(3)-beta(2); 2 layers: a/b; antiparallel beta-sheet, order 123; the three helices retain similar arrangement to the first three helices of the p22 cro protein-like fold, including HTH motif |
| Mad2-like | core: alpha(2)-beta(2)-alpha-beta; mixed sheet, order: 213 |
| beta-hairpin-alpha-hairpin repeat | multiple repeats of beta(2)-alpha(2) motif |
| Pseudo "winged helix" | beta-alpha(2)-beta(2)-alpha; architecture is similar to that of the "winged helix" fold but topology is different |
| beta-clip | double-stranded ribbon sharply bent in two places; the ribbon ends form incomplete barrel; jelly-roll |
| ZU5 domain-like | core: beta-sandwich, 8 strands in 2 sheets; folded meander |
| IL8-like | beta(3)-alpha; 2 layers, a/b; meander antiparallel beta-sheet, order: 123, helix is packed across the beta-strands |
| SWIRM/ISPC-type 4-helical bundle | 4 helices, bundle: up-and-down clockwise topology, right-hand twist, diamond cross-section, diagonal contact between helices 2 and 4; pseudo twofold symmetry |
| RpiR/Int-type 5-helical array | 5 helices, array; helices 1 and 5 cap the same open end of a DRBD-type 3-helical bundle |
| Canonical WHD (winged helix domain) fold | alpha(3)-beta(2); 3-helical DRBD-type bundle, capped at one end with a beta-haipin; may contain extra beta-strand in the loop, connecting helices 1 and 2 |
| Helix-extended WHD fold | alpha(3)-beta(2)-alpha; 3-helical DRBD-type bundle, capped at one end with a beta-haipin and helix 4 |
| Sheet-extended WHD fold SDR-type extended Rossmann fold | alpha-beta(2)-alpha(2)-beta(2); 3-helical DRBD-type bundle, capped at one end with a 4-stranded beta-sheet |
| OCD-type extended Rossmann fold | 3 layer alpha/beta/alpha, parallel beta-sheet of 7 strands, order 3214567, left-handed crossover connection between strands 6 and 7 |
| CoA-binding domain-type Rossmann fold | 3 layer alpha/beta/alpha, parallel beta-sheet of 8 strands, order 32145867 |
| 6PGDH-type extended Rossmann fold | 3 layer alpha/beta/alpha, mixed, mostly parallel beta-sheet of 7 strands, order 3421567, strand 3 is antiparallel to the rest |
| DAO-type FAD/NAD(P)-binding domain | 3 layer alpha/beta/alpha, mixed beta-sheet of 8 strands, order 32145678, strands 7 and 8 are parallel to each other and antiparallel to the rest |
| "Reversed" ferredoxin-like fold | variant of FAD/NAD(P)-binding domain, in which an alpha-helix replaces the top meander beta-sheet: 3 layers, a/b/a, parallel beta-sheet of 5 strands, order 32145 |

TABLE 1-continued

| Fold name (SCOP2) | Fold description |
|---|---|
| UBA-type 3-helical bundle | beta-alpha-beta(2)-alpha-beta; 2 layers, a/b; antiparallel beta-sheet, order: 1423 |
| YrdC/RibB-like | 3-helices, bundle, up-and down clockwise topology, closed or partly opened, right-handed twist |
| HypF zinc finger-like | core: alpha-beta(2)-alpha-beta-alpha(2)-beta(2)-alpha-beta-alpha-beta; 3 layers, a/b/a; mixed twisted sheet of 7 strands, order: 7126354; strands 7 and 1 are parallel to each other |
| SBP2HA-like circular permuted variant 1 | coordinates zinc ion with two CxxC motifs, each motif is located at the N-end of a helical turn |
| Sua5 domain-like | 3 layers, a/b/a; mixed beta-sheet of 5 strands, order 51423, strand 1 is antiparallel to the rest |
| MptD-like | 3 layers, a/b/a; parallel beta-sheet of 5 strands, order 51423 |
| Canonical cyclophilin-type beta(8)-barrel | alpha(2)-beta(4); 2 layers: a/b; antiparallel beta-sheet, order: 1234, meander |
| Cyclophilin38-type double beta-barrel | barrel, closed; n = 8, S = 10; antiparallel beta-sheet, clockwise order: 12756438, complex topology with two overside connections that cross each other |
| Anticodon-binding domain-like | Bifurcated beta-sheet of 9 strands folded into two conjoint barrels; barrel 1: closed; n = 8, S = 10; antiparallel beta-sheet, anticlockwise order: 12659348; barrel 2: closed n = 6, S = 10; mixed beta-sheet, clockwise order: 126578, strands 7 and 8 are parallel to each other |
| FAD-binding/transporter-associated domain-like | 3 layers: a/b/a, mixed beta-sheet of five strands, order 21345, strand 4 is antiparallel to the rest |
| immunoglobulin/albumin-binding domain-like | consists of two alpha + beta subdomains |
| Rossmann(3 × 4)oid | 3 helices, bundle, up-and down clockwise topology, closed, left-handed twist; mirror topology to the spectrin-like fold |

According to some embodiments of the present invention, a small subset of the above presented FSSP (Table 1) include, without limitation, a common fold of immunoglobulins, "alpha/beta hydrolase", "Beta Grasp" (Ubiquitin like fold), "Greek Key", "Jellyroll", "Keyroll", "Plait" (Ferredoxin like fold), "Rossmann fold", "Beta Trefoil", "Ankyrin Repeat", "Armadillo Repeat", "Tetratricopeptide Repeat" and "TIM beta/alpha-barrel".

According to some embodiments of the present invention, the common structural fold is of an antibody. It is noted that at the time of the invention more than 1900 PDB entries are available for antibodies.

The term "antibody", as used herein this, includes intact molecules as well as functional fragments thereof, such as Fab, F(ab')2, scFv, scFab, and Fv that are capable of binding to, for example, macrophages. These functional antibody fragments include, without limitation: (1) Fab, the fragment which contains a monovalent antigen-binding fragment of an antibody molecule, can be produced by digestion of whole antibody with a proteolytic enzyme, such as papain, to yield an intact light chain and a portion of one heavy chain; (2) Fab', the fragment of an antibody molecule that can be obtained by treating whole antibody with a proteolytic enzyme, such as pepsin, followed by reduction, to yield an intact light chain and a portion of the heavy chain; two Fab' fragments are obtained per antibody molecule; (3) (Fab')2, the fragment of the antibody that can be obtained by treating whole antibody with a proteolytic enzyme, such as pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

According to some embodiments of the present invention, the common structural fold is of an Fv of an antibody, defined as a genetically engineered fragment containing the variable region of the light chain and the variable region of the heavy chain expressed as two chains.

With respect to the exemplary FSSP of TIM beta/alpha-barrel fold, it is noted that at the time of the invention, more than 2000 PDB entries are available for proteins having a TIM beta/alpha-barrel fold or at least containing a TIM beta/alpha-barrel domain. This exemplary FSSP include, without limitation, Triosephosphate isomerase (TIM), Ribulose-phoshate binding barrel, Thiamin phosphate synthase, Pyridoxine 5'-phosphate synthase, FMN-linked oxidoreductases, Inosine monophosphate dehydrogenase (IMPDH), PLP-binding barrel, NAD(P)-linked oxidoreductase, (Trans) glycosidases, Metallo-dependent hydrolases, Aldolase, Enolase C-terminal domain-like, Phosphoenolpyruvate/pyruvate domain, Malate synthase G, RuBisCo C-terminal domain, Xylose isomerase and Xylose isomerase-like, Bacterial luciferase and Bacterial luciferase-like, Nicotinate/Quinolinate PRTase C-terminal domain-like, PLC-like phosphodiesterases, Cobalamin (vitamin B12)-dependent enzymes, tRNA-guanine transglycosylase, Dihydropteroate synthetase and Dihydropteroate synthetase-like, FAD-linked oxidoreductase, Monomethylamine methyltransferase MtmB, Homocysteine S-methyltransferase, (2r)-phospho-3-sulfolactate synthase ComA, Radical SAM enzymes, GlpP-like, CutC-like, ThiG-like, TM1631-like and EAL domain-like proteins.

With respect to the exemplary FSSP of alpha/beta hydrolase fold, it is noted that at the time of the invention, more than 1600 PDB entries are available for proteins having a alpha/beta hydrolase fold or at least containing a alpha/beta hydrolase domain, which is observed, without limitation in Acetylcholinesterase, Carboxylesterase, Mycobacterial antigens, Hypothetical protein TT1662, PepX catalytic domain, Prolyl oligopeptidase C-terminal domain, DPP6 catalytic domain, Serine carboxypeptidase, Gastric lipase, Proline iminopeptidase, Acetyl xylan esterase, Haloalkane dehalogenase, Dienelactone hydrolase, Carbon-carbon bond hydrolase, Biotin biosynthesis protein BioH, Aclacinomycin methylesterase RdmC, Carboxylesterase/lipase, Epoxide hydrolase, Haloperoxidase, Thioesterases, Carboxylesterase/thioesterase 1, Ccg1/TafII250-interacting factor B (Cib), Bacterial esterase, Fungal lipases, Bacterial lipase, N-terminal domain of Pancreatic lipase, Hydroxynitrile lyase, Thioesterase domain of polypeptide, polyketide and fatty acid synthases, Cutinase, YdeN, Putative serine hydrolase Ydr428c, C-terminal domain of Acylamino-acid-releasing enzyme, Hypothetical esterase YJL068C, Atu1826, PHB depolymerase, IroE-like, TTHA1544, 0-acetyltransferase and 2,6-dihydropseudooxynicotine hydrolase.

With respect to the exemplary FSSP of Rossmann fold, it is noted that at the time of the invention, more than 1350 PDB entries are available for proteins having a Rossmann fold or at least containing a Rossmann domain, which is observed, without limitation in Alcohol dehydrogenase, Tyrosine-dependent oxidoreductases, Glyceraldehyde-3-phosphate dehydrogenase, Formate/glycerate dehydrogenases, LDH N-terminal domain, 6-phosphogluconate dehydrogenase, Aminoacid dehydrogenase, Potassium channel NAD-binding domain, Transcriptional repressor Rex, CoA-binding domain and Ornithine cyclodeaminase.

Discussions on the identification and classification of FSSP and of conserved folds and domains in protein's three-dimensional structures, are provided in, for example, Holm, L. et al., [*Protein Science*, 1992, 1, p. 1691-1698; Marchler-Bauer A. et al., *Nucleic Acids Res.*, 2007, 35 (Database issue), D237-40; and Marchler-Bauer A. et al., *Nucleic Acids Res.*, 2013, 41 (Database issue), D348-52, which are incorporated herein by reference in its entirety as if fully set forth herein. For a comprehensive discussion, classification and identification of FSSPs, a person of ordinary skills in the art can use, for example, publically accessible services, such as SCOP [Andreeva A. et al., *Nucleic Acids Res.*, 2008, 36(Database issue), p. D419-25], SCOP2 [Andreeva, A. et al., "*SCOP2 prototype: a new approach to protein structure mining*", Nucleic Acids Res., 2014, 42(Database issue), p. D310-4], and the likes.

A Method of Producing Amino-Acid Sequences of Proteins Having a Desired Affinity to a Molecular Surface of Interest:

A product of the method presented herein, according to some embodiments of the present invention, is a set of amino-acid sequences (Box 19 in FIG. 2), which are recommended for expression and further optimization using experimental in vitro and/or in vivo procedures.

Hence, according to another aspect of some embodiments of the present invention, there is provided a method of producing an amino-acid sequence having a desired affinity to a molecular surface of interest, which is carried out by:

designing and selecting the amino-acid sequence having the desired affinity to the molecular surface of interest according to embodiments of the method of designing and selecting an amino-acid sequence having a desired affinity to a molecular surface of interest of a molecular entity presented herein; and expressing the amino-acid sequence in an expression system, thereby producing the amino-acid sequence having the desired affinity to the molecular surface of interest.

Most generally a designed protein or fragment of a protein can be reverse-translated and reverse-transcripted into a DNA segment encoding the protein or fragment, referred to herein as a genetic template. This genetic template can then be synthesized using established methodologies which are publically and commercially available. 5' and 3' fragments that allow for restriction-ligation reaction or homologous recombination into commonly used pET or other protein-expression plasmids are added to the genetic template through standard PCR extension. The genetic template can then be restricted using compatible restriction enzymes into the expression plasmid or incorporated into the expression plasmid through homologous recombination. Standard expression organisms (bacteria, yeast, phage, insect, or mammalian cells) are transformed with the compatible gene-encoding plasmid and expression is induced.

Given the size and complexity of proteins, chemical synthesis is typically not a viable option for expressing an amino-acid sequence afforded by any one of the methods presented herein. Instead, living cells and their cellular machinery can be harnessed as biologic expression systems to build and construct the designed proteins based on corresponding genetic templates.

Unlike proteins, the genetic template (DNA) of the protein of interest is relatively simple to construct synthetically or in vitro using well established recombinant DNA techniques. Therefore, DNA templates of specific amino acid sequences afforded by any one of the methods presented herein, with or without add-on reporter or affinity tag sequences, can be constructed as templates for designed recombinant protein expression.

Strategies for recombinant protein expression are well known in the art, and typically involve transfecting cells with a DNA vector that contains a genetic template of interests and then culturing the cells so that they transcribe and translate the designed protein. Typically, the cells are then lysed to extract the expressed protein for subsequent purification. Both prokaryotic and eukaryotic in vivo protein expression systems are widely used. The selection of the system depends on the type of protein, the requirements for functional activity and the desired yield.

Bacterial protein expression systems are most widely used since bacteria are easy to culture, grow quickly and produce high yields of a designed recombinant protein. However, multi-domain eukaryotic proteins expressed in bacteria often are non-functional because the cells are not equipped to accomplish the required post-translational modifications or molecular folding. Also, many proteins become insoluble as inclusion bodies that are very difficult to recover without harsh denaturants and subsequent cumbersome protein-refolding procedures.

Mammalian in vivo expression systems usually produce functional protein with some notable limitations. Cell-free protein expression is the in vitro synthesis of protein using translation-compatible extracts of whole cells. In principle, whole cell extracts contain all the macromolecules components needed for transcription, translation and even post-translational modification. These components include RNA polymerase, regulatory protein factors, transcription factors, ribosomes, and tRNA. When supplemented with cofactors, nucleotides and the specific gene template, these extracts can synthesize proteins of interest in relative ease.

Although typically not sustainable for large scale production, cell-free protein expression systems have several advantages over traditional in vivo systems. Cell-free systems enable protein labeling with modified amino acids, as well as expression of designed proteins that undergo rapid proteolytic degradation by intracellular proteases. Also, with the cell-free method, it is simpler to express many different proteins simultaneously (e.g, testing designed protein by expression on a small scale from many different recombinant DNA templates).

In some embodiments of the present invention, the common structural fold is that of an antibody. Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

In some embodiments of the present invention, the common structural fold is that of a fragment of an antibody. Antibody fragments according to some embodiments of the invention can be prepared by proteolytic hydrolysis of the antibody or by expression in E. coli or mammalian cells (e.g., Chinese hamster ovary cell culture or other protein expression systems) of DNA encoding the fragment. Antibody fragments can be obtained using a proteolytic enzyme, such as pepsin or papain, for digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (scFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing scFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

According to some embodiments of the present invention, the methods presented herein, including any one of the embodiments thereof, and any combination thereof, can be used to humanize a structure of a protein, such as, for example an antibody. In the context of these embodiments of the present invention, the amino acid sequence of a binding domain of a protein, e.g., a Fv fragment of an antibody, is designed according to embodiments of the present invention, and then the entire protein is humanize by finding a human framework that is most compatible therewith. Such a method follows the rationale of some methodologies for protein humanization, as described herein.

Methods for humanizing non-human antibodies are known in the art. Generally, a humanized antibody has one or more amino acid residues introduced into it from a source which is non-human. These non-human amino acid residues are often referred to as import residues, which in the context of some embodiments of the present invention, are the product of design by the methods presented herein. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting non-human sequences for the corresponding designed amino acid sequences.

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which the amino acid sequence form a complementary determining region (CDR), or larger domains that also include framework sections (e.g., Fv domain) of the recipient are replaced by an amino acid sequence designed according to the methods presented herein, having the desired specificity, affinity, stability and capacity. In some instances, Fv framework amino acid sequence of the human immunoglobulin is replaced by corresponding non-human amino acid sequence afforded by the methods presented herein. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of afforded by the methods presented herein, and most or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Fully or partially designed antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, fully or partially designed antibodies can be made by introduction of human immunoglobulin loci into transgenic animals, e.g., mice in which the endogenous immunoglobulin genes have been partially or completely inactivated. Upon challenge, fully or partially designed antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Molecular Surface of Interest of a Molecular Entity:

According to some embodiments of the present invention, the method of designing and selecting an amino-acid sequence having a desired affinity to a molecular surface of interest of a molecular entity (referred to herein as a "designed protein"), can be carried out by providing atomic coordinates of atoms of a definable molecular surface of interest that forms a part of the molecular entity.

By having a definable molecular surface, it is meant that the molecular entity, or at least the molecular surface of interest, with which the designed protein is meant to interact, can be described by atomic coordinates in three dimensions.

As used herein, the phrase "molecular entity" describes a molecule, a compound, a complex, an adduct and/or a composite, that can be represented by a set of atomic coordinates in three dimensional space. According to some embodiments of the invention, the atomic coordinates represent the relative positions of all atoms of the target, or at least the non-hydrogen atoms.

According to some embodiments of the present invention, it is sufficient to provide the atomic coordinates of a molecular surface of interest, which forms a part of the molecular entity, essentially since it is the molecular surface which interacts with the designed protein when the two entities form a complex (bind to one another). In other words, according to some embodiments of the present invention, a molecular entity may be defined by atomic coordinates that define at least the molecular surface to which the designed protein is designed to interact and bind to. According to some embodiments of the invention, the molecular surface of interest is defined so as to encompass a wider area than it estimated to bind with the designed protein so as to allow the method to explore and identify a larger than expected area of recognition and binding.

The origin of the atomic coordinates of at least the molecular surface of interest of a molecular entity can be obtained by an experimental procedure such as, for example, an X-ray diffraction or NMR analysis, conducted on a sample of a tangible naturally occurring or synthetic substance, obtained by a computational procedure or a combination thereof.

The molecular surface of interest may include atoms which are associated therewith and can be assigned atomic coordinates in the frame of the main moiety, but not necessarily bound covalently. For example, according to some embodiments of the present invention, the molecular surface of interest is represented by atomic coordinates of atoms belonging to the molecular entity as well as atomic coordinates of solvent (e.g., water) molecules which are bound to the molecular entity by hydrogen bonds. Likewise, atomic coordinates of ions, which are associated with the molecular entity, may also form a part of the structural representation of the molecular surface of interest.

The atomic coordinates of a molecular surface of interest may represent a thermodynamically stable under given conditions, according to some embodiments of the invention, or alternatively, represent the three dimensional structure of an unstable conformation, such as in the case of a transition state of a target molecule which is a between two more stable conformations of the same molecular entity. The molecular surface of interest can also represent one of several conformers of a single molecular entity, as in the case of cellular receptors proteins that have more than one state, hence more than one recognizable molecular surface; for each of which a designed protein can be designed using the presently disclosed methods.

Typically, but not exclusively, a molecular entity is one that can exert one or more biological and/or pharmaceutical activities. According to some embodiments of the present invention, the molecular entity can be used interchangeably with any of the terms "bioactive agent", "pharmaceutically active agent", "pharmaceutically active material", "therapeutic active agent", "biologically active agent", "therapeutic agent", "drug" and other related terms, including, for example, genetic therapeutic agents, non-genetic therapeutic agents, small molecules and cells.

Representative examples of molecular entities, for which a designed protein can be designed for using the presently described method include, without limitation, amino acids and peptide- and protein-based substances such as cytokines, chemokines, chemo-attractants, chemo-repellants, agonists, antagonists, antibodies, antigens, enzymes, co-factors, growth factors, haptens, hormones, and toxins; nucleotide-based substances such as DNA, RNA, oligonucleotides, labeled oligonucleotides, nucleic acid constructs, and antisenses; saccharides, polysaccharides, phospholipids, glycolipids, viruses and cells, as well as hydrophilic or amphipathic radioisotopes, radiopharmaceuticals, receptors, steroids, vitamins, angiogenesis-promoters, drugs, anti histamines, antibiotics, antidepressants, anti-hypertensive agents, anti-inflammatory agents, antioxidants, anti-proliferative agents, anti-viral agents, chemotherapeutic agents, co-factors, cholesterol, fatty acids, bile acids, saponins, hormones, metal ions, synthetic or natural surfaces, inhibitors and ligands, and any combination thereof.

Each of the molecular entities described herein can be a macro-biomolecule or a small, organic molecule.

The term "macro-biomolecules" as used herein, refers to a polymeric biochemical substance, or biopolymers, that occur naturally in living organisms. Polymeric macro-biomolecules are primarily organic compounds, namely they consist primarily of carbon and hydrogen, optionally and typically along with nitrogen, oxygen, phosphorus and/or sulfur, while other elements can be incorporated therein but typically at a lower rate of occurrence. Amino acids and nucleotides are some of the most important building blocks of polymeric macro-biomolecules, therefore macro-biomolecules are typically comprised of one or more chains of polymerized amino acids (e.g., peptides and proteins), polymerized nucleotides (e.g., nucleic acids), polymerized saccharides, polymerized lipids and combinations thereof. Macromolecules may comprise a complex of several macromolecular subunits which may be covalently or non-covalently attached to one another. A ribosome, a cell organelle and an intact virus are also encompassed herein under the term "a macro-biomolecule".

A macro-biomolecule, as used herein, has a molecular weight higher than 1000 dalton (Da), and can be higher than 3000 Da, higher than 5000 Da, higher than 10 kDa and even higher than 50 KDa.

Representative examples of macro-biomolecules, for which an antibody can be designed for using the presently described method include, without limitation, peptides, polypeptides, proteins, enzymes, antibodies, oligonucleotides and labeled oligonucleotides, nucleic acid constructs, DNA, RNA, antisense, polysaccharides, receptors, viruses and any combination thereof, as well as cells, including intact cells or other sub-cellular components and cell fragments.

As used herein, the phrase "small organic molecule" or "small organic compound" refers to small compounds which consist primarily of carbon and hydrogen, along with nitrogen, oxygen, phosphorus and sulfur and other elements at a lower rate of occurrence. Organic molecules constitute the entire living world and all synthetically made organic compounds, therefore they include all natural metabolites and man-made drugs. In the context of the present invention, the term "small" with respect to a compound, agent or molecule, refers to a molecular weight lower than about 1000 grams per mole. Hence, a small organic molecule has a molecular weight lower than 1000 Da, lower than 500 Da, lower than 300 Da, or lower than 100 Da.

Representative examples of small organic molecules, for which an antibody can be designed for using the presently described method include, without limitation, angiogenesis-promoters, cytokines, chemokines, chemo-attractants, chemo-repellants, drugs, transition-state analogues, agonists, amino acids, antagonists, anti histamines, antibiotics, antigens, antidepressants, anti-hypertensive agents, anti-inflammatory agents, antioxidants, anti-proliferative agents, anti-viral agents, chemotherapeutic agents, co-factors, fatty acids, growth factors, haptens, hormones, inhibitors, ligands, saccharides, radioisotopes, radiopharmaceuticals, steroids, toxins, vitamins and any combination thereof.

A De Novo Designed Protein:

As presented hereinabove, embodiments of the present invention provide methods for designing an amino acid sequence, which is able to fold into a stable 3D structure that exhibits a desired affinity to a molecular surface of interest. The methods disclosed herein can be applied for designing binding proteins that can bind any molecular entity that has a definable molecular surface at high affinity and selectivity while maintaining a feasible and stable overall structure. By "definable", it is meant that the molecular surface can be represented by a set of atomic coordinates for each of its atoms, or at least some of its atoms.

According to another aspect of some embodiments of the present invention, there is provided an amino acid sequence having a desired affinity to a molecular surface of interest. This amino acid sequence can be used to create a corresponding genetic template for use in an in vitro expression system, as exemplified hereinbelow.

In some embodiments of the present invention, the amino acid sequence having a desired affinity to a molecular surface of interest is that of an antibody fragment, such as the antibody's variable domain (Fv) as a single-chain construct (scFv) or fused to naturally occurring constant domains as an antibody fragment (Fab), either disulfide-linked or fused into a single chain (scFab), or as a full-length IgG of an antibody. There are many alternative paths to expressing and testing antibodies for binding. These include phage, ribosome, and yeast display, bacterial expression and refolding from inclusion bodies, secretion of antibodies from bacteria, yeast, mammalian, or insect cells. As a first step in each of these paths the designed antibody of interest is cloned into an expression plasmid, either separately for the variable light and variable heavy domain or fused as one gene segment in the case of an scFv construct. Briefly, each designed antibody is synthesized from DNA oligos or ordered from a custom DNA-synthesis service and cloned into the pCTCON2 plasmid for yeast cell-surface display. Yeast transformation, expression, and binding assays are known in the art, and standard laboratory flow-cytometers or fluorescence-activated flow cytometers (FACS) are used to monitor the designed antibody's expression levels using a fluorescently labeled anti-cmyc antibody and binding.

Exemplary Uses of the Designed Protein:

The method presented herein can be used, without limitation, to:

Design an improved and refined binding protein based on an existing natural binding protein, which is characterized by having higher stability, affinity, or specificity compared with the natural protein;

Humanize a known non-human binding protein, such as an antibody, by finding a human framework that is most compatible therewith;

Design de novo binding proteins for any molecular entity, and for any use, including pharmaceutical, analytical or diagnostic use, as tools for synthesis and purification tasks, and the likes; and Predict the structure of a binding protein for which an experimental 3D structure is not available, based on the structure of its known ligand, or solely based on the sequence of an isolated protein.

Since the molecular surface of interest can be defined by atomic coordinates, even if that surface is conformationally dynamic, namely a surface of a molecular entity that changes conformations under given conditions, the method presented herein can design a protein, such as, for example, an antibody, that can bind to the molecular entity's molecular surface even if that surface is manifested as a transition state or an intermediate.

The method presented herein can be used to design enzymes and other catalytic proteins, such as catalytic antibodies, by using a molecular surface of a transition state. For example, a protein can be designed to bind to a molecular surface of a molecule at a confirmation that corresponds to a transition state between a substrate and a product. A protein such as that would bind to the molecule while conferring or promoting the transition state conformation on the molecule, thereby catalyzing the transition (reaction) from substrate to product.

The method presented herein can also be used to design signaling proteins, by using as a molecular surface of any one of the conformational states of a receptor, or otherwise any molecular switch. For example, a protein can be designed to bind to a molecular surface of a receptor at a receptor confirmation that corresponds to an "on", "off", "open", "close" or any other state having a biological expression of some sort. A protein such as that would bind to a corresponding receptor in a biological system, while conferring or promoting the "on", "off", "open", "close" or any other conformation of the receptor, thereby serving as a signaling protein.

Design of Novel Enzymatic Functions:

According to some embodiments of the present invention, the method presented herein can be used to afford a structure that exhibits an affinity to any ligand or substrate structure of interest in any given binding/active site. According to some embodiments, the method can be implemented by superimposing catalytic residues' functional groups from an active/binding site of an existing protein structure with the bound ligand/substrate of interest, or an analog thereof, to the corresponding groups on the designed structure. If an existing bound structure is not available, a model can be computationally generated in which functional groups are geometrically oriented around a transition state such that its predicted free energy is lowered, providing the basis for catalysis. Optimal residue identities for other scaffold positions can then be selected to define an active/binding site that is complimentary in shape to the ligand/substrate while also stabilizing the catalytic residues in their predetermined conformations. Backbone conformational sampling can also be introduced to optimize the shape complementarity and position of the catalytic residues.

Protein Structure Prediction Based on Amino-Acid Sequence:

An extension of the structure design method is a method of structure prediction of a protein with a known sequence and a database of known structures which can be segmented into segments having the exact number of amino acids as in the segments of the known sequence. The method is exemplified herein using antibodies.

The structure prediction method is based on sampling of Vl/Vh rigid-body orientations observed in the Protein Data Bank (PDB), and begins by pre-computing the rigid-body orientation of the light and heavy chains with respect to one another in each antibody PDB entry, and storing this information in a database. While the sequence design method only samples backbone and sidechain conformations but allows changes in the amino-acid sequence including insertions and deletions of amino-acids, the structure prediction method includes sampling of rigid-body displacements from the pre-computed database while keeping the amino-acid of the target protein fixed.

The method continues by combinatorially generating a plurality of combinations of backbone segments that have the same length as the segments comprising the target antibody. Sampling comprises five types of moves: Replacement of one of the modeled fragments (VL, VH, L3, and H3) with a random conformation of the same length from the pre-computed backbone libraries and replacement of the rigid-body orientation with a randomly chosen orientation selected from the pre-computed rigid-body library. According to some embodiments, rigid-body orientations are also sampled combinatorially. Following each such move amino acid side chain conformations within a 6 Å shell surrounding the modeled segment are packed and minimized using the all-atom Rosetta energy function, and the resulting energy is compared to the previously accepted energy; the newly generated structure is accepted subject to the Metropolis criterion, and the process is repeated for several steps (100-500) using a simulated annealing protocol, ending at temperature 0.

In contrast to other methods for antibody structure prediction, this method relies on experimental structures for modeling all degrees of freedom (segments and light chain/heavy chain rigid body orientations). It was found that the structure prediction method provided herein, according to some embodiments of the present invention, outperforms the best methods in that benchmark both in terms of accuracy of loop conformations and stereo-chemical quality (data not shown). By disallowing unlimited conformational structure optimization against an error prone force field, and instead relying more on the experimental structures, it is expect that the structure prediction method provided herein can more accurately capture the conformational energy landscape of target structures.

It is expected that during the life of a patent maturing from this application many relevant methods for designing de novo antibodies structures based on sequence and conformational information found in naturally occurring antibodies will be developed, and the scope of the term methods for designing de novo antibodies structures based on sequence and conformational information found in naturally occurring antibodies is intended to include all such new technologies a priori.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a scaffold" or "at least one scaffold" may include a plurality of scaffolds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Methods

Source Code Availability:

Some portion of the methods were implemented within the Rosetta macromolecular modeling software suite [Das & Baker, Annu Rev Biochem 2008, 77:363-382] and are available through the Rosetta Commons agreement. Some of the methods have been implemented through RosettaScripts [Fleishman et al., PLoS One 2011, 6:e20161].

Some portions of the methods were implemented using the Monte-Carlo method [Hazewinkel, Michiel, ed. (2001), "Monte-Carlo method", Encyclopedia of Mathematics, Springer, ISBN 978-1-55608-010-4].

Binding Mode Criteria:

Deciding which designs recapitulate the native binding mode was based on the CAPRI challenge criteria [Méndez et al., Proteins 2003, 52:51-67]. Specifically, I_RMS which measures the RMSD of the target interface residues (all residues with atoms within a 10 Å radius of the antibody) between design and native structure after both antibody structures are aligned. The interface RMSD cutoff between the natural antibody and the designed antibody was set to 4 Å.

The following script was written in Python and was implemented using Pymol [The PyMOL Molecular Graphics System, Version 1.6.1 Schrödinger, LLC.]. To run this script the designed complexes database was placed in a folder along with the natural antibody-antigen complexes. Create a text file. This text file named: "pdb_file_list", containing a list of all the design PDB files and of the native antibody-antigen complex as the first entry has been created. The execution command is "pymol -c lig_rms.py" in Bash terminal. The command was executed from the same folder where the design PDBs were stored. The output from this script were two folders, one containing copies of all designs with I_RMS values greater than 4 Å ("more_than_4") and the second folder contained all designs with I_RMS values less than 4 Å ("less_than_4").

```
lig_rms.py script:
#!/usr/bin/python
import os
from os.path import basename
import csv
#file list
```

```
pdb_file_list = open("pdb_file_list", "r")
lines = pdb_file_list.read( ).split('\n')
#load reference structure
cmd.load(lines[0])
template=basename(lines[0])[:-4]
#split reference structure to AB (chain A) and lig (chain B)
cmd.select("template", template)
cmd.select("AB",template+" and chain A")
cmd.select("lig",template+" and chain B")
lines.pop(0) #remove template pdb file name from the list of files
for line in lines:
    try:
        if line !="":
            #print line
            cmd.load(line)
            cmd.remove("hetatm")
            cmd.remove("hydro")
            target=line[:-4]
            cmd.select("target",target)
            ###############################
            # create selection for target v1
            ###############################
            #align ABs by v1 cys
            cmd.select("target_cys", "target and resn cys and resi 100- and chain A")
            cmd.select("template_cys","template and resn cys and resi 100- and chain A")    cmd.select("lig_target",target+" and chain B")
            cmd.pair_fit("target_cys","template_cys")
            cmd.select("template_interface","br. AB and name ca+n+c+o around 10 and lig")
            lig_res={'resnums': [ ]}
            cmd.iterate("template_interface", 'resnums.append(resi)',space=lig_res)
            myset=(set(lig_res.get('resnums')))
            my_str=""
            for i in myset:
                my_str=my_str+"+"+str(i)
            cmd.select("temp_lig_inter_bb","template_interface and name ca+n+o")
            cmd.select("tar_lig_inter_bb","lig_target and name ca+n+o and resi "+my_str)
        rms=cmd.rms_cur("temp_lig_inter_bb","tar_lig_inter_bb")
            if not os.path.isdir("less_than_4"):
                os.makedirs("less_than_4")
            if not os.path.isdir("more_than_4"):
                os.makedirs("more_than_4")
            if(float(rms)<4.0):
                cmd.save("less_than_4/"+line)
            else:
                cmd.save("more_than_4/"+line)
            cmd.delete("tar*")
            cmd.delete(target)
    except:
        continue
```

CDR Definitions:

The CDR definitions used in this work are in general agreement with previous definitions known in the art. For clarity, CDR definitions presented herein follow the Chothia position numbering scheme. In the following Example, two different CDR definitions are used. The first, closely matching the V(D)J gene segments, treats CDRs 1 and 2 as one unit. This definition was used during the construction of the PSSMs and during backbone sampling, as described hereinbelow. The second definition is similar to conventional CDR definitions and treats each CDR (CDR1, CDR2 and CDR3) as a separate unit to determine the level of the sequence constraint thresholds, as described hereinbelow. Table 2 hereinabove presents a comparison between the abovementioned CDR definitions.

Shape Complementarity:

Shape complementarity was computed using the algorithm described in Singer et al. [*J. Immunol.*, 1993, 150, p. 2844-2857] and implemented in Rosetta software suite. The following script "sc.xml" was used to execute the shape complementarity optimization. This script was written in "RosettaScripts" and implemented using the Rosetta modeling suite.

Example of Execution rosetta_scripts.default.linuxgccrelease -s 5_lahw_sc+lig_orig_0001.pdb -parser:protocol sc.xml -overwrite

```
sc.xml script:
<dock_design>
  <SCOREFXNS>
  </SCOREFXNS>
  <FILTERS>
    <ShapeComplementarity name=sc confidence=0/>
  </FILTERS>
  <MOVERS>
    <AtomTree name=docking_tree docking_ft=1/>
  </MOVERS>
  <APPLY_TO_POSE>
  </APPLY_TO_POSE>
  <PROTOCOLS>
    <Add mover_name=docking_tree />
    <Add filter_name=sc/>
  </PROTOCOLS>
</dock_design>
```

Docking of the Antibody Scaffolds to the Target Epitope:

Each of the 4,500 antibody scaffolds constructed as described below was initially aligned to the natural antibody framework in the complex structure. The target coordinates were then added to the antibody scaffold structure. The binding mode was then perturbed with RosettaDock [Gray et al., *J Mol Biol* 2003, 331:281-299] using reduced representation docking (centroid mode), using the following dockLowRes.xml script. This script was written in "RosettaScripts" and implemented using the Rosetta modeling suite.

Example of execution: rosetta_scripts.default.linuxgccrelease -s 5_lahw_sc+lig_orig_0001.pdb -parser:protocol dockLowRes.xml -overwrite

```
dockLowRes.xml script:
<dock_design>
  <SCOREFXNS>
  </SCOREFXNS>
  <TASKOPERATIONS>
  </TASKOPERATIONS>
  <MOVERS>
    <DockingProtocol name=dock_lowres low_res_protocol_only=1 docking_score_low=score_docking_low/>
    <SwitchResidueTypeSetMover name=fa set=fa_standard/>
  </MOVERS>
  <FILTERS>
  </FILTERS>
```

```
  <PROTOCOLS>
    <Add mover=dock_lowres/>
    <Add mover=fa/>
  </PROTOCOLS>
</dock_design>
```

Binding-Energy Calculations:

The binding energy was defined as the difference between the total system energy in the bound and unbound states. In each state, interface residues were allowed to repack. For numerical stability, binding-energy calculations were repeated three times, and the average was taken.

The following ddg.xml script was used to execute this calculation. This script was written in "RosettaScripts" and implemented using the Rosetta modeling suite.

Example of Execution rosetta_scripts.default.linuxgccrelease -s 5_lahw_sc+lig_orig_0001.pdb -parser:protocol ddg.xml --restore_pre_talaris_2013_behavior -overwrite

```
ddg.xml script:
<dock_design>
  <SCOREFXNS>
    <sc12_w_correction weights=score12_w_corrections/>
  </SCOREFXNS>
  <FILTERS>
    <Ddg name=ddg confidence=0 repeats=3/>
  </FILTERS>
  <MOVERS>
    <AtomTree name=docking_tree docking_ft=1/>
  </MOVERS>
  <APPLY_TO_POSE>
  </APPLY_TO_POSE>
  <PROTOCOLS>
    <Add mover_name=docking_tree filter_name=ddg/>
    <Add filter_name=ddg/>
  </PROTOCOLS>
</dock_design>
```

Antibody Stability Calculations:

The stability energy was defined as the system's free energy of the antibody monomer. To assess the stability energy of the antibody the target was removed and the antibody total energy score (score12) was calculated.

The following AB_stability.xml script was used to execute this calculation. This script was written in "RosettaScripts" and implemented using the Rosetta modeling suite.

Example of Execution rosetta_scripts.default.linuxgccrelease -s 5_lahw_sc+lig_orig_0001.pdb -parser:protocol AB_stabilty.xml --restore_pre_talaris_2013_behavior -overwrite

```
AB_stability.xml script:
<dock_design>
  <SCOREFXNS>
    <sc12_w_correction weights=score12_w_corrections/>
  </SCOREFXNS>
  <MOVERS>
    <SwitchChainOrder                      name=remove_ligand scorefxn=sc12_w_correction chain_order=1/> remove the ligand before computing the antibody's stability
  </MOVERS>
  <FILTERS>
    <ScoreType    name=total_score    score_type=total_score scorefxn=sc12_w_correction threshold=100/>
```

```
    <MoveBeforeFilter                    name=antibody stability
mover=remove_ligand  filter=total_score/>  compute the antibody stability as the
total_score of the antibody in the absence of the ligand
    </FILTERS>
    <APPLY_TO_POSE>
    </APPLY_TO_POSE>
    <PROTOCOLS>
        <Add filter_name=antibody_stability/>
    </PROTOCOLS>
</dock_design>
```

Packing-Quality Assessment:

Protein packing quality at the antibody core and antibody-target interface were calculated using "RosettaHoles" (Packstat) [Sheffler & Baker, *Protein Sci* 2009, 18:229-239] implemented in Rosetta software suite, using the following Packstat.xml script. This script was written in "RosettaScripts" and implemented using the Rosetta modeling suite.

Example of Execution rosetta_scripts.default.linuxgccrelease -s 5_lahw_sc+lig_orig_0001.pdb -parser:protocol Packstat.xml - -restore_pre_talaris_2013 behavior -overwrite

```
Packstat.xml script:
<dock_design>
    <SCOREFXNS>
        <sc12_w_correction weights=score_12_w_corrections/>
    </SCOREFXNS>
    <FILTERS>
        <PackStat name=packstat threshold=0.6 repeats=3/>
    </FILTERS>
    <MOVERS>
    </MOVERS>
    <APPLY_TO_POSE>
    </APPLY_TO_POSE>
    <PROTOCOLS>
        <Add filter_name=packstat/>
    </PROTOCOLS>
</dock_design>
```

Boltzmann Conformational Probabilities of Interface Side Chains:

Boltzmann conformational probabilities were calculated as described by Pantazes and Maranas [*Protein. Eng. Des. Sel.*, 2010, 23, 849-858]. For each complex, the method first separated the partners, and for each residue that makes an appreciable contribution to binding (binding energy increases by more than 1 R.e.u. upon mutation to alanine), it iterates over all of its rotameric states as defined in the Dunbrack library of backbone-dependent rotamers excluding rotamers that are predicted to form steric clashes with protein main chain or CP atoms. For each rotamer placement, all residues within a 6 Å shell were repacked and minimized. The energy E of each such state was then evaluated using the Rosetta all-atom energy function (score12) [Kortemme & Baker, *PNAS* 2002, 99:14116-14121]. The probability of the conformation of residue i, $P_i$, is then computed assuming a Boltzmann distribution:

$$P_i = \frac{e^{\frac{-E_i}{K_B T}}}{\sum_s e^{\frac{-E_s}{K_B T}}} \quad \text{(Equation 2)}$$

wherein s is the rotameric state, $k_B$ is the Boltzmann constant, and T is the absolute temperature. $k_B T$ was set to 0.8 R.e.u. in all simulations. $E_i$ is the energy of the unbound state. The following script was written in "RosettaScripts" and implemented using the Rosetta modeling suite.

Example of Execution rosetta_scripts.default.linuxgccrelease -s 5_lahw_sc+lig_orig_0001.pdb -parser:protocol boltz_unbound.xml -restore_pre_talaris_2013 behavior -overwrite

```
boltz_unbound.xml script:
<dock_design>
    <TASKOPERATIONS>
        <ProteinInterfaceDesign name=pido repack_chain1=1
repack_chain2=0/> Change the repack_chain1 to true if you want to go
over residues in chain1
    </TASKOPERATIONS>
    <SCOREFXNS>
        <score12_W_correct weights=score12_w_corrections/>
    </SCOREFXNS>
    <FILTERS>
        <Sasa name=sasa confidence=0/>
        <Ddg name=ddg confidence=0 scorefxn=score12_W_correct
repeats=3/>
        <RotamerBoltzmannWeight name=boltz ddG_threshold=0.6
task_operations=pido jump=1 compute_entropy_reduction=1
energy_reduction_factor=1.0 scorefxn=score12_W_correct
temperature=0.8/>
    </FILTERS>
    <MOVERS>
        <AtomTree name=docking_tree docking_ft=1/>
    </MOVERS>
    <APPLY_TO_POSE>
    </APPLY_TO_POSE>
    <PROTOCOLS>
        <Add mover_name=docking_tree/>
        <Add filter_name=boltz/>
    </PROTOCOLS>
</dock_design>
```

Backbone Segment Clustering:

The antibody structures in the databases described below were aligned separately to the variable heavy and variable light domains of antibody 4m5.3, (PDB ID 1X9Q) [Lippow et al., *Nat Biotechnol* 2007, 25:1171-1176]. The coordinates of the CDRs according to $V_L$, L3, $V_H$ and H3 definitions were then extracted and clustered according to length. For L3 and H3 additional conformational clustering was performed using the Rosetta clustering application. Backbone conformations were clustered into bins of 2.0 Å RMSD as measured between Cα atoms. The resulting clusters were inspected manually for common sequence motifs. Clusters containing multiple sequence motif with corresponding backbone conformation differences were divided by decreasing the clustering bin size. Likewise, clustering bin size was increased to merge clusters in cases where multiple clusters contained the same sequence motif.

Example Command Line cluster.default.linuxgccrelease -in::file::fullatom -in:file:s *.pdb -cluster:radius 2

Generating Sequence Profiles:

For each backbone conformation cluster a Position Specific Scoring Matrix (PSSM) was generated. The amino-acid sequence was extracted from each structure to first generate a multiple sequence alignment from which 100% sequence redundancy was removed (every sequence in the alignment has at least a single amino acid difference from all other sequences in the alignment). The PSSMs were generated using the PSI-BLAST suite [Biegert & Söding, *PNAS* 2009, 106:3770-3775] with default parameters and the multiple sequence alignment as input.

The following script was written in bash and depends on two programs, "muscle" [Edgar R C. doi:10.1093/nar/gkh340. PubMed PMID: 15034147.], and "psiblast". This script was executed in the same folder as the clustered backbone segments to produce a single PSSM.

```
make_pssm.sh scrip:
for i in *.pdb; do pdb_seq.py $i; done >msa.fas
cat msa.fas ltr -d "\n" ltr ">" "\n" lawk '{print $NF}' lsort luniq lgrep
"'[A-Z]'">msa.uniq.fas
############
line=1;while read p;
do   echo ">$line" >>msa.uniq.num.fas;
echo $p >>mscaa.uniq.numfas;
line=$(expr $line + 1);
done < msa.uniq.fas
############
muscle -in msa.uniq.num.fas -out muscle.msa.uniq.num.fas
head -2 muscle.msa.uniq.num.fas >head_seq;psiblast -subject head_seq
-in_msa muscle.msa.uniq.num.fas -out_ascii_pssm cdr.PSSM
```

Algorithm Performance:

A typical trajectory took about 7 hours from submission to successful completion on a standard single CPU. The protocol is divided to two parts. First, the complex formed between the designed antibody scaffold (algorithm, section d) and the target molecule was subjected to docking, design, and optimization/minimization (algorithm, section e). The vast majority of time was spent in the downstream refinement steps (algorithm, section f). To make efficient use of computational resources, energy and structure filtering were applied before going into refinement; on average, only 4% of all trajectories passed this filtering. Depending on the availability of computational resources and the magnitude of the design problem, filters at this step can be adjusted.

Checkpointing:

A checkpointing policy was implemented that ensures that if a design trajectory is prematurely terminated it can be resumed from the last backup point. The checkpointing policy is enforced from the start of the backbone optimization procedure. A PDB-formatted file containing the coordinate information of the complex was saved to disk along with the precise design stage, complex stability, and binding energies, whenever a sampled backbone improves the objective function (algorithm, section g). When the program is initiated it automatically checks for the existence of checkpointing files. If checkpointing files are found, the computation will continue from the same point it was last stopped.

Code Flow and Modularity:

The design protocol was implemented using RosettaScripts [Fleishman et al., *PLoS One* 2011, 6:e20161] which provides a convenient user interface to all major Rosetta functionalities. This form of implementation allows the non-expert user with no previous coding knowledge complete control over all aspects of the design protocol. The protocol was intentionally modular so prospective users can add, change or remove different elements in the protocol as they see fit.

Example 1

Designed Antibody—An Exemplary Procedure

Template Antibody:

As described hereinabove, two pre-computational steps in the method, according to some embodiments of the present invention, involve creating the conformation database. The database can only be used with the arbitrary template antibody it was created for. For the results presented herein, the anti-fluorescein antibody 4m5.3 (PDB ID 1X9Q) was used; however, it is noted that any arbitrary antibody template can be used.

Generating PSSM and Backbone Conformation Database:

The first step in the procedure, according to some embodiments of the present invention, is the parsing of the source antibodies into segments and grouping the segments according to length. 788 variable light κ chains and 785 variable heavy-chain source antibody structures constituted the collection of all source antibodies that were used in the example presented below.

As discussed hereinabove, the segmentation of the Fv fragments of the source antibodies followed a division into four segments: L1-L2 (referred to as "$V_L$") and H1-H2 (referred to as "$V_H$"), each flanked by the two structurally conserved cysteines of the light and heavy variable domains, L3 and H3, each starting at the first amino acid after the second cysteine and ending at position 100 of the variable light κ domain and position 103 of the variable heavy domain (see, Table 2 below).

Table 2 below presents the structurally homologous segment type definitions used in the position-based scoring step, as well as a comparison between some widely accepted position numbering schemes.

TABLE 2

| CDR | | Kabat position numbers | Chothia position numbers | CDR definitions used for design | Segment definitions used for PSSMs and backbone modeling |
|---|---|---|---|---|---|
| VL | L1 | L24-L34 | L24-L34 | L23-L35 | L23-L88 |
|  | L2 | L50-L56 | L50-L56 | L46-L55 |  |
|  | L3 | L89-L97 | L89-L97 | L89-L100 | L89-100 |
| VH | H1 | H26-H35 | H26-H32 | H26-H37 | H25-H92 |
|  | H2 | H50-H65 | H50-H58 | H45-H58 |  |
|  | H3 | H95-H102 | H95-H102 | H93-H103 | H93-H103 |

In each segment cluster there are sequences of different lengths, hence each cluster was further divided into length groups. Within each length group further conformation clustering has been made to differentiate sequences according to the 3D conformations they encode. For each such cluster, a sequence alignment process is carried out, and each structurally homologous segment is assigned position-specific scoring matrix (PSSM), using, for example, the PSI-BLAST software package.

Table 3 below lists the segments in their length grouping scheme and denotes the PDB entry of each of the corresponding source antibody. Each of these segments was assigned a PSSM as described hereinabove.

For the generation of the backbone conformation database, all source antibody structures were superimposed on the template antibody, while using structurally significant stem positions (locations of highest structural conservation) for the conformation segments that are structurally very well aligned in all antibodies to ensure that the inserted segments can be treated as modular pieces that can be recombined arbitrarily in constructing artificial antibodies.

For each length group of each structurally homologous segment cluster ($V_L$, L3, $V_H$ and H3), backbone dihedral angles ($\Phi$, $\Psi$ and $\Omega$) were extracted from each of the source antibodies, and replace those in the corresponding segment in the template antibody with the source's dihedral angles, introducing a main-chain cut site in a randomly chosen position in the modeled segment. In other words, the structurally homologous segments from the source structure were cut at an arbitrary position, typically several positions away from the ends of the segment, placed on the template structure by superimposing the corresponding positions of highest structural conservation, and then the dihedral angles of the two halves of the segment subjected to weight fitting based on structural constrains, while simultaneously changing the amino acid sequence of the segment according to the PSSM values, as described hereinabove.

The following exemplary splice_out.xml RosettaScripts xml protocol was used to extract the dihedral angles of each of the backbone segment, namely L1-L2 ($V_L$), L3, H1-H2 ($V_H$) and H3, from each of the source antibodies and imposes them onto the template antibody.

```
splice_out.xml script:
<dock_design>
<TASKOPERATIONS>
        <InitializeFromCommandline name=init/>
            <SeqprofConsensus name=seqprofcons min_aa_probability=2
conservation_cutoff_aligned_segments=0 probability_larger_than_current=0
ignore_pose_profile_length_mismatch=1>
                <RestrictToAlignedSegments chain=1>
                    <L1 source_pdb="%%template%%" start_res=24
stop_res=42/>
                        <L2 source_pdb="%%template%%"
start_res=52 stop_res=59/>
                    <L3 source_pdb="%%template%%" "
start_res=93 stop_res=106/>
                    <H1 source_pdb="%%template%%" "
start_res=134 stop_res=147/>
                    <H2 source_pdb="%%template%%" "
start_res=157 stop_res=172/>
                    <H3 source_pdb="%%template%%" "
start_res=209 stop_res=221/>
            </RestrictToAlignedSegments>
        </TASKOPERATIONS>
    <SCOREFXNS>
        <sc12_w_correction weights=score12_W_corrections>
            <Reweight scoretype="res_type_constraint" weight=0.5/> //set score
        weight of sequence constraint
                <Reweight scoretype="coordinate_constraint" weight=1/>
                <Reweight scoretype="dihedral_constraint" weight=1/>
            </sc12_w_correction>
            <score12_chainbreak weights=score12_W_corrections>
                <Reweight scoretype=chainbreak weight=1/>
            </score12_chainbreak>
        </SCOREFXNS>
    <FILTERS>
        <ScoreType name=chainbreak_val scorefxn=score12_chainbreak
    score_type=chainbreak threshold=0.5/>
        </FILTERS>
        <MOVERS>
                <Splice name=splice
loop_pdb_source="%%source%%" source_pdb="%%source%%"
loop_dbase_file_name="L1_L2.db" scorefxn=sc12_w_correction ccd=1
randomize_cut=1 cut_secondarystruc=0 from_res=25 to_res=90 rms_cutoff=1
    splice_filter=chainbreak_val template_file="%%template%%"
design_task_operations=init,seqprofcons design=1 segment=L1_L2
protein_family=antibodies/>
        </MOVERS>
        <APPLY_TO_POSE>
        </APPLY_TO_POSE>
        <PROTOCOLS>
            <Add mover=splice/>
        </PROTOCOLS>
    </dock_design>
Command line options (can be wrapped in a "flag" file)
    -linmem_ig 10
    -ex1
    -ex2aro
    -use_input_sc
    -extrachi_cutoff 8
    -ignore_unrecognized_res
    a UpperDNA Cterm_amidation SpecialRotamer VirtualBB ShoveBB
```

-continued

```
VirtualDNAPhosphate VirtualNTerm CTermConnect sc_orbitals
pro_hydroxylated_case1 pro_hydroxylated_case2 ser_phosphorylated
thr_phosphorylated tyr_phosphorylated tyr_sulfated lys_dimethylated
lys_monomethylated lys_trimethylated lys_acetylated glu_carboxylated cys_acetylated
tyr_diiodinated N_acetylated C_methylamidated MethylatedProteinCterm
    -jd2:ntrials 10
    -max_retry_job 11
    -parser:protocol splice_out.xml
    -restore_pre_talaris_2013_behavior
    -pdb_comments_true
    -mute all
    -parser:script_vars source=<source antibody PDB file>
    -parser:script_vars template=<template antibody PDB file>
    -s <template input PDB file>
```

Execution Example:

Rosetta_scripts.default.linuxgccrelease -s 1x9q.pdb @flags -parser:script_vars source=1AHW.pdb -parser:script_vars template=1x9q.pdb Notice that the last three flags were moved out of the flag file to the command line. Also, for this part of the protocol the input PDB file (denoted by the -s flag in the command line) should be the same as the template pdb.

The Following Parameters can be Changed for Different Segments:

The source antibody PDB can be aligned to the variable heavy domain when extracting the H1_H2, H3 segments, or the variable light domain, when extracting the L1_L2, L3 segments of the template antibody before executing "splice_out.xml".

loop_dbase_file_name—Meaningful name should be given associating the database file with correct segment.

From_res/to_res—Should be the start and end residue numbers of the template antibody structure.

Segment—Change this to one of four available antibody segments (L1_L2,L3,H1_H2, and H3)

TABLE 3

| Segment | Position span | PDB IDs |
|---|---|---|
| $V_L$ (L1-L2) | L1.10_L2.8 | 1E6J 1A6T 1AD0 1BAF 1BQL 1E6O 1EO8 1FOR 1MHP 1OTS 1OTT 1OTU 1SY6 1V7M 1V7N 1WC7 1WCB 1YQV 1Z3G 2BMK 2EXW 2EXY 2EZ0 2FAT 2FBJ 2FEC 2FED 2FEE 2H2P 2H2S 2HLF 2HT2 2HT3 2HT4 2HTK 2HTL 2HWZ 2IFF 2OSL 2W9E 2Z91 2Z92 2Z93 2ZKH 3AB0 3BKY 3BT2 3C09 3DET 3EJY 3EJZ 3HFL 3I50 3IU3 3IXT 3MCL 3NCY 3NFP |
| | L1.11_L2.8 | 12E8 1A0Q 1A2Y 1A7N 1A70 1A7P 1A7Q 1A7R 1AHW 1AJ7 1B2W 1BBJ 1BJ1 1BZ7 1CE1 1CFQ 1CFS 1CFT 1CZ8 1D5B 1DFB 1DQ1 1DQM 1DQQ 1EAP 1EMT 1EZV 1F6L 1FAI 1FBI 1FDL 1FGV 1FJ1 1FSK 1FVC 1FVD 1FVE 1G9M 1G9N 1HEZ 1HH6 1HH9 1H16 1HYS 1I8M 1IGC 1IGM 1IKF 1IVL 1J5O 1JHL 1JPS 1JPT 1K4C 1K4D 1K6Q 1LK3 1MAM 1MLB 1MLC 1MQK 1N5Y 1N6Q 1N8Z 1NBY 1NBZ 1NCA 1NCB 1NCC 1NCD 1NDG 1NDM 1NGW 1NGX 1NGY 1OM3 1OP3 1OP5 1OPG 1P2C 1P7K 1QLE 1QP1 1R0A 1R24 1R3I 1R3J 1R3K 1R3L 1REI 1RIH 1RZ7 1RZ8 1RZG 1RZI 1RZJ 1RZK 1S5H 1S78 1T03 1T04 1T3F 1TJG 1TJH 1TJI 1TXV 1TY3 1TY5 1TY6 1TY7 1TZH 1TZI 1U8H 1U8I 1U8J 1U8K 1U8L 1U8M 1U8N 1U8O 1U8P 1U8Q 1U91 1U92 1U93 1U95 1UJ3 1UYW 1VFA 1VFB 1WEJ 1WTL 1XF2 1XF3 1XF4 1XGP 1XGQ 1XIW 1YJD 1YY8 1YY9 1ZA3 1ZAN 1ZLS 1ZLU 1ZLV 1ZLW 1ZTX 1ZWI 2A6D 2ADG 2ADI 2ADJ 2AEP 2AEQ 2AJ3 2ARJ 2ATK 2BDN 2BOB 2BOC 2BX5 2D7T 2DTG 2DWD 2DWE 2ESG 2E19 2F5A 2F5B 2FGW 2FJF 2FJG 2FJH 2FR4 2GFB 2H8P 2H9G 2HFE 2HFG 2HG5 2HJF 2HVJ 2HVK 2I5Y 2I60 2IBZ 2IH1 2IH3 2ITC 2ITD 2NLJ 2NR6 2OSP 2OZ4 2Q1E 2Q76 2Q8A 2Q8B 2QAD 2QQK 2QQL 2QQN 2QR0 2R0K 2R0L 2R4R 2R4S 2R56 2R8S 2VC2 2VDK 2VDL 2VDM 2VDN 2VDO 2VDP 2VDQ 2VDR 2WUB 2WUC 2X7L 2XRA 3B2U 3B2V 3BN9 3BQU 3CDC 3CDF 3CFD 3CFE 3CLE 3CLF 3CMO 3CVH 3CXD 3D85 3D9A 3DRO 3DSF 3DVF 3DVG 3DVN 3EO9 3EOA 3EOB 3ESU 3ESV 3ET9 3ETB 3F5W 3F7V 3F7Y 3FB5 3FB6 3FB7 3FB8 3FMG 3FZU 3G6J 3GB7 3GK8 3GRW 3HFM 3HI5 3HI6 3HMW 3HMX 3HNS 3HNT 3HNV 3HPL 3I9G 3IDG 3IDI 3IDJ 3IDM 3IDN 3IDX 3IDY 3IGA 3IU4 3IVK 3IY0 3IY1 3IY2 3IY6 3IY7 3JWD 3JWO 3K2U 3KJ6 3KR3 3KYK 3L5W 3L5X 3L5Y 3L7E 3L7F 3L95 3LEV 3LIZ 3LOH 3MOA 3MOB 3MOD 3MXV 3MXW 3NID 3NIF 3NIG 3OOR 3OAU 3OAY 3OB0 3OR6 3OR7 3PNW 4IJ3 6FAB |
| | L1.12_L2.8 | 15C8 1AIF 1CF8 1DN0 1FIG 1HQ4 1HZH 1IQD 1KEN 1N0X 1ORQ 1ORS 1RHH 1U6A 2AGJ 2B4C 2BRR 2NY7 2V7N 3EO0 3EO1 3EOT 3HI1 3IY5 3LS4 3LS5 |
| | L1.15_L2.8 | 1ACY 1AFV 1AI1 1EGJ 1F11 1F58 1GGB 1GGC 1GGI 1H0D 1IBG 1IQW 1IT9 1J05 1NSN 1QNZ 2AAB 2F58 2GCY 2GSI 2R29 3BDY 3BE1 3E8U 3I2C 3IY4 3O41 3O45 |
| | L1.16_L2.8 | 1A3L 1AD9 1AE6 1BLN 1C1E 1CGS 1CL7 1CR9 1CU4 1DBA 1DBB 1DBJ 1DBK 1DBM 1F8T 1FL3 1FPT 1IGF 1IGI 1IGJ 1JGU 1JGV 1KFA 1KN2 1KN4 1KTR 1L7T 1LO0 1LO2 1LO3 1LO4 1M71 1M7D 1M7I 1MNU 1MRC 1MRD 1MRE 1MRF 1NBV 1PZ5 1QFU 1QYG 1RFD 1RIU 1RIV 1RMF 1RU9 1RUA 1RUK 1RUL 1RUM 1RUQ 1RUR 1S3K 1T66 1TET 1TQB 1TQC 1UZ6 1UZ8 1X9Q 1XGY 1YEI 1YEJ 1YEK 1YNK 1YNL 2A1W 2A77 2AI0 2CGR 2D03 2DBL 2DDQ 2EH7 2EH8 2G2R 2G60 2GJZ 2GK0 2HKF 2HKH 2IGF 2IPU 2IQ9 2IQA 2JEL 2R0W 2R0Z 2Z4Q 3BAE 3BKC 3BKJ 3BKM 3BZ4 3C5S 3C6S 3CFC 3EYS 3EYU 3EYV 3FO0 3FO1 3FO2 3FO9 3GGW 3HR5 3IET 3IF1 3IFP 3LEX 3LEY 4FAB |
| | L1.17_L2.8 | 1A3R 1A5F 1BBD 1CK0 1EFQ 1FRG 1GM3 1HIL 1HIN 1IFH 1IL1 1MCP 1MHH 1MVU 1N64 1NLB 1Q9K 1Q9L 1Q9O 1Q9Q 1Q9R 1Q9T 1Q9V 1Q9W 1T4K 1XCQ 1XCT 1XF5 1YMH 2AP2 2CK0 2DTG 2G5B 2I9L 2IMM 2MCP 2R1W 2R1X 2R1Y 2R23 2R2B 2R2E 2R2H 2ZUQ 3BPC 3CK0 3CSY 3GI8 3GI9 3HZK 3HZM 3HZV 3HZY 3I02 3IJH 3IJS 3IJY 3IKC 3INU 3KJ4 3LD8 3LDB 3LOH 3MBX 3MNV 3MNW 3MNZ 3MO1 3NTC 3O2D 43C9 43CA |

TABLE 3-continued

| Segment | Position span | PDB IDs |
|---|---|---|
| L3 | L3.10.1 | 12E8 15C8 1A2Y 1A3L 1A3R 1A4J 1A4K 1A5F 1A6T 1A7N 1A7P 1A7Q 1A7R 1ACY 1AD0 1AD9 1AE6 1AFV 1AHW 1AI1 1AIF 1AJ7 1AXS 1AXT 1AY1 1B0W 1B2W 1B6D 1BBD 1BBJ 1BFV 1BJ1 1BLN 1BM3 1BWW 1BZ7 1C12 1C1E 1C5C 1CBV 1CE1 1CF8 1CFQ 1CFS 1CFT 1CFV 1CGS 1CIC 1CL7 1CLO 1CR9 1CT8 1CU4 1CZ8 1D5B 1D5I 1D6V 1DBA 1DBB 1DBJ 1DBK 1DBM 1DEE 1DLF 1DN0 1DQD 1DQJ 1DQM 1DQQ 1DSF 1DVF 1E4X 1EFQ 1EGJ 1EMT 1EZV 1F11 1F3D 1F58 1F6L 1F8T 1FAI 1FDL 1FE8 1FGN 1FGV 1FIG 1FJ1 1FL3 1FL5 1FLR 1FNS 1FOR 1FPT 1FRG 1FSK 1FVC 1FVD 1FVE 1G7H 1G7I 1G7J 1G7L 1G7M 1GAF 1GGB 1GGC 1GGI 1GHF 1GPO 1H0D 1H8N 1HEZ 1HH6 1HH9 1HI6 1HIL 1HIN 1HQ4 1HYS 1HZH 1I3G 1I8K 1I8M 1I9J 1IBG 1IFH 1IGC 1IGF 1IGI 1IGJ 1IGM 1IKF 1IQD 1IQW 1IT9 1IVL 1J05 1J1O 1J1P 1J1X 1J5O 1JFQ 1JGL 1JHL 1JPS 1JPT 1JV5 1K4C 1K4D 1K6Q 1KB5 1KCS 1KCU 1KCV 1KEN 1KEA 1KIR 1KN2 1KN4 1L7I 1L7T 1LK3 1LOO 1LO2 1LO3 1LO4 1MAJ 1MAK 1MAM 1MCP 1MEX 1MHH 1MHP 1MIE 1MJ7 1MJU 1MLB 1MLC 1MNU 1MOE 1MRC 1MRD 1MRE 1MRF 1MVU 1N0X 1N4X 1N5Y 1N64 1N6Q 1N8Z 1NAK 1NBV 1NBY 1NBZ 1NCA 1NCB 1NCC 1NCD 1NCW 1NDG 1NDM 1NGW 1NGX 1NGY 1NGZ 1NLB 1NMB 1NSN 1OPG 1ORQ 1OSP 1OTS 1OTT 1OTU 1P2C 1P7K 1Q72 1QFU 1QNZ 1QP1 1QYG 1R0A 1R24 1R3I 1R3J 1R3K 1R3L 1REI 1RFD 1 RHH 1RIH 1RIU 1RIV 1RJL 1RMF 1RU9 1RUA 1RUK 1RUL 1RUM 1RUQ 1RUR 1RZG 1RZI 1S3K 1S5H 1S78 1SBS 1SEQ 1SVZ 1SY6 1T03 1T04 1T2Q 1T3F 1T66 1TET 1TJG 1TJH 1TJI 1TPX 1TQB 1TQC 1TXV 1TY3 1TY5 1TY6 1TY7 1TZI 1U6A 1U8H 1U8I 1U8J 1U8K 1U8L 1U8M 1U8N 1U8O 1U8P 1U8Q 1U91 1U92 1U93 1U95 1UCB 1UJ3 1UM5 1UWE 1UWG 1UWX 1UYW 1UZ6 1UZ8 1V7M 1V7N 1VFA 1VFB 1VGE 1VPO 1WC7 1WCB 1WEJ 1WT5 1WTL 1X9Q 1XCQ 1XCT 1XF2 1XF3 1XF4 1XF5 1XGP 1XGQ 1XGY 1XIW 1YEC 1YEE 1YEI 1YEJ 1YEK 1YJD 1YMH 1YNK 1YNL 1YY8 1YY9 1Z3G 1ZAN 1ZEA 1ZTX 1ZWI 2A1W 2A6D 2A61 2A77 2AAB 2ADG 2ADI 2ADJ 2AEP 2AEQ 2AGJ 2AI0 2AJ3 2AJV 2AP2 2ARJ 2ATK 2B2X 2B4C 2BDN 2BMK 2BOB 2BOC 2BRR 2BX5 2C1P 2CGR 2CJU 2CMR 2D03 2D7T 2DBL 2DDQ 2DQI 2DQU 2DWD 2DWE 2E27 2EH7 2EH8 2EIZ 2EXW 2EXY 2EZ0 2E19 2E58 2F5A 2F5B 2FBJ 2FEC 2FED 2FEE 2FGW 2FJF 2FJG 2FJH 2FR4 2FX7 2G2B 2G60 2GCY 2GFB 2GJJ 2GJZ 2GK0 2GSI 2H2P 2H25 2H8P 2H9G 2HFE 2HFF 2HFG 2HG5 2HJF 2HKF 2HKH 2HLF 2HRP 2HT2 2HT3 2HT4 2HTK 2HTL 2HVJ 2HVK 2HWZ 2IBZ 2IGF 2IH1 2IH3 2IMM 2IMN 2IPU 2IQ9 2IQA 2ITC 2ITD 2J4W 2JEL 2MCP 2NLJ 2NR6 2NY7 2NYY 2OK0 2OSL 2OSP 2OZ4 2PCP 2PR4 2Q1E 2Q20 2Q76 2Q8A 2Q8B 2QAD 2QQK 2QQL 2QQN 2R0K 2R0L 2R0W 2R0Z 2R29 2R4R 2R4S 2R56 2R8S 2RCS 2UYL 2UZI 2V17 2VC2 2VDK 2VDL 2VDM 2VDN 2VDO 2VDP 2VDQ 2VDR 2VL5 2W9D 2W9E 2WUB 2WUC 2Z4Q 2Z91 2Z92 2Z93 2ZKH 35C8 3AB0 3B2U 3B2V 3BAE 3BD3 3BDY 3BE1 3BKC 3BKJ 3BKM 3BKY 3BN9 3BZ4 3C08 3C09 3C5S 3C6S 3CDC 3CDF 3CFB 3CFC 3CFD 3CFE 3CLE 3CLF 3CSY 3CVH 3CX5 3CXD 3D85 3D9A 3DET 3DIF 3DRO 3DSF 3DVF 3E8U 3EJY 3EJZ 3EO0 3EO1 3EO9 3EOA 3EOB 3ESU 3ESV 3ET9 3ETB 3EYS 3EYU 3EYV 3F5W 3F7V 3F7Y 3FB5 3FB6 3FB7 3FB8 3FMG 3FO0 3FO1 3FO2 3FO9 3FZU 3G6J 3GB7 3GGW 3GI8 3GI9 3GK8 3GNM 3GRW 3HC4 3HFM 3HI1 3HMW 3HMX 3HNS 3HNT 3HNV 3HPL 3HR5 3I2C 3I50 3I9G 3IDG 3IDI 3IDJ 3IDM 3IDN 3IDX 3IDY 3IFL 3IFN 3IFO 3IFP 3IGA 3INU 3IU4 3IVK 3IXT 3IY0 3IY1 3IY2 3IY4 3IY5 3IY6 3K2U 3KJ6 3KR3 3KYK 3L5W 3L5X 3L7E 3L7F 3L95 3LD8 3LDB 3LEV 3LEX 3LEY 3LIZ 3LOH 3LS4 3LS5 3MBX 3MNV 3MNW 3MNZ 3MO1 3MOA 3MOB 3MOD 3MXV 3MXW 3NCY 3NFP 3NID 3NIF 3NIG 3NTC 3O0R 3O41 3O45 3OR6 3OR7 43C9 43CA 4FAB 4IJ3 4LVE 5LVE 6FAB |
| | L3.10.3 | 1OM3 1OP3 1OP5 1ZLS 1ZLU 1ZLV 1ZLW 3OAU 3OAY 3OAZ 3OB0 8FAB |
| | L3.10.4 | 1KEL |
| | L3.11.1 | 1JGU 1JGV |
| | L3.11.2 | 1MQK1QLE |
| | L3.11.3 | 1I7Z |
| | L3.11.4 | 1BAF |
| | L3.11.5 | 1A8J |
| | L3.11.6 | 2XRA |
| | L3.12.1 | 1G9M 1G9N 1RZ8 1RZJ 1RZK 2L5Y 2I60 |
| | L3.12.2 | 3DVG 3PNW |
| | L3.12.3 | 3DVN |
| | L3.12.4 | 3KDM |
| | L3.12.5 | 2QR0 |
| | L3.13.1 | 2X7L |
| | L3.13.2 | 3GBN |
| | L3.8.1 | 1DFB 1MIM 3IU3 |
| | L3.9.1 | 1A0Q 1A7O 1BQL 1C5D 1CK0 1DQL 1E6O 1EAP 1EO8 1GM3 1H3P 1IL1 1KEG 1M71 1M7D 1M7I 1ORS 1PZ5 1Q9K 1Q9L 1Q9O 1Q9Q 1Q9R 1Q9T 1Q9V 1Q9W 1QKZ 1RZ7 1T4K 1TZH 1YQV 1ZA3 2ADF 2CK0 2DTG 2FAT 2G5B 2I9L 2IFF 2J88 2R1W 2R1X 2R1Y 2R23 2R2B 2R2E 2R2H 2ZUQ 3BPC 3BT2 3CK0 3CMO 3DGG 3HFL 3HI5 3HI6 3HZK 3HZM 3HZV 3HZY 3I02 3IET 3IF1 3IJH 3IJS 3IJY 3IKC 3IY7 3JWD 3JWO 3KJ4 3L5Y 3O2D 3OZ9 |
| | L3.9.2 | 3MCL |
| VH (H1-H2) | H1.13_H2.15 | 1GHF 3IY2 |
| | H1.14_H2.14 | 1A2Y 1A7N 1A7Q 1A7R 1C5D 1DN0 1DQD 1DQJ 1DQM 1DQQ 1FDL 1FE8 1FL3 1FNS 1GPO 1I9J 1IBG 1JGU 1JGV 1KFA 1L7T 1LOO 1LO2 1LO3 1LO4 1MHP 1NAK 1NBY 1NDG 1NDM 1OSP 1T2Q 1T4K 1U6A 1VFA 1VFB 1XGP 1XGQ 1YY8 1YY9 1ZAN 2AJ3 2ARJ 2B2X 2DQU 2EIZ 2FJG 2GJZ 2R8S 3AB0 3CFB 3CFC 3D9A 3FO0 3FO1 3FO2 3HFM 3HI1 3IY6 3IY7 3LD8 3LDB 3LS4 3LS5 3NCY 43C9 43CA 4IJ3 |
| | H1.14_H2.15 | 12E8 15C8 1A3L 1A3R 1A4J 1A6T 1AD9 1AE6 1AFV 1AHW 1AJ7 1B2W 1BBD 1BBJ 1BJ1 1BLN 1BQL 1BZ7 1C1E 1C5C 1CFQ 1CFS 1CFT 1CFV 1CGS 1CIC 1CR9 1CT8 1CU4 1CZ8 1D5B 1D5I 1D6V 1DBA 1DBB 1DBJ 1DBK 1DBM 1DEE 1DFB 1DQL 1DSF 1DVF 1E4X 1E6J 1E6O 1EAP 1EMT 1EO8 1F11 1F3D 1FAI 1FBI 1FGN 1FIG 1FJ1 1FOR 1FPT 1FRG 1FSK 1FVC 1FVD 1FVE 1G9M 1G9N 1GAF 1GM3 1H0D 1H3P 1H8N 1HEZ 1HH6 1HH9 1HI6 1HIL 1HIN 1HZH 1I7Z 1I8K 1I8M 1IFH 1IGC 1IGF 1IGI 1IGJ 1IGM 1IKF 1IL1 |

TABLE 3-continued

| Segment | Position span | PDB IDs |
|---|---|---|
| | | 1IQD 1IQW 1IT9 1J05 1JFQ 1JHL 1JPS 1JPT 1JV5 1K4C 1K4D 1K6Q 1KB5 1KEG 1KN2 1KN4 1L7I 1LK3 1MEX 1MHH 1MIM 1MJU 1MLB 1MLC 1MNU 1MOE 1MQK 1MRD 1MRE 1MRF 1MVU 1N0X 1N4X 1N64 1N8Z 1NCA 1NCB 1NCC 1NCD 1NGW 1NGX 1NGY 1NGZ 1NLB 1NMB 1OM3 1OP3 1OP5 1OPG 1OTS 1OTT 1OTU 1P2C 1P7K 1QFU 1QKZ 1QLE 1QNZ 1R24 1R3I 1R3J 1R3K 1R3L 1RHH 1RIH 1RJL 1RMF 1RUQ 1RUR 1RZ7 1RZ8 1RZJ 1RZK 1S3K 1S5H 1S78 1SEQ 1SVZ 1SY6 1T04 1T3F 1TET 1TPX 1TQB 1TQC 1TXV 1TY3 1TY5 1TY6 1TY7 1TZH 1TZI 1UCB 1UJ3 1UM5 1UWE 1UWG 1UWX 1UYW 1UZ6 1UZ8 1VGE 1WEJ 1WT5 1XCQ 1XCT 1XF2 1XF5 1XGY 1XIW 1YEE 1YEJ 1YEK 1YJD 1YMH 1YNK 1YNL 1YQV 1Z3G 1ZA3 1ZEA 1ZLS 1ZLU 1ZLV 1ZLW 1ZTX 1ZWI 2A1W 2A6D 2A6I 2AAB 2ADF 2ADG 2ADI 2ADJ 2AI0 2AP2 2ATK 2BDN 2BOB 2BOC 2BRR 2C1P 2CGR 2CMR 2D7T 2DBL 2DDQ 2DWD 2DWE 2EH7 2EXW 2EXY 2EZ0 2F19 2FAT 2FBJ 2FEC 2FED 2FEE 2FJF 2FJH 2FR4 2FX7 2G2R 2G60 2GCY 2GFB 2GJJ 2GSI 2H2P 2H2S 2H8P 2H9G 2HFE 2HFG 2HG5 2HJF 2HLF 2HRP 2HT2 2HT3 2HT4 2HTK 2HTL 2HVJ 2HVK 2I5Y 2I60 2I9L 2IFF 2IGF 2IH1 2IH3 2ITC 2ITD 2J4W 2JEL 2NLJ 2NR6 2NY7 2NYY 2OSL 2OZ4 2PCP 2Q76 2Q8A 2Q8B 2QQK 2QQL 2QQN 2QR0 2R0K 2R0L 2R29 2R4R 2R4S 2R56 2RCS 2UYL 2UZI 2VC2 2VDK 2VDL 2VDM 2VDN 2VDO 2VDP 2VDQ 2VDR 2W9D 2W9E 2WUB 2WUC 2X7L 2XRA 2Z4Q 2ZUQ 35C8 3BE1 3BKY 3BN9 3BT2 3C09 3CLE 3CLF 3CMO 3CVH 3D85 3DET 3DGG 3DIF 3DVG 3DVN 3E8U 3EJY 3EJZ 3EO0 3EO1 3EOA 3EOB 3ESV 3ET9 3ETB 3EYV 3F5W 3F7V 3F7Y 3FB5 3FB6 3FB7 3FB8 3FMG 3G6J 3GB7 3GBN 3GI8 3GI9 3GK8 3GNM 3GRW 3HC4 3HFL 3HI5 3HI6 3HMW 3HMX 3HNS 3HNT 3HNV 3HPL 3HR5 3I9G 3IDX 3IDY 3IGA 3INU 3IU3 3IVK 3IY0 3IY1 3IY4 3JWD 3JWO 3K2U 3KDM 3KJ6 3KR3 3KYK 3L95 3LIZ 3MCL 3MNV 3MNW 3MNZ 3MO1 3MXV 3MXW 3NFP 3NGB 3NID 3NIF 3NIG 3NTC 3O0R 3O2D 3OAU 3OAY 3OAZ 3OB0 3OR6 3OR7 3OZ9 3PNW 6FAB 8FAB |
| | H1.14_H2.17 | 1AD0 1AIF 1AXT 1CBV 1CE1 1CK0 1CLO 1DLF 1FLR 1KEL 1M7D 1M7I 1MAM 1MCP 1NBV 1PZ5 1Q72 1Q9K 1Q9L 1Q9O 1Q9Q 1Q9T 1Q9V 1QYG 1RFD 1RIU 1RIV 1SBS 1T66 1V7M 1V7N 1WC7 1WCB 1X9Q 2AEP 2AEQ 2BMK 2CJU 2CK0 2G5B 2HKF 2HKH 2MCP 2R1W 2R1X 2R1Y 2R23 2R2B 2R2E 2R2H 2V17 2ZKH 3BPC 3BZ4 3C5S 3CK0 3CXD 3DSF 3FO9 3GGW 3HZK 3HZM 3HZV 3HZY 3I02 3I2C 3I50 3IET 3IF1 3IJH 3IJS 3IJY 3IKC 3IY5 4FAB |
| | H1.15_H2.14 | 1BAF 1CF8 1EZV 1F58 1F8T 1HQ4 1KCU 1KCV 1NCW 1ORQ 1ORS 1RU9 1RUA 1RUK 1RUL 1RUM 2AJV 2F58 2IBZ 2Z91 2Z92 2Z93 3CFD 3CFE 3CX5 3LEX 3LEY |
| | H1.15_H2.15 | 1AY1 1KEN |
| | H1.16_H2.14 | 1ACY 1AI1 1GGB 1GGC 1GGI 1HYS 1J5O 1N5Y 1N6Q 1R0A 1T03 1TJG 1TJH 1TJI 1U8H 1U8I 1U8J 1U8K 1U8L 1U8M 1U8N 1U8O 1U8P 1U8Q 1U91 1U92 1U93 1U95 2AGJ 2F5A 2F5B 2HWZ 2IPU 2IQ9 2R0W 2R0Z 3B2U 3B2V 3BAE 3BKC 3BKJ 3BKM 3EYS 3EYU 3IDG 3IDJ 3IDM 3IDN 3IFL 3IFN 3IFO 3IFP 3IXT 3L5W 3L5X 3L5Y 3L7E 3L7F 3LEV 3MBX 3MOA 3MOB 3MOD 3O41 3O45 |
| | H1.16_H2.15 | 3FZU |
| H3 | H3.11.1 | 1C5C 1CFQ 1CFS 1CFT 1H8N 1HH6 1HH9 1HI6 1I3G |
| | H3.11.2 | 2Q8A 2Q8B |
| | H3.12.1 | 1EMT 1FJ1 1TPX 1TQB 1TQC 2DDQ 2R4R 2R4S 3BZ4 3C5S 3GGW 3KJ6 3MNV 3MNW 3MNZ 3MO1 |
| | H3.13.1 | 1CR9 1CU4 1DL7 1E4X 1MEX |
| | H3.13.2 | 1AJ7 1BBJ 1DQJ 1DQM 1DQQ 1GAF 1GGB 1GGC 1GGI 1GPO 1HKL 1IC4 1IC5 1IC7 1IND 1INE 1KTR 1NAK 1NBY 1NDG 1NDM 1NGW 1NGY 1P4B 1P4I 1UAC 1V7M 1V7N 1XGP 1XGQ 1XGR 1XGT 1XGU 2DQC 2DQD 2DQE 2DQF 2DQG 2DQH 2EIZ 2OZ4 2RCS 2ZKH 3CXD 3D9A 3DSF 3HFM |
| | H3.13.3 | 1NGX |
| | H3.13.4 | 1NGZ |
| | H3.14.1 | 1BAF 1Z3G 2EH7 2UZI |
| | H3.14.2 | 1FL3 3CFB 3CFC |
| | H3.14.3 | 1SM3 |
| | H3.14.4 | 3D85 |
| | H3.14.5 | 1F3D |
| | H3.14.6 | 3B9K |
| | H3.15.1 | 1BQL 1GM3 1H3P 1KCV 1P2C 1T2J 1YQV 2C1P 2IFF 3FZU 3HFL |
| | H3.15.10 | 1KCV |
| | H3.15.11 | 1T2J |
| | H3.15.2 | 1CF8 1DZB 1HQ4 1MRC 1MRD 1MRE 1MRF |
| | H3.15.3 | 2Z91 2Z92 2Z93 |
| | H3.15.4 | 1CGS 1FE8 1GHF 1KC5 1KCU 1MCO 1MLB 1MLC 1TET 1YNK 1YNL 1ZEA 2CGR 2D7T 2NR6 2Q76 2R29 2ZPK 3HC4 3IY1 3NFP 3NFS |
| | H3.15.5 | 3LEX 3LEY |
| | H3.15.6 | 3IET 3IFI |
| | H3.15.7 | 1JGL 1JHK 1OB1 1RUP 2JK5 2PW1 2PW2 2W0F 3BSZ 3D0L 3D0V 3HC0 3HC3 3I75 |
| | H3.15.8 | 1AXT 1FLR 1MJU 1T66 1X9Q 2J88 2W9D 2W9E 3FO9 4FAB |
| | H3.15.9 | 2RGS |
| | H3.16.1 | 1B2W 1CIC 1HCV 2BDN 2GHW 3AB0 |
| | H3.16.2 | 1FL5 1IQD 1XGY 2R0K |
| | H3.16.3 | 1KEL 2G60 2HKF |
| | H3.16.4 | 1MAM 1UZ6 1UZ8 |
| | H3.16.5 | 1A2Y 1A6T 1A7N 1A7Q 1A7R 1AHW 1F4W 1F4X 1F4Y 1FDL 1FGN 1JPS 1JPT 1K6Q 1KIP 1KIQ 1MIM 1T04 1T3F 1UJ3 1VFA 1VFB 2PCP 2R0L 2WUB 2WUC 3E8U 3HR5 3IU3 |
| | H3.16.6 | 1UWE 1UWG |
| | H3.16.7 | 2HKH |
| | H3.16.8 | 1WEJ |
| | H3.16.9 | 1I7Z |
| | H3.17.1 | 1CK0 1JHL 1K4C 1K4D 1MFA 1MFB 1MFC 1MFD 1MHH 1MQK 1N64 1NLB 1ORQ 1ORS 1QLE 1R3I 1R3J 1R3K 1R3L 1S5H 1XCQ 1XCT 1XF5 1YMH 1YNT 1YUH 1ZWI 2AEP 2AEQ 2ATK |

TABLE 3-continued

| Segment | Position span PDB IDs |
|---|---|
| | 2BOB 2BOC 2CK0 2DD8 2DWD 2DWE 2FBJ 2G75 2GCY 2GSG 2H8P 2HFE 2HG5 2HJF 2HVJ 2HVK 2IH1 2IH3 2ITC 2ITD 2NLJ 2NYY 2OTU 2QR0 3CK0 3F5W 3F7V 3F7Y 3FB5 3FB6 3FB7 3FB8 3FFD 3GB7 3HPL 3I2C 3IGA 3IY4 3LS4 3LS5 3NTC 3OR6 3OR7 7FAB |
| H3.17.2 | 1DN2 1L6X 1OQO 1OQX |
| H3.17.3 | 1C5D 1CT8 1FSK 1JV5 1M7D 1M7I 1PZ5 1UM5 1WT5 2ADF 2ARJ 2FAT 2FD6 2JEL 2OK0 2Z4Q 3BT2 3CLE 3CLF 3GNM 3HNS 3HNT 3HNV 3K2U |
| H3.17.4 | 1F8T 1T4K |
| H3.17.5 | 1A3R 1BBD |
| H3.17.6 | 1EO8 |
| H3.17.7 | 2G2R |
| H3.18.1 | 1AD0 1AIF 1BFO 1BLN 1CE1 1CLO 1CLY 1IGF 1KB5 1L7I 1LK3 1MHP 1NBV 1RMF 1S3K 1S78 1TXV 1TY3 1TY5 1TY6 1TY7 1UCB 1ZTX 2B2X 2CJU 2GFB 2H32 2I9L 2IGF 2UYL 2V7N 2VC2 2VDK 2VDL 2VDM 2VDN 2VDO 2VDP 2VDQ 2VDR 3ET9 3ETB 3EYV 3GJE 3GJF 3HAE 3IY2 3IY5 3KYK 3L95 3MXW 3NID 3NIF 3NIG 3OZ9 43C9 43CA 4IJ3 |
| H3.18.10 | 1RMF 2V7N |
| H3.18.11 | 1KB5 1LK3 |
| H3.18.12 | 1MHP 2B2X |
| H3.18.13 | 1AIF 3IY5 |
| H3.18.14 | 43C9 43CA |
| H3.18.15 | 1TXV 1TY3 1TY5 1TY6 1TY7 2VC2 2VDK 2VDL 2VDM 2VDN 2VDO 2VDP 2VDQ 2VDR 3NID 3NIF 3NIG |
| H3.18.16 | 1BFO 1BLN 1CE1 1CLY 1NBV 1S3K 1UCB 2CJU 2UYL 3EYV |
| H3.18.17 | 1IGF 1ZTX 2H32 2I9L 2IGF 3ET9 3ETB 3KYK 3L95 3MXW |
| H3.18.18 | 2GFB |
| H3.18.19 | 3IY2 |
| H3.18.2 | 1CBV 1DLF 1FIG 1Q72 1QNZ 1QYG 1RFD 1RIU 1RIV 2AGJ 2AJV 2X7L 3DIF 3H0T 3I50 3MXV |
| H3.18.20 | 2X7L |
| H3.18.21 | 3MXV |
| H3.18.22 | 3I50 |
| H3.18.23 | 1CBV |
| H3.18.24 | 3H0T |
| H3.18.25 | 1QNZ |
| H3.18.26 | 1FIG |
| H3.18.27 | 3DIF |
| H3.18.28 | 2AJV |
| H3.18.29 | 1DLF |
| H3.18.3 | 15C8 1EAP 1MH5 1MJ8 1NCW 1RU9 1RUA 1RUK 1RUL 1RUM 1YC7 35C8 3LIZ |
| H3.18.30 | 1YC7 |
| H3.18.31 | 1MH5 |
| H3.18.32 | 1MJ8 |
| H3.18.33 | 3LIZ |
| H3.18.34 | 15C8 |
| H3.18.35 | 1EAP |
| H3.18.36 | 35C8 |
| H3.18.4 | 1LO0 1LO2 1LO3 1LO4 2HWZ |
| H3.18.5 | 1A3L 1I9J 1L7T 1RUQ 1RUR |
| H3.18.6 | 1F11 1RZ7 3JWD 3JWO 3MCL |
| H3.18.7 | 1A4J 1AY1 1C1E 1CFV 1DBA 1DBB 1DBJ 1DBK 1DBM 1FOR 1IGI 1IGJ 1JGU 1JGV 1Q0X 1Q0Y 1QKZ 1SY6 1T2Q 1UYW 2CMR 2DBL 2O5X 2ZUQ 3DGG 3ESV 3HMW 3HMX 3IXT 3LD8 3LDB |
| H3.18.8 | 1JN6 3O41 3O45 |
| H3.18.9 | 3IFL 3IFN |
| H3.19.1 | 12E8 1FVD 1FVE 1I8K 1IGC 1KEN 1MCP 1N4X 1NCA 1NCB 1NCC 1NCD 1OHQ 1QOK 1RJL 1SJX 1TZI 1YY8 1YY9 2ADG 2ADI 2FJG 2FR4 2H9G 2JB5 2JB6 2MCP 3CFD 3CFE 3DVG 3DVN 3EO0 3EO1 3HI6 3L5W 3L5X 3L5Y 3L7F 3MBX 3NCY |
| H3.19.10 | 1FVD 1FVE |
| H3.19.11 | 3CFD 3CFE |
| H3.19.12 | 2JB5 2JB6 |
| H3.19.13 | 1I8K 1N4X 1YY8 1YY9 2H9G 3HI6 3L5W 3L5X 3L5Y 3L7F 3MBX 3NCY |
| H3.19.14 | INCA 1NCB 1NCC 1NCD 2ADG 2ADI 2FR4 3EO0 3EO1 |
| H3.19.15 | 1KEN |
| H3.19.16 | 1QOK |
| H3.19.17 | 12E8 |
| H3.19.18 | 1OHQ |
| H3.19.2 | 1AFV 1FVC 1I8M 1N8Z 1XF2 3BE1 3GK8 3HI5 3IY0 |
| H3.19.3 | 1EJO 1FRG 1HIL 1HIN 1IFH 1NQB 2H1P |
| H3.19.4 | 1D5B 1D5I 1D6V |
| H3.19.5 | 1EHL 1KEG 1SVZ |
| H3.19.6 | 1E6J 1E6O 2FL5 3NH7 |
| H3.19.7 | 1NL0 1P7K 2V17 |
| H3.19.8 | 1A6U 1A6V 1A6W 1ACY 1AD9 1AE6 1AI1 1FPT 1NC2 1OAQ 1PG7 1Q9Q 1Q9T 1Q9V 1YJD 2FJF 2GJJ 2R1W 2R1X 2R1Y 2R23 2R2B 2R2E 2R2H 3B2U 3B2V 3BPC |
| H3.19.9 | 1Q9K 1Q9L |
| H3.20.1 | 1DSF 1IGM 1MNU 1VGE 1ZV5 2FJH 2OSL 2R56 2R8S 3C08 3CVH 3G04 3GBN 3I9G 3NGB 8FAB |
| H3.20.10 | 3C08 |
| H3.20.11 | 1MNU |

TABLE 3-continued

| Segment | Position span PDB IDs |
|---|---|
| H3.20.12 | 3G04 |
| H3.20.13 | 2R8S |
| H3.20.14 | 3NGB |
| H3.20.15 | 1ZV5 |
| H3.20.16 | 3I9G |
| H3.20.17 | 2OSL |
| H3.20.18 | 1DSF |
| H3.20.19 | 2FJH |
| H3.20.2 | 1DEE 1DN0 1HEZ 1KFA 1OL0 1OSP 1SBS 3MA9 |
| H3.20.20 | 3MA9 |
| H3.20.21 | 1OL0 |
| H3.20.3 | 1AP2 1MVU 2AP2 |
| H3.20.4 | 1H0D 2G5B 3FMG |
| H3.20.5 | 3EO9 3EOA 3EOB |
| H3.20.6 | 1IQW 1IT9 1JFQ 1OTS 2A6D 2A6I 2EXW 2FEC 2FED 2FEE 2H2P 2HT2 2HT3 2HT4 2HTK 2HTL 3EJY 3EJZ 6FAB |
| H3.20.7 | 1J05 1MOE |
| H3.20.8 | 1IL1 3C09 |
| H3.20.9 | 2P45 2P4A |
| H3.21.1 | 1DVF 1FBI 1LMK 1XIW 2GSI 2IPT 2IPU 2NTF 2OP4 2R0W 2R0Z 3BKY 3EYS 3EYU 3IVK 3KDM 3KR3 3O2D |
| H3.21.10 | 2NTF 2OP4 |
| H3.21.11 | 3KDM 3O2D |
| H3.21.12 | 2GSI |
| H3.21.13 | 3BKY |
| H3.21.14 | 3IVK |
| H3.21.15 | 1DVF |
| H3.21.16 | 1FBI |
| H3.21.17 | 1LMK |
| H3.21.18 | 1XIW |
| H3.21.19 | 3KR3 |
| H3.21.2 | 1HYS 1IBG 1J5O 1N5Y 1N6Q 1R0A 1T03 |
| H3.21.3 | 1NMB 2GJZ 3FO1 3FO2 |
| H3.21.4 | 1QFU 3IFO 3IFP |
| H3.21.5 | 1EZV 2IBZ 3CX5 |
| H3.21.6 | 1W72 3G6A 3G6D |
| H3.21.7 | 1Q9O 3I02 |
| H3.21.8 | 1TZH 2XRA |
| H3.21.9 | 1BZ7 1R24 |
| H3.22.1 | 1DQD 1GIG 1OP3 1SEQ 1Y0L 1Y18 1ZAN 1ZLV 1ZLW 2A1W 2AI0 2AJ3 2J4W 2QHR 3CFJ 3CFK 3GO1 3OAU 3OAY 3OAZ 3OB0 |
| H3.22.10 | 1OP3 1ZLV 1ZLW 3OAU 3OAY 3OAZ 3OB0 |
| H3.22.11 | 1DQD |
| H3.22.12 | 1GIG |
| H3.22.13 | 1ZAN |
| H3.22.14 | 3GO1 |
| H3.22.15 | 2QHR |
| H3.22.16 | 2A1W |
| H3.22.17 | 2AI0 |
| H3.22.18 | 2J4W |
| H3.22.19 | 1SEQ |
| H3.22.2 | 1ADQ 1AQK 1DQL 1FNS 1KN2 1KN4 1KKQ 1YEE 1YEJ 1YEK 2AAB 2BSE 2QQN 3IY6 |
| H3.22.20 | 2AAB |
| H3.22.21 | 2QQN |
| H3.22.22 | 1AQK |
| H3.22.23 | 1DQL |
| H3.22.24 | 1ADQ |
| H3.22.25 | 1FNS |
| H3.22.26 | 3IY6 |
| H3.22.27 | 1KXQ |
| H3.22.28 | 2BSE |
| H3.22.3 | 1BJ1 1CZ8 2BRR |
| H3.22.4 | 1WC7 1WCB 2BMK |
| H3.22.5 | 1OM3 3LZF |
| H3.22.6 | 1UWX 3CMO |
| H3.22.7 | 3G6J 3IY7 |
| H3.22.8 | 3IYW 3N9G |
| H3.22.9 | 2DQU 3H42 |
| H3.23.1 | 1OP9 3HZK 3HZM 3HZV 3HZY 3IJH 3IJS 3IJY 3IKC 3LN9 |
| H3.23.10 | 1OP9 |
| H3.23.11 | 3LN9 |
| H3.23.2 | 3BAE 3BKC 3BKJ 3BKM |
| H3.23.3 | 2B0S 2B1A 2B1H |
| H3.23.4 | 1U6A 3HI1 |
| H3.23.5 | 3GI8 3GI9 |
| H3.23.6 | 2QQK 2QQL |
| H3.23.7 | 1FAI 2F19 |
| H3.23.8 | 3O0R |

TABLE 3-continued

| Segment | Position span | PDB IDs |
|---|---|---|
| H3.23.9 | | 1I3U |
| H3.24.1 | | 1U0Q 1ZVH |
| H3.24.2 | | 2HFG 2HRP |
| H3.24.3 | | 1QD0 |
| H3.24.4 | | 3LMJ |
| H3.24.5 | | 3LQA |
| H3.24.6 | | 1OPG |
| H3.24.7 | | 1RIH |
| H3.24.8 | | 3INU |
| H3.24.9 | | 1ETZ |
| H3.25.1 | | 1F58 2F58 |
| H3.25.2 | | 2FB4 2IG2 |
| H3.25.3 | | 1IKF |
| H3.25.4 | | 3PNW |
| H3.25.5 | | 3P30 |
| H3.25.6 | | 1DFB |
| H3.25.7 | | 1MVF |
| H3.25.8 | | 1RI8 |
| H3.26.1 | | 1HZH 1N0X 2NY7 |
| H3.26.2 | | 2FX7 |
| H3.26.3 | | 1ZVY |
| H3.26.4 | | 2XA3 |
| H3.26.5 | | 3GRW |
| H3.26.6 | | 2A9M |
| H3.27.1 | | 1F2X 1G6V |
| H3.27.2 | | 3IDX 3IDY |
| H3.27.3 | | 1G9M 1RZ8 1RZJ 1YYL 1YYM 2I5Y 2I60 2NXZ 2NY0 2NY1 2NY2 2NY3 2NY4 2NY5 2NY6 |
| H3.27.4 | | 1RJC |
| H3.27.5 | | 3BN9 |
| H3.28.1 | | 1Q1J 3C2A 3GHB |
| H3.28.2 | | 1ZA3 |
| H3.29.1 | | 3PIQ |

Generating the Antibody Conformation Representatives:

As discussed hereinabove, the library of Fv amino acid sequences results from a combinatorial combination of four weight fitted and reclosed segments derived from antibody's Fv source structures (denoted VL, L3, VH and H3 as segment groups). In the present example, the number of source structures was about 700, and considering four segments for each, the number of reconstructed structures would be 700^4, or about 10^11. If taken without reduction, the method would result in a prohibitively large library of reconstructed structures of antibodies. However, observations made in previous studies highlighted that each antibody backbone segment, other than H3, falls into a handful of canonical conformations, hence, the binding protein design procedure of the method presented herein starts by generating a reduced library of antibody backbones, or scaffolds, that samples the space of these canonical conformations plus a set of H3 backbone conformations. These observations lead the present inventors to consider reducing the number of recombined segments by sorting the segments by length, and sampling their conformation according to RMSD to thereby allow the selection of a reduced number of representative segments that would represent the conformational space adequately. Indeed, the sampling procedure reduced the number of segments into a manageable number, for which all permutations are used combinatorially to form reconstructed structures that constitute a reduced and representative library of amino-acid sequences having the common structural fold.

Once the conformation databases were generated, the next step was to create the conformation representatives; these are antibody structures that span the antibody conformation space. In a pre-computation step, the backbone segments, successfully inserted to the template antibody using the splice_out.xml protocol, were clustered by conformation.

Generating the Antibody Conformation Representatives:

A backbone representative was chosen from each cluster which was then combined with other backbone cluster representative segments to create the conformational representatives. The following "splice_in.xml" script was used to extract the dihedral angles from the database file of a specified antibody and inserts them to a scaffold antibody. The output antibody was then used as input for the next backbone segment insertion, and so on (e.g., first the H3 backbone segment was inserted, and then the output structure was used to insert an L3 backbone conformation and so on). This procedure can be repeated until all backbone conformation variants are generated.

The following script is used to insert an L1_L2 backbone conformation cluster representatives to the template antibody, necessary modifications for insertion of other segments are explained below.

splice_in.xml script:

```
<dock_design>
    <TASKOPERATIONS>
        <InitializeFromCommandline name=init/>
        <SeqprofConsensus name=seqprofcons
min_aa_probability=2 conservation_cutoff_aligned_segments=0
probability_larger_than_current=0 ignore_pose_profile_length_mismatch=1>
            <RestrictToAlignedSegments chain=1>
```

```
        <L1 source_pdb="%%template%%" start_res=24
stop_res=42/>
        <L2 source_pdb="%%template%%" start_res=52
stop_res=59/>
        <L3 source_pdb="%%template%%" start_res=93
stop_res=106/>
        <H1 source_pdb="%%template%%" start_res=134
stop_res=147/>
        <H2 source_pdb="%%template%%" start_res=157
stop_res=172/>
        <H3 source_pdb="%%template%%" start_res=209
stop_res=221/>
      </RestrictToAlignedSegments>
      </SeqprofConsensus>
    </TASKOPERATIONS>
    <SCOREFXNS>
      <sc12_w_correction weights=score12_w_corrections>
        <Reweight scoretype="res_type_constraint"
weight=0.3/>
      </sc12_w_correction>
    </SCOREFXNS>
    <FILTERS>
    </FILTERS>
    <MOVERS>
      <Splice name=splice torsion_database="L1_L2.db"
database_pdb_entry="%%source_pdb%%" scorefxn=sc12_w_correction ccd=0
template_file="%%template%%" design_task_operations=init,seqprofcons design=1
protein_family=antibodies segment="L1_ L2"/>
    </MOVERS>
    <PROTOCOLS>
      <Add mover=splice/>
    </PROTOCOLS>
</dock_design>
```

Command Line Options (can be Wrapped in a "Flag" File):

```
-ex1
-ex2aro
-use_input_sc
-extrachi_cutoff 5
-ignore_unrecognized_res
-chemical:exclude_patches    LowerDNA      UpperDNA      Cterm_amidation
SpecialRotamer    VirtualBB     ShoveBB     VirtualDNAPhosphate    VirtualNTerm
CTermConnect    sc_orbitals    pro_hydroxylated_case1    pro_hydroxylated_case2
ser_phosphorylated    thr_phosphorylated    tyr_phosphorylated    tyr_sulfated
lys_dimethylated    lys_monomethylated    lys_trimethylated    lys_acetylated
glu_carboxylated    cys_acetylated    tyr_diiodinated    N_acetylated    C_methylamidated
MethylatedProteinCterm
-restore_pre_talaris_2013_behavior
-pdb_comments true
-overwrite
-parser:script_vars source_pdb= <Source_pdb file name>
-parser:script_vars template=<template antibody PDB file>
-mute all
-pdb_comments true
-overwrite
-s <Input PDB file>
```

The Following Parameters can be Changed for Different Segments:

database_pdb_entry—Insert the name of the conformational representative, as it appears in the torsion database that should be inserted to the template antibody (The name is the last value of each entry in the torsion database file).

torsion_database—Change according to backbone conformation being sampled (e.g., if sampling an L1_L2 backbone segment then the torsion database should be "L1_L2.db").

Execution Example:

Rosetta_scripts.default.linuxgccrelease  -s  1x9q.pdb @flags -parser:script_vars source_pdb=1AHW.pdb -parser:script_vars template=1x9q.pdb It is noted that the output PDB file from this exemplary execution will be the 1X9Q antibody structure with backbone conformation of L1_L2 from 1AHW inserted to it. This structure should then be used as the input structure for the next segment insertion. The order in which the segments are inserted is inconsequential.

For this example, a backbone representative was chosen from each cluster which was then combined with other backbone cluster representative segments to create the conformational representatives.

Table 4 presents the segments extracted from the source antibody structures, subjected to the segment reduction procedure, and subsequently used in the construction of a reduced library of about 4,500 structural scaffold representatives.

TABLE 4

Representative weight fitted and reclosed segment by structural cluster

| VL | L3 | VH | H3 |
|---|---|---|---|
| PDB IDs: | PDB IDs: | PDB IDs: | PDB IDs: |
| 1M7I 1OP3 | 1EMT 1Q9Q | 12E8 1AHW | 1A7R 1BQL 1D5B |
| 1Q9T 3LS5 | | 1DQJ 1FGN | 1DZB 1E4X 1FRG |
| 3O45 | | 1I8K 1KCU | 1H0D 1HEZ 1J5O 1LO4 |
| | | 1KEG 1Q9V | 1N8Z 1QFU 1RIU 1RUK |
| | | 3FO0 | 1RUQ 1UCB 1UWE |
| | | | 1UZ8 1VGE 1WCB |
| | | | 1XGU 2AP2 2B1A |
| | | | 2BRR 2DBL 2DDQ |
| | | | 2FJG 2NLJ 2NXZ 2R1W |
| | | | 2UZI 2V17 2VDQ |
| | | | 2W9D 3BKJ 3D85 3EO0 |
| | | | 3EYS 3FO2 3G6A |
| | | | 3GHB 3HAE 3HNV |
| | | | 3IJH 3JWO 3L5W 3L95 |
| | | | 3NFS 3NH7 3O41 |

As can be seen in Table 4, in this exemplary case, the segments presented in Table 3, which have undergone the weight fitting for segment closure procedure, were reduced to 5 ($V_L$)×2 (L3)×9 ($V_H$)×50 (H3). Combining these representative segments into all permutations afforded a reduced library of about 4,500 structural representatives. All sequence and conformation information from the template antibody was eliminated in this procedure, except for the relative orientation of the disulfide-bonded cysteines in the variable light and variable heavy domains and the PSSM-derived sequence constraints are used to guide sequence-design choices.

According to some embodiments of the present invention, the library of amino-acid sequences having a common structural fold comprises torsion databases, wherein each torsion database contains "n" entries, n being the number of successfully weight fitted and reclosed segments in the context of the template antibody. In some embodiments, each entry in the torsion database has 4(N+1) fields, N being the sequence length of the inserted backbone segments. In some embodiments, the fields are the $\Psi$, $\Phi$, and $\Omega$, dihedral angle values for each of the residues of the inserted backbone segment and the residue identity. In some embodiments, the last four fields are the start, end and split site residue numbers of the grafted segment relative to the template antibody and other identifying tags, such as the file name of the source antibody.

During the execution of the methods presented herein, whenever a different backbone conformation was sampled, the PSSM for the entire antibody was reassigned according to the current segments, synchronizing the sequence constraints with the backbone conformation. For efficiency, at different phases of the method, different sets of residues were subjected to design. For instance, several initial design phases only optimize the ligand-binding surface, whereas at the end of the design protocol there were several iterations of full sequence optimization of all antibody positions (subject to sequence constraints). Sequence constraints, such as PSSM, considerably reduce the combinatorial design problem; in a representative case, the latter step of full design over a 230 amino acid long variable fragment has a total of about $10^{\wedge}117$ different possible sequence combinations, equivalent to full redesign of only 93 positions; increasing the PSSM cutoffs would further reduce this combinatorial space.

As an exemplary demonstration of the role played by correlations between positions in the CDRs and the framework, the backbone-conformation cluster L1.16_L2.8 (see, Table 3) has a fully conserved phenylalanine at framework position L71, which interacts with either a leucine or an isoleucine at position L30 on CDR1. Backbone-conformation cluster L1.10_L2.8 uses different conserved residues in the framework to stabilize CDR L1—either valine or isoleucine at L30 and a fully conserved tyrosine at position 71. These conserved sequence-conformation correlations were previously identified as key to maintaining CDR L1 stability by using sequence constraints that are correlated to the segment conformation the design process accounts for these relations.

Sampling of Heavy and Light Chain Rigid Body Orientation:

The third determinant of the Fv structure, besides the backbone conformation and sequence, is the Rigid Body Orientation (RBO) between the light and the heavy chain. Acknowledging the need to sample the RBOs, RBOut was written so as to construct a database of RBOs based on experimental κ-light chain antibody structures. In the database the RBO of each antibody is represented as transformation matrix between the second cysteine in each Ig-domain (approximately the centers of mass). Specifically the RBOut database is constructed by running the following across all antibodies which RBO should go to the database:

```
rosetta_scripts.default.linuxgccrelease  -s  pdbs/input.pdb  -parser:protocol
rb_db.xml    -parser:script_vars    templatePdb=2BRR.pdb    -parser:script _vars
dbName=database/RBOut.db @flags
  rb_db.xml
    <dock_design>
      <SCOREFXNS>
        <sc12_w_correction weights=score12_w_corrections/>
      </SCOREFXNS>
      <FILTERS>
      </FILTERS>
      <MOVERS>
        <RBOut name=rbout template_fname=" %%templatePdb%%"
jump_dbase_fname="%%dbName%%"/>
      </MOVERS>
        <PROTOCOLS>
          <Add mover_name=rbout/>
        </PROTOCOLS>
    </dock_design>
``` flags
-database/home/labs/fleishman/norn/Rosetta/main/database
-ex1
-ex2aro
-use_input_sc
-corrections::correct
-corrections::score:no_his_his_pairE
-extrachi_cutoff 12
-ignore_unrecognized_res
-chemical:exclude_patches LowerDNA UpperDNA Cterm_amidation SpecialRotamer VirtualBB ShoveBB VirtualDNAPhosphate VirtualNTerm CTermConnect sc_orbitals pro_hydroxylated_case1 pro_hydroxylated_case2 ser_phosphorylated thr_phosphorylated tyr_phosphorylated tyr_sulfated lys_dimethylated lys_monomethylated lys_trimethylated lys_acetylated glu_carboxylated cys_acetylated tyr_diiodinated N_acetylated C_methylamidated MethylatedProteinCterm
-overwrite
-nstruct 1
-restore_pre_talaris_2013_behavior
-score:patch score12_w_corrections.wts
-score:weights pre_talaris_2013_standard Additionally, an algorithm "RBIn" is implemented to allow sampling of RBOs from the RBO database during the antibody design protocol. The use of RBIn is shown in the design_refine.xml below.

Instead of using of the RBO from 1X9Q, the rigid body orientation of an anti-meningococcal antibody (PDB ID:2BRR) was implemented, which for light chain aligned antibodies, had the most average placement of the backbone and c-beta atoms for the second cysteine in the heavy chain, compared to other antibodies.

Similar to the covariance between sequence and CDR conformation, one might be able to guide sampling of RBOs according to the identity of the interface residues. This could be done by neural network methods as described elsewhere [Abhinandan, K. R. et al., *Protein Engineering, Design & Selection*, 2010, 23(9), pp. 689-697]. In such a method the probability of sampling RBOs in the database could be proportional to the estimated RBO likelihood.

A Method for Seeding the Docking and Refinement Algorithm:

A maximally diverse chimera library of 6000 members was constructed by combining the canonical conformations on $V_L$ (5), L3 (3), $V_H$ (8) with 50 diverse H3 conformations (see above, Generating conformational representatives). These seeds are subsequently refined with the optimize_chimera.xml script to improve packing, segment compatibility with each other and overall improve the protein's stability.

rosetta_scripts.default.linuxgccrelease -s chimera_seed.pdb -parser:protocol optimize_chimera.xml -out:file:fullatom @flags -parser:script_vars prefix=chimera_seed.c
    flags
    -database/home/labs/fleishman/norn/Rosetta/main/database/
    -ex1
    -ex2aro
    -use_input_sc
    #-corrections::correct
    #-corrections:: score:no_his_his_pairE
    -extrachi_cutoff 8
    -ignore_unrecognized_res
    -chemical:exclude_patches LowerDNA UpperDNA Cterm_amidation SpecialRotamer VirtualBB ShoveBB VirtualDNAPhosphate VirtualNTerm CTermConnect sc_orbitals pro_hydroxylated_case1 pro_hydroxylated_case2 ser_phosphorylated thr_phosphorylated tyr_phosphorylated tyr_sulfated lys_dimethylated lys_monomethylated lys_trimethylated lys_acetylated glu_carboxylated cys_acetylated tyr_diiodinated N_acetylated C_methylamidated MethylatedProteinCterm
    -nstruct 1
    -parser:script_vars
configdir=/home/labs/fleishman/norn/config_dirs/2BRR_config_dir
source_pdb=/home/labs/fleishman/norn/config_dirs/2BRR_config_dir/2BRR.pdb
    -mute all
    @/home/labs/fleishman/norn/config_dirs/2BRR_config_dir/flags_PSSM
    -pdb_comments true
    -docking:no_filters
    -linmem_ig 10
    -renumber_pdb
    -per_chain_renumbering
    optimize_chimera.xml:

```
<dock_design>
  <SCOREFXNS>
    <TalarisCal_coordcst weights=talaris2013_calibrated>
      <Reweight scoretype=coordinate_constraint weight=0.06/>
    </TalarisCal_coordcst>
    <TalarisCal_res_type_cst weights=talaris2013_calibrated>
      <Reweight scoretype="res_type_constraint" weight=0.2/>
    </TalarisCal_res_type_cst>
        <soft_rep_res_type_cst weights=soft_rep>
            <Reweight          scoretype="res_type_constraint" weight=0.2/>
            </soft_rep_res_type_cst>
        <soft_rep_coordcst weights=soft_rep>
            <Reweight          scoretype=coordinate_constraint weight=0.06/>
            </soft_rep_coordcst>
    </SCOREFXNS>
        <TASKOPERATIONS>
            <SeqprofConsensus              name=seqprofcons min_aa_probability=2    conservation_cutoff_protein_interface_design=0 conservation_cutoff_aligned_segments=1    probability_larger_than_current=0 ignore_pose_profile_length_mismatch=1>
```

```
            <ProteinInterfaceDesign
design_chain1=1 design_chain2=0/> 8A cutoff around the ligand defines the binding
surface
            <RestrictToAlignedSegments chain=1>
                <L1
source_pdb="%%source_pdb%%" start_res=24 stop_res=40/>
                <L2
source_pdb="%%source_pdb%%" start_res=47 stop_res=56/>
                <L3
source_pdb="%%source_pdb%%" start_res=90 stop_res=101/>
                <H1
source_pdb="%%source_pdb%%" start_res=130 stop_res=142/>
                <H2
source_pdb="%%source_pdb%%" start_res=149 stop_res=164/>
                <H3
source_pdb="%%source_pdb%%" start_res=202 stop_res=220/>
            </RestrictToAlignedSegments>
        </SeqprofConsensus>
        <RestrictToAlignedSegments name=CDRs chain=1>
            <L1        source_pdb="%%source_pdb%%"
start_res=24 stop_res=40/> Norn: This could be shortened by 3 res at C-term
            <L2        source_pdb="%%source_pdb%%"
start_res=47 stop_res=56/> Norn: This could be shortened by 3 res N-term?
            <L3        source_pdb="%%source_pdb%%"
start_res=90 stop_res=101/>
            <H1        source_pdb="%%source_pdb%%"
start_res=130 stop_res=142/> Norn: Why is this loop sticking so deep? Many of these
res would never contact Ag.
            <H2        source_pdb="%%source_pdb%%"
start_res=149 stop_res=164/>
            <H3        source_pdb="%%source_pdb%%"
start_res=202 stop_res=220/>
        </RestrictToAlignedSegments>
        <RestrictToAlignedSegments      name=designable_Ab
chain=1/> this task operation defines the entire inter-cysteine region + CDR3. This is
necessary for splice in to design these segments
        <InitializeFromCommandline name=init/>
        <DesignInterfaces   name=interfaces   design_shell=10
repack_shell=12/>
        <RestrictToRepacking name=rtr/>
        <RestrictAbsentCanonicalAAS        name=no_cys
keep_aas="ADEFGHIKLMNPQRSTVWY"/>
    </TASKOPERATIONS>
    <FILTERS>
        <ScoreType name=total_score score_type=total_score
scorefxn=TalarisCal_res_type_cst confidence=0 threshold=100/>
        Sigmoid   name=sigmoid_stability   filter=total_score
offset=2                                     steepness=0.3
baseline_checkpoint="checkpoint_files/%%prefix%%.stability.checkpoint"/>   let
stability increase over a longer range than binding energy, but also let stability
deteriorate if necessary (offset)
    </FILTERS>
    <MOVERS>
        <PackRotamersMover       name=design_score12
scorefxn=TalarisCal_res_type_cst task_operations=CDRs,seqprofcons,init,no_cys/>
        <ClearConstraintsMover name=clear_constraints/>
            <RBI                      name=rb_transform
rigid_body_dbase="%%configdir%%/rb.database.2BRR" from_entry=1 to_entry=750
randomize=true/>
            <Splice                            name=H3
profile_weight_away_from_interface=1.5   scorefxn=TalarisCal_res_type_cst
torsion_database="%%configdir%%/torsion_db/H3.db"   dbase_iterate=0
rb_sensitive=1 ccd=0 res_move=5 randomize_cut=0 delta_lengths=0 equal_length=0
design=1                          template_file="%%source_pdb%%"
design_task_operations=designable_Ab,seqprofcons,init,no_cys>
            <Segments current_segment=H3>
            <L1_L2
pdb_profile_match="%%L1_L2.pdb_profile_match_jun13%%"
profiles="%%L1_L2.profiles%%"/>
            <L3
pdb_profile_match="%%L3.pdb_profile_match_jun13%%"
profiles="%%L1_L2.profiles%%"/>
            <H1_H2
pdb_profile_match="%%H1_H2.pdb_profile_match_jun13%%"
profiles="%%H1_H2.profiles%%"/>
            <H3
pdb_profile_match="%%H3.pdb_profile_match_jun13%%"
profiles="%%H1_H2.profiles%%"/>
        </Segments>
```

```
      </Splice>
      <Splice                              name=H1_H2
profile_weight_away_from_interface=1.5   scorefxn=TalarisCal_res_type_cst
torsion_database="%%configdir%%/torsion_db/H1_H2.db"    dbase_iterate=0
rb_sensitive=1 ccd=0 res_move=5 randomize_cut=0 delta_lengths=0 equal_length=0
design=1                              template_file="%%source_pdb%%"
design_task_operations=designable_Ab,seqprofcons,init,no_cys>
          <Segments current_segment=H1_H2>
              <L1_L2
pdb_profile_match="%%L1_L2.pdb_profile_match_jun13%%"
profiles="%%L1_L2.profiles%%"/>
              <L3
pdb_profile_match="%%L3.pdb_profile_match_jun13%%"
profiles="%%L1_L2.profiles%%"/>
              <H1_H2
pdb_profile_match="%%H1_H2.pdb_profile_match_jun13%%"
profiles="%%H1_H2.profiles%%"/>
              <H3
pdb_profile_match="%%H3.pdb_profile_match_jun13%%"
profiles="%%H1_H2.profiles%%"/>
          </Segments>
      </Splice>
      <Splice                              name=L3
profile_weight_away_from_interface=1.5   scorefxn=TalarisCal_res_type_cst
torsion_database="%%configdir%%/torsion_db/L3.db"    dbase_iterate=0
rb_sensitive=1 ccd=0 res_move=5 randomize_cut=0 delta_lengths=0 equal_length=0
design=1                              template_file="%%source_pdb%%"
design_task_operations=designable_Ab,seqprofcons,init,no_cys>
          <Segments current_segment=L3>
              <L1_L2
pdb_profile_match="%%L1_L2.pdb_profile_match_jun13%%"
profiles="%%L1_L2.profiles%%"/>
              <L3
pdb_profile_match="%%L3.pdb_profile_match_jun13%%"
profiles="%%L1_L2.profiles%%"/>
              <H1_H2
pdb_profile_match="%%H1_H2.pdb_profile_match_jun13%%"
profiles="%%H1_H2.profiles%%"/>
              <H3
pdb_profile_match="%%H3.pdb_profile_match_jun13%%"
profiles="%%H1_H2.profiles%%"/>
          </Segments>
      </Splice>
      <Splice                              name=L1_L2
profile_weight_away_from_interface=1.5   scorefxn=TalarisCal_res_type_cst
torsion_database="%%configdir%%/torsion_db/L1_L2.db"    dbase_iterate=0
rb_sensitive=1 ccd=0 res_move=5 randomize_cut=0 delta_lengths=0 equal_length=0
design=1                              template_file="%%source_pdb%%"
design_task_operations=designable_Ab,seqprofcons,init,no_cys>
          <Segments current_segment=L1_L2>
              <L1_L2
pdb_profile_match="%%L1_L2.pdb_profile_match_jun13%%"
profiles="%%L1_ L2.profiles%%"/>
              <L3
pdb_profile_match="%%L3.pdb_profile_match_jun13%%"
profiles="%%L1_L2.profiles%%"/>
              <H1_H2
pdb_profile_match="%%H1_H2.pdb_profile_match_jun13%%"
profiles="%%H1_H2.profiles%%"/>
              <H3
pdb_profile_match="%%H3.pdb_profile_match_jun13%%"
profiles="%%H1_H2.profiles%%"/>
          </Segments>
      </Splice>
      <Splice                     name=splice_seqconstraints
scorefxn=TalarisCal_res_type_cst add_sequence_constraints_only=1>
          <Segments current_segment=L1_L2>
              <L1_L2
pdb_profile_match="%%L1_L2.pdb_profile_match_jun13%%"
profiles="%%L1_L2.profiles%%"/>
              <L3
pdb_profile_match="%%L3.pdb_profile_match_jun13%%"
profiles="%%L1_L2.profiles%%"/>
              <H1_H2
pdb_profile_match="%%H1_H2.pdb_profile_match_jun13%%"
profiles="%%H1_H2.profiles%%"/>
              <H3
pdb_profile_match="%%H3.pdb_profile_match_jun13%%"
profiles="%%H1_H2.profiles%%"/>
```

```
            </Segments>
          </Splice>
          <TaskAwareCsts name=Ab_constraints/>
          <PackRotamersMover          name=design_softrep
scorefxn=soft_rep_res_type_cst task_operations=CDRs,seqprofcons,init,no_cys/>
            <MinMover                                       name=soft_min
scorefxn=soft_rep_coordcst bb=0 jump=1 chi=1/>
            <MinMover                                       name=hard_min
scorefxn=TalarisCal_coordcst bb=0 jump=1 chi=1/>
            <RotamerTrialsMinMover                          name=rtmin
task_operations=rtr,CDRs,init scorefxn=TalarisCal_res_type_cst/>
            <AtomTree name=simple_ft simple_ft=1/>
            <AtomTree                name=two_parts_chain1
two_parts_chain1=1/>
            <AtomTree name=docking_ft_docking_ft=1/>
            <ParsedProtocol name=post_splice_refine>
               <Add   mover=simple_ft/>   docking_ft gets
confused on a loop-containing ft
               <Add mover=two_parts_chain1/>
               <Add mover=Ab_constraints/>
               <Add mover=design_softrep/>
               <Add mover=soft_min/>
               <Add mover=design_softrep/>
               <Add mover=hard_min/>
               <Add mover=design_score12/>
               <Add mover=hard_min/>
               <Add mover=rtmin/>
               <Add   mover=simple_ft/>  get  back  to  an  ft  for
randomize splices
            </ParsedProtocol>
            <ParsedProtocol name=splice_refine_L1_L2>
              <Add mover=L1_L2/>
              <Add mover=post_splice_refine/>
            </ParsedProtocol>
            <ParsedProtocol name=splice_refine_L3>
              <Add mover=L3/>
              <Add mover=post_splice_refine/>
            </ParsedProtocol>
            <ParsedProtocol name=splice_refine_H1_H2>
              <Add mover=H1H2/>
              <Add mover=post_splice_refine/>
            </ParsedProtocol>
            <ParsedProtocol name=splice_refine_H3>
              <Add mover=H3/>
              <Add mover=post_splice_refine/>
            </ParsedProtocol>
            <PackRotamersMover               name=design_softrep_rb
scorefxn=soft_rep_res_type_cst task_operations=init,no_cys,seqprofcons,interfaces/>
            <PackRotamersMover                name=design_score12_ rb
scorefxn=TalarisCal_res_type_cst
task_operations=init,no_cys,seqprofcons,interfaces/>
            <RotamerTrialsMinMove                            name=rtmin_rb
task_operations=rtr,init,interfaces scorefxn=TalarisCal_res_type_cst/>
            <ParsedProtocol name=RBMove>
               <Add mover=clear_constraints/>
               <Add mover=rb_transform/>
               <Add mover=splice_seqconstraints/>
               <Add mover=two_parts chain1/>
               <Add mover=Ab_constraints/>
               <Add mover=design_softrep_rb/>
              <Add mover=soft_min/>
              <Add mover=design_softrep_ rb/>
              <Add mover=hard_min/>
              <Add mover=design_score12_rb/>
              <Add mover=hard_min/>
              <Add mover=rtmin_rb/>
                <Add mover=simple_ft/>
            </ParsedProtocol>
            <ParsedProtocol          name=splice_rbmin_menu
mode=single_random>
                <Add            mover=splice_refine_H3
apply_probability=0.15/>
                <Add            mover=splice_refine_L3
apply_probability=0.15/>
                <Add         mover=splice_refine_L1_L2
apply_probability=0.15/>
                <Add         mover=splice_refine_H1_H2
apply_probability=0.15/>
                <Add                  mover=RBMove
```

-continued

```
apply_probability=0.40/>
        </ParsedProtocol>
            <GenericMonteCarlo    name=mc_splice_rb
mover_name=splice_rbmin_menu filter_name=total_score trials=50 preapply=0
temperature=0                                      drift=1
saved_accept_file_name="checkpoint_files/%%prefix%%.checkpoint.pdb"
saved_trial_number_file="checkpoint_files/%%prefix%%.mc1.checkpoint"
mover_tag="mc_splice_rb"/>
    </MOVERS>
    <PROTOCOLS>
        <Add mover=mc_splice_rb/>
    </PROTOCOLS>
</dock_design>
```

The PatchDock algorithm [Schneidman-Duhovny D. et al., *Nucl. Acids. Res.*, 2005, 33, W363-367] was used to generate approximately 5000 candidate antigen-antibody complexes for each member of the chimera library. To run the Patchdock algorithm, molecular surface files were constructed using "perl buildMS.pl $target", followed by the construction of the parameter file "buildParams.pl binders/$binder target/$targetname" before finally running Patchdock by "submit_patchdock.sh params.txt out/$binder.pd".

Alternative Sampling Methodology:

A strategy for sampling and refinement of backbone conformations was based on coordinate descent, wherein each of the segments in turn were sampled and optimized 50 times from the database of experimental backbone conformations before the best were chosen. To provide an alternative sampling of the conformational diversity, the coordinate descent in the sampling and refinement of backbone conformations protocol was replaced with Monte Carlo Simulated Annealing (MCSA). Five different moves were made available for the MCSA sampler: $V_L$, L3, $V_H$, H3, and RBO. Each move encompassed different conformational diversity and had varying probability of being accepted. Accounting for this, the random selection of moves was biased so that H3 was most likely to be sampled, while other moves were sampled less often. Specifically, H3, L3, $V_L$, $V_H$, and RBO were sampled with a probability of 0.40, 0.05, 0.15, 0.25, and 0.15, as shown in the design_and_refine.xml protocol presented below.

Algorithm Optimization:

To optimize the AbDesign algorithm, it has been suggested that the efficiency could be improved by preempting time spend on ill-fated trajectories. Consequently, various structural statistics were assessed for predictiveness of final pose quality. It was found that buried surface area and binding energy at various stages before loop splice is initialized, were predictive for final pose quality. See, soft_dock_sasa_filter, 2nd_hard_min_sasa_filter and ddg_final_commitment filter in the xml protocol below. During loop splicing it was found that backbone clashes are predictive for whether a loop will be successfully inserted.

AbDesign Algorithm:

The design and refine algorithm, which takes the optimized chimera, Patchdock file, and antigen as input can be executed as follows:

```
rosetta_scripts.default.linuxgccrelease -s in_pdbs/optimized_chimera.pdb -parser:script_vars prefix=checkpoint/optimized_chimera.pdb.gz.c             -parser:script_vars
patchdock=in_patchdock_T/optimized_chimera.pd - out:
file:silent out/designed_antibody.out @flags
    flags:
    -database  /home/labs/fleishman/norn/Rosetta/main/database/
    -use_occurrence_data
    -ex1
    -ex2aro
    -use_input_sc
    -extrachi_cutoff 8
    -ignore_unrecognized_res
    -chemical:exclude_patches LowerDNA UpperDNA Cterm_amidation SpecialRotamer VirtualBB ShoveBB VirtualDNAPhosphate    VirtualNTerm    CTermConnect
        sc_orbitals pro_hydroxylated_case1 pro_hydroxylated_case2 ser_phosphorylated thr_phosphorylated tyr_phosphorylated tyr_sulfated lys_dimethylated lys_monomethylated lys_trimethylated lys_acetylated glu_carboxylated cys_acetylated tyr_diiodinated N_acetylated C_methylamidated MethylatedProteinCterm
    -parser:protocol protocol/design_refine.xml
    -nstruct 200
    -out:file:silent_struct_type binary
    -mute protocols.toolbox.task_operations.SeqprofConsensusOperation
    -mute all
    -parser:script_vars           configdir=2BRR_config_dir
        source_pdb=2BRR_config_dir/2BRR.pdb
    @ 2BRR_config_dir/flags_PSSM
    -pdb_comments true
    -docking:no_filters
    -linmem_ig 10
    -renumber_pdb
```

Abdesign.xml:

Generating Designed Antibodies:

The method used the structure representative generated as described hereinabove, as the input structures. For generating the benchmark designs, each of the representative antibody conformations were aligned to the natural antibody in the complex structure and then added the target protein coordinates to the representative antibody conformation. The original binding mode was then perturbed using reduced representation docking. The final designs did not all have the same binding mode as the natural antibody against the same target protein. Additional filtering was performed using a python script to obtain structure that bound within a 4 Å cutoff of the natural antibody binding mode.

As described hereinabove in the context of some embodiments of the present invention, the members of the library of reconstructed antibodies generated in the previous steps were docked to the molecular surface of interest of a molecular entity, using a low-resolution rigid body surface complementarity (orientation) refinement procedure, collectively referred to herein a rough matching procedure. Once docked, the reconstructed antibodies underwent amino acid sequence optimization for the residues of the binding site, which were modified subject to the PSSM constraints. The rough matching procedure then optimized the side-chain residues on the reconstructed antibody, and assessed the complex according to free energy and structure stability filters. Thereafter, the resulting complexes were ranked according to docking and stability scores and clustered by RMSD, thereby this step afforded a reduced set of representative complexes, numbering a few hundreds of thousands to a few million complexes, depending on the available computing power and other practical considerations.

For complexes that passed the structural filters of the previous step, a procedure was used to randomly select a complex out of the ranked and sorted complexes, using a Monte-Carlo selection routine. It is noted that other selection criteria and random drawing routines are contemplated under some embodiments of the present invention.

As discussed hereinabove in the context of some embodiments of the present invention, the selected complex was subjected to a finer resolution docking process which is accompanied with a PSSM-based stochastic sequence optimization (PSSM-SSO) of amino acid residues at the antigen-scaffold interface region, collectively referred to herein as a conducive matching procedure. Complexes that achieved a predetermined cutoff value of the matching scores, e.g., for a minimal buried surface area upon binding (typically pre-determined at 1000 Å² in the case of antibodies), were passed to the next conducive matching procedure, while complexes that did not achieve these cutoff were discarded.

The next conducive matching procedure implemented a fast backbone-sampling strategy that is guided by the pre-computed backbone-conformation database (Box 9 in FIGS. 1 and 2). Briefly, one of the weight fitted and reclosed segments was selected randomly for substitution with another weight fitted and reclosed segment of the same cluster, allowing the segment selection to vary in length by 0-4 amino acid residues, according to some embodiments of the present invention (Box 18 in FIG. 2).

In the present exemplary demonstration of the method presented herein, the procedure randomly sampled 50 different weight fitted and reclosed segments from the relevant conformation database that were within a predefined sequence-length change with respect to the input segment. For example, if the representative weight fitted and reclosed segment undergoing design had an H3 of length x amino acids, refinement samples H3 backbone segments of length x±4. The allowed length change depends on the segment currently being designed. Restricting segment-length sampling reduces the bias for longer segments, which were likely to have more favorable stability and binding energies. For example, in the benchmarked recapitulation test presented hereinbelow, the allowed length change parameter was set to ±2 for segment types $V_L$, $V_H$ and L3, and ±4 for H3.

Changing the current weight fitted and reclosed segment to any other weight fitted and reclosed segment in the torsion database consists of imposing the backbone dihedral angles specified in the database and was done in well under a second on a standard CPU. For each sampled backbone the method uses combinatorial side-chain packing to design the sequence subject to the PSSM constraints above. The procedure then simultaneously optimized the complex binding interface by high-resolution rigid body orientation refinement, and side-chain conformation and amino acid identity optimization in the target binding surface and in a 3-10 Å radius around the replaced segment using PSSM-SSO. The conducive matching procedure was repeated three times, starting with a soft-repulsive potential and ending with the standard all-atom energy function. The procedure then used the rotamer trials-minimization protocol, whereby single side-chains are selected at random, packed, and minimized. This iterative procedure resulted in improvements to side-chain packing in the antibody core and in the antibody-target interface.

Hence, as described hereinabove, the design protocol was divided into two parts: a rough matching procedure (Box 14 in FIG. 3), and a conducive marching procedure aimed at optimizing the binding energy between the antibody and target protein (Boxes 16a and 16b in FIG. 2); and a computationally intensive refinement step which entails backbone sampling of all four antibody segments (Box 18 in FIG. 2). The first part was parsed under a sub protocol in the design xml named "start_fresh".

The second part is parsed under the sub-protocol "recover" which performed backbone sampling on each of the four segments using coordinate-descent and subject to an optimization function constrained by binding and stability scores.

Command Line Options (can be Wrapped in a "Flag" File)
 -linmem_ig 10
 -ex1
 -ex2aro
 -use_input_sc
 -extrachi_cutoff 8
 -ignore_unrecognized_res
 -chemical:exclude_patches LowerDNA UpperDNA Cter-
    m_amidation SpecialRotamer VirtualBB ShoveBB Virtual DNAPhosphate VirtualNTerm CTermConnect sc_orbitals pro_hydroxylated_case1 pro_hydroxylated_case2 ser_phosphorylated thr_phosphorylated tyr_phosphorylated tyr_sulfated lys_dimethylated lys_monomethylated lys_trimethylated lys_acetylated glu_carboxylated cys_acetylated tyr_diiodinated N_acetylated C_methylamidated MethylatedProteinCterm
 -parser:protocol AbDesign.xml
 -nstruct 10
 -mute all
 -pdb_comments true
 -parser:script_vars lig=<ligand PDB file>

Execution Example rosetta_scripts.default.linuxgccrelease @flags -parser:script_vars prefix=vL_3LS5_vH_6FAB_L3_30AY_H3_3FZU.pdb.gz_-s vL_3LS5_vH_6FAB_L3_3OAY_H3_3FZU.pdb.gz A key challenge in protein design of function is that the protein needs to be both stable in its designed conformation and bind its target molecule. In the present exemplary case of antibodies, for each of the four backbone segments ($V_L$, L3, $V_H$ and H3), the procedure randomly sampled 50 backbone conformations derived from that segment's conformation database (Box 18 in FIG. 2), computed the binding energy (EB) and stability (ES) of the redesigned antibody, and transformed each according to the following sigmoid function:

$$f(E) = \frac{1}{1 + e^{(E-o)s}} \quad \text{(Equation 1)}$$

wherein E is either the binding energy (EB) or the energy of the unbound antibody (ES), o is the sigmoid midpoint, where f(E) assumes a value of ½ and s is the steepness of the sigmoid around the midpoint. The sigmoid approaches values of one at very low energies and zero at very high values. Before sampling conformations for each of the segments, parameter o in Eq. 1 was reset to the energy value of the currently designed antibody, so both sigmoids were close to their midpoints at the start of refinement of each segment. The optimization objective function was the product of the two sigmoids: o=f(ES)×f(EB), resulting in values approaching one when both ES and EB are low and values approaching zero if either one of the energy criteria is high. The effect of optimizing this objective function was to find a backbone conformation that is both sufficiently stable and high affinity.

For example, a backbone conformation that improves binding energy by 10 Rosetta energy units (R.e.u.) (transformed sigmoid value of 0.99) and stability by 10 R.e.u. (transformed value of 0.97, the product (ES×EB) equals 0.963, would be preferred to a backbone conformation that improves the binding energy by 1 R.e.u (transformed value of 0.61) and the stability by 30 R.e.u (transformed value 0.999, product equals 0.6), as shown in FIG. 4.

Figure 4:
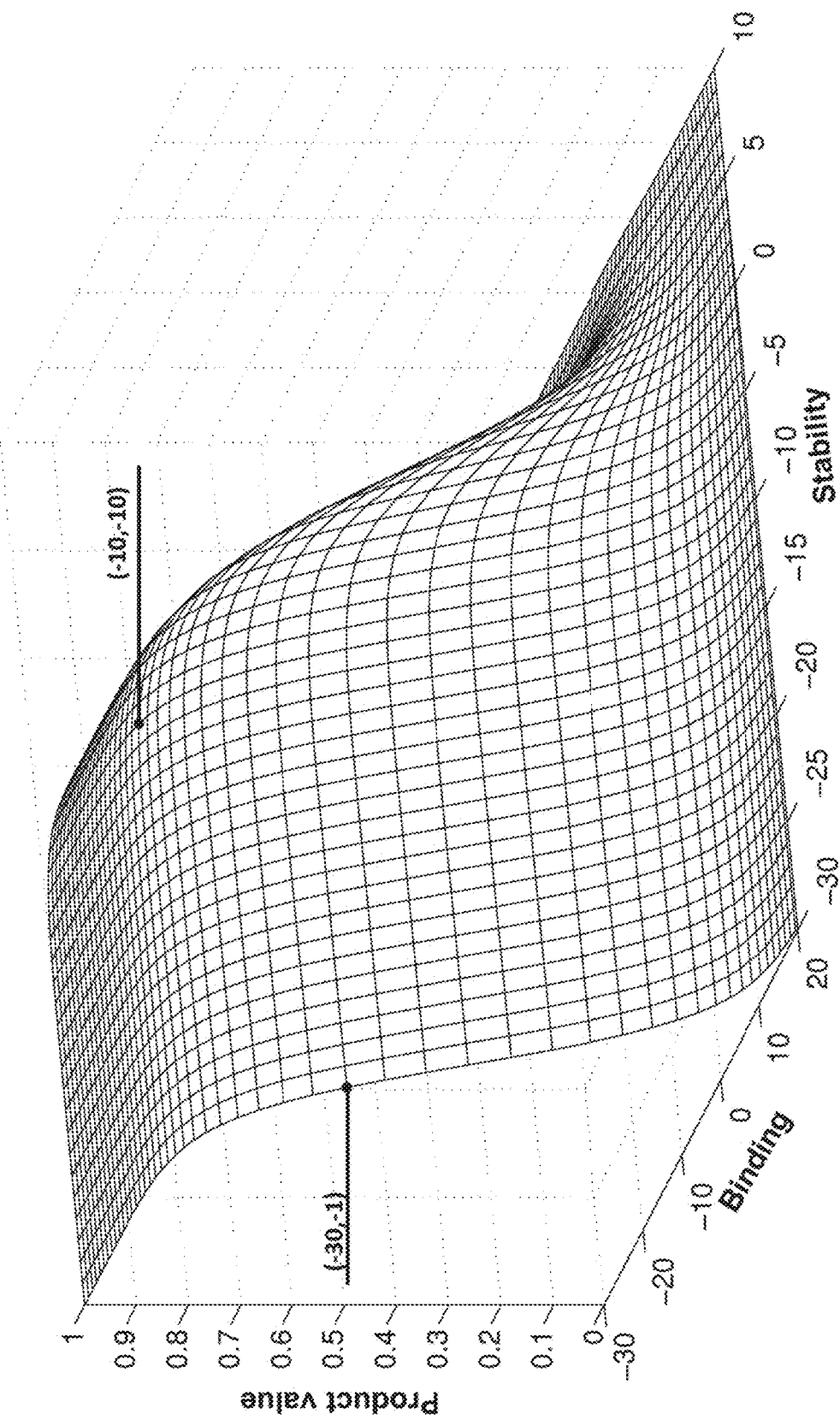
FIG. 4 presents a 3D plot of the of the objective function, the product value of the stability and the binding sigmoids as defined by Eq. 1, wherein the backbone conformations sampled during design are evaluated by an objective function that is constrained by both antibody stability and binding affinity.

FIG. 4 presents a 3D plot of the of the objective function, the product value of the stability and the binding sigmoids as defined by Eq. 1, wherein the backbone conformations sampled during design are evaluated by an objective function that is constrained by both antibody stability and binding affinity.

As can be seen in FIG. 4, a transformed value of a −10 R.e.u change in binding and stability is preferred to a −30 R.e.u change in stability and a −1 R.e.u change in binding. The product of the two transformations gauges the effect the incorporated segment has on the antibody's stability and binding affinity to the target relative to the baseline score (the interim best scoring antibody structure so far).

An example of the change in binding energy and stability before and after the segment optimization is shown in FIGS. 5 A-B.

Figure 5B:
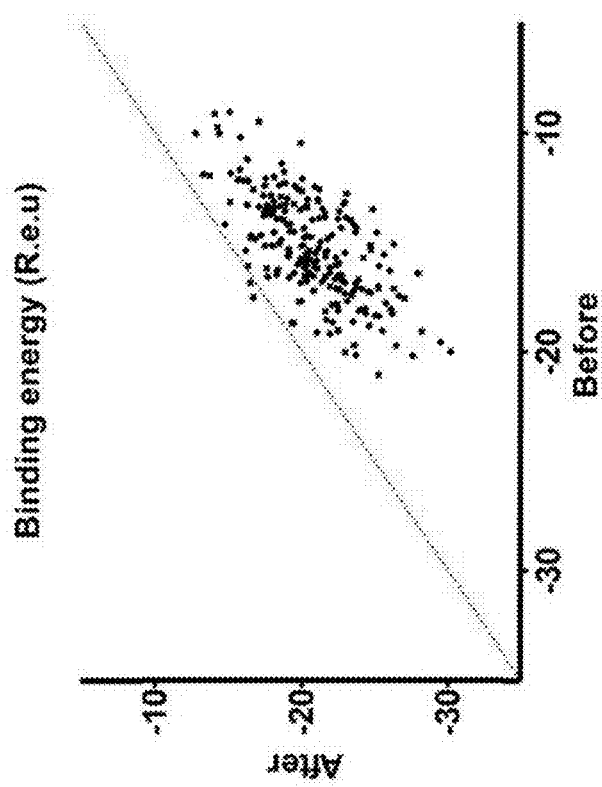
FIGS. 5A-B present scatter plots that compare between the stability (FIG. 5A) and binding energy (FIG. 5B) of the designed antibodies before and after refinement according to some embodiments of the method presented herein.
Figure 5A:
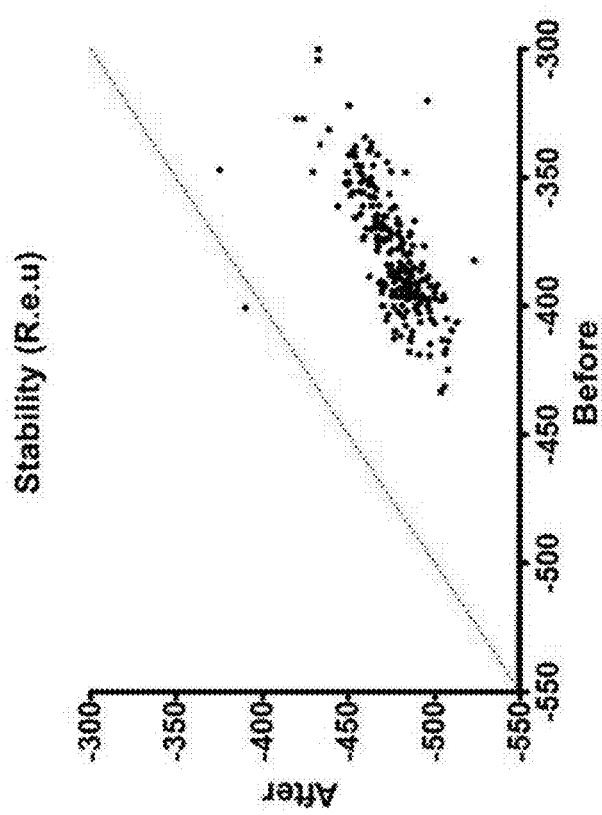

FIGS. 5A-B present scatter plots that compare between the stability (FIG. 5A) and binding energy (FIG. 5B) of the designed antibodies before and after refinement. The X-axis is calculated energy (R.e.u) of the antibody-target complex after sequence optimization and before refinement. Y-axis is the designed antibody energy (R.e.u) after the backbone refinement phase.

As can be seen in FIGS. 5A-B, rigid body, conformation and sequence refinement improves both binding energy and stability of the designed antibody. On average one observes an improvement of about 5 R.e.u (equivalent to approximately 2.5 kcal/mole) for binding energy and 100 R.e.u. (equivalent to approximately 50 kcal/mole) for antibody stability after the backbone refinement phase.

Filtering for Designs with Similar to Natural Binding Modes

In this step of the method presented herein, the final filtering of the designed antibody was carried out using four cutoff parameters corresponding to various parameters of the matching score, namely predicted binding energy, buried surface area, packing quality between the designed antibody's variable light and heavy domains and the bound ligand, and shape complementary between the antibody and bound ligand. As discussed hereinabove, cutoffs for each of these parameters was derived from experimental structure data of complexes of antibodies belonging to source antibody family, and the cutoffs for each of these parameters were derived from a set of 303 natural antibody-protein complexes listed below, which were extracted from the Protein Data Bank using the "SabDab" database. These same cutoff values were used in the exemplary benchmark recapitulation test presented below.

Designed antibodies with similar to natural binding modes were defined using the Critical Assessment of protein Structure Prediction (CASP) I_RMS criteria [Méndez, R. et al., *Proteins,* 2003, 52(1), p. 51-67]. Briefly, the designed antibody was structurally aligned to the natural antibody, targeting the same molecule. The root mean square deviation (RMSD) between the interface residues (all target residues within a 10 Å distance cutoff of the antibody structure) of the target in the designed complex was calculated relative to the natural complex. Designed antibody complexes with an I_RMS value of less than 4 Å were considered to have similar to natural binding modes.

The 303 PDB entries of natural antibody-protein complexes, which were used in setting the cutoff values for binding energy, buried surface area, packing quality and shape complementary are: PDB IDs 1A14, 1A2Y, 1AR1, 1BJ1, 1BVK, 1C08, 1CZ8, 1DQJ, 1EGJ, 1EO8, 1FDL, 1FE8, 1FJ1, 1FNS, 1G7H, 1G7I, 1G7J, 1G7L, 1G7M, 1G9M, 1G9N, 1GC1, 1H0D, 1IC4, 1IC5, 1IC7, 1IQD, 1J1O, 1J1P, 1J1X, 1JHL, 1JPS, 1JRH, 1K4C, 1K4D, 1KB5, 1KIP, 1KIQ, 1KIR, 1LK3, 1MHP, 1MLC, 1N8Z, 1NBY, 1NBZ, 1NCA, 1NCB, 1NCC, 1NCD, 1NDG, 1NDM, 1NFD, 1NMB, 1NMC, 1NSN, 1OAK, 1OB1, 1ORS, 1OSP, 1QFU, 1R0A, 1R3I, 1R3J, 1R3K, 1R3L, 1RJL, 1RZJ, 1RZK, 1S5H, 1TPX, 1TQB, 1TZH, 1TZI, 1UA6, 1UAC, 1UJ3, 1V7M, 1VFB, 1WEJ, 1XF5, 1XGP, 1XGQ, 1XGR, 1XGT, 1XGU, 1XIW, 1YJD, 1YQV, 1YYL, 1YYM, 1ZTX, 1ZWI, 2ADF, 2AEP, 2ARJ, 2ATK, 2B2X, 2BDN, 2BOB, 2CMR, 2DQC, 2DQD, 2DQE, 2DQF, 2DQG, 2DQH, 2DQI, 2DQJ, 2DWD, 2DWE, 2EIZ, 2EKS, 2FD6, 2FJG, 2H8P, 2H9G, 2HFE, 2HG5, 2HJF, 2HMI, 2HVJ, 2HVK, 2I5Y, 2I60, 2IFF, 2IH1, 2IH3, 2ITD, 2J88, 2JEL, 2JK5, 2NLJ, 2NR6, 2NXY, 2NXZ, 2NY0, 2NY1, 2NY2, 2NY3, 2NY4, 2NY5, 2NY6, 2NY7, 2NYY, 2OZ4, 2P7T, 2Q8A, 2Q8B, 2QQK, 2QQN, 2R0L, 2R56, 2UZI, 2VDK, 2VDL, 2VDM, 2VDO, 2VDP, 2VDQ, 2VDR, 2VXQ, 2VXT, 2WOF, 2W9E, 2WUC, 2XQY, 2XRA, 2XTJ, 2Y5T, 2YBR, 2YC1, 2YPV, 2YSS, 2ZCH, 3A67, 3A6B, 3A6C, 3B2U, 3B9K, 3BDY, 3BE1, 3BN9, 3BT2, 3CVH, 3D85, 3D9A, 3DET, 3DVG, 3DVN, 3EHB, 3EOA, 3FB5, 3GB7, 3GRW, 3HB3, 3HI1, 3HI6, 3IGA, 3IU3, 3JWD, 3K2U, 3KLH, 3KR3, 3L5W, 3L5X, 3L95, 3LD8, 3LDB, 3LEV, 3LH2, 3LHP, 3LIZ, 3MXW, 3NID, 3NIF, 3NIG, 3O2D, 3OR6, 3OR7, 3P0Y, 3PGF, 3PNW, 3Q3G, 3QWO, 3RKD, 3RVV, 3RVW, 3RVX, 3S35, 3S37, 3SDY, 3SE9, 3SKJ, 3SO3, 3SOB, 3SQO, 3STL, 3STZ, 3T3M, 3T3P, 3U30, 3U9P, 3UCO, 3V6O, 3VG9, 3VI3, 3VI4, 3VW3, 3W9E, 3WKM, 3ZDX, 3ZDY, 3ZDZ, 3ZE0, 3ZE2, 3ZKM, 3ZKN, 4AEI, 4AG4, 4AL8, 4ALA, 4CAD, 4D9Q, 4D9R, 4DGI, 4DKF, 4DN4, 4DTG, 4DVR, 4DW2, 4ENE, 4ETQ, 4F15, 4F37, 4F3F, 4FFV, 4FFW, 4FFY, 4G3Y, 4G6J, 4G6M, 4H88, 4HC1, 4HCR, 4HLZ, 4HT1, 4HWB, 4I2X, 4I9W, 4IRZ, 4JPK, 4JQI, 4JR9, 4JRE, 4K2U, 4K3J, 4K94, 4K9E, 4KI5, 4KJQ, 4KK8, 4KK9, 4KKL, 4L5F, 4LBE, 4LCU, 4LEO, 4LF3, 4LMQ, 4LOU, 4LSP, 4LSQ, 4LSR, 4M48, 4MSW and 4MWF.

FIGS. 6A-D present probability density plots showing the energy and structure criteria used to filter designed antibody structures in the final steps of the method presented herein, when demonstrated for Fv domains of antibodies, wherein the designed antibodies were filtered based to four parameters: predicted binding energy (FIG. 6A), buried surface area (FIG. 6B), shape complementarity between antibody structure and ligand (FIG. 6C), and packing quality between the variable light and heavy domain domains and the ligand (FIG. 6D), whereas the cutoff values are represented by dashed lines and derived from a set of 303 natural protein binding antibodies, while antibody designs (black curve) that passed all filters are compared with the natural protein-binding antibodies (gray curve).

Use of the Algorithm AbPredict for Blind Prediction of Antibody Structures from Sequence:

To validate the stability of designed antibodies sequence design can be disabled in optimize_chimera.xml and the MCSA protocol be employed that samples from the different structural segments and rigid body orientations. For a benchmark against experimental structures, it has been observed that the native structure is well separated from alternative conformations with an energy gap of around 8 Rosetta Energy Unit (data not shown). When such energy gaps are observed predict and design become feasible [Fleishman, S. et al., *Cell*, 2012, 149(2), pp. 262-273].

Example 2

Designed Antibody—A Recapitulation Benchmark

To test the ability of the method, according to some embodiments of the present invention, to predict the structures and sequences of protein-binding antibodies, a diverse benchmark of nine high-affinity (Kd<10 nM), high-resolution (X-ray resolution <2.5 Å), protein-binding antibodies were selected using the Structural Antibody Database "SAbDab" (see, Table 5 below).

The natural antibody set comprises human antibodies Fab40,D5 neutralizing mAb, and BO2C11 (PDB IDs 3K2U, 2CMR and 1IQD respectively), murine antibodies E8, D1.3 mAb, F10.6.6, JEL42, and 5E1 Fab (PDB IDs 1WEJ, 1VFB, 1P2C, 2JEL and 3MXW respectively), and the humanized murine antibody D3H44 (PDB ID 1JPS). The target molecule comprise convex (2JEL, 1IQD), flat (1P2C), and concave (3MXW) surfaces, containing helical (2CMR), sheet (1JPS), and loop (1P2C, 3K2U) secondary-structural elements.

The benchmark recapitulation test has started from the set of 4,500 computationally reconstituted and designed antibody structures. Each structure was aligned to the position of the natural binding antibody in its bound conformation and a complex structure comprising the designed structure and the molecular entity comprising the surface of interest was generated. All sequence and backbone conformation information from the natural antibody was eliminated. A reduced representation docking was applied (see description hereinabove) using RosettaDock to perturb the initial binding mode between the antibody and the target.

To test the method's performance the designed antibodies with the highest computed binding affinity for each antibody-target complex in the benchmark set were isolated, and this design was contrasted with the natural antibody according to the following parameters: sequence identity, RMSD, interface shape complementarity (Sc), packing statistics, buried surface area, binding energy, and backbone conformation clustering.

Table 5 presents bound antibody complexes used for recapitulation benchmark and summarized the results of the benchmark recapitulation test experiment.

TABLE 5

| PDB IDs | Binding surface area (Å)[a] | Packing[b] | Shape complementary[c] | Predicted binding energy (R.e.u) | Target | $K_d^d$ (nM) | Predicted binding energy rank[e] | Predicted binding energy (R.e.u) | Buried surface area (Å²) | Antibody backbone RMSD (Å)[h] | Target interface RMSD (Å)[h] |
|---|---|---|---|---|---|---|---|---|---|---|---|
| 1JPS | 1950 | 0.66 | 0.70 | −25 | Tissue factor | 0.1 | 1/1809 | −38.8 | 2063 | 1.23 | 2.20 |
| 1WEJ | 1220 | 0.70 | 0.75 | −16 | Cytochrome C | 15.8 | 3/93 | −24.5 | 1535 | 1.51 | 2.00 |
| 2CMR | 2110 | 0.58 | 0.72 | −22 | Transmembrane glycoprotein | 0.005 | 11/297 | −26.3 | 2162 | 1.15 | 1.40 |
| 3MXW | 1882 | 0.70 | 0.51 | −21 | Sonic hedgehog protein | 0.7 | 24/1274 | −32.2 | 2011 | 1.52 | 2.72 |
| 1VFB | 1405 | 0.67 | 0.69 | −22 | Lysozyme | 3.7 | 24/250 | −24.3 | 1493 | 1.15 | 3.20 |
| 2JEL | 1549 | 0.66 | 0.58 | −17 | Phosphocarrier protein HPr | 3.7 | 9/50 | −20.4 | 1353 | 1.30 | 2.70 |
| 3K2U | 1982 | 0.62 | 0.68 | −29.2 | Hepatocyte growth factor activator | 0.16 | 51/112 | −26.6 | 1695 | 1.31 | 3.20 |
| 1P2C | 1467 | 0.68 | 0.67 | −17 | Lysozyme | 0.0098 | 138/659 | −22.2 | 1566 | 1.30 | 3.90 |
| 1IQD | 2134 | 0.70 | 0.78 | −32 | Coagulation factor VIII | 0.0014 | 762/2802 | −24.7 | 1632 | 1.24 | 2.80 |

| PDB IDs | Packing score[b] | Shape complementary[c] | Same as natural segment[i] | | | | Overall sequence identity (%) | Interface sequence identity (%)[j] | CDR sequence identity (%)[k] | | Core sequence identity (%)[l] |
| | | | VL | L3 | VH | H3 | | | VH | VL | |
|---|---|---|---|---|---|---|---|---|---|---|---|
| 1JPS | 0.66 | 0.62 | v | v | v | v | 68 | 31 | 67 | 54 | 89 |
| 1WEJ | 0.67 | 0.62 | v | v | v | 0 | 64 | 37 | 61 | 43 | 82 |
| 2CMR | 0.57 | 0.60 | v | v | v | v | 64 | 26 | 61 | 68 | 75 |
| 3MXW | 0.69 | 0.58 | v | v | v | v | 58 | 53 | 42 | 54 | 60 |
| 1VFB | 0.64 | 0.60 | v | v | v | v | 63 | 27 | 60 | 56 | 80 |
| 2JEL | 0.62 | 0.60 | v | v | v | −1 | 68 | 13 | 71 | 80 | 77 |

TABLE 5-continued

| | | | | | | | | | | | |
|---|---|---|---|---|---|---|---|---|---|---|---|
| 3K2U | 0.58 | 0.62 | v | v | v | −1 | | 70 | 40 | 62 | 86 | 77 |
| 1P2C | 0.68 | 0.60 | v | v | −1 | 1 | | 52 | 34 | 52 | 59 | 64 |
| 1IQD | 0.66 | 0.67 | v | v | v | v | | 62 | 26 | 66 | 60 | 71 |

[a]Binding surface area is the area excluded from water upon target binding.
[b]A criterion that measures how well the antibody core and the binding surface are packed
[c]Shape complementarity between the binding surface of the antibody and target
[d]Kd values of the natural antibody taken from the "SabDab" database.
[e]All designed antibodies that are within a 4 Å distance of the target epitope are included in the ranking.
[f]Similar conformations are all designed antibodies that are comprised of segments of the same conformational clusters as the natural antibody
[g]RMSD was calculated over all Cα atoms
[h]Target interface is calculated over all target Cα atoms within a 10 Å radius of the antibody.
[i]A "v" signifies that design has a segment from the same conformational cluster as the natural antibody. If not, the number states the amino acid length change in the design segment relative to the natural antibody.
[j]Interface residues are all antibody residues within a 10 A distance of the target
[k]CDR residues do not include interface residues
[l]Core residues are all the antibody residues that are not part of the CDR and are not solvent exposed As can be seen in Table 5, the design method presented herein does not exclusively produce the natural binding mode observed in the PDB. To analyze the designed conformations and sequences in the experimentally observed binding mode, the bound conformations where the target interface is more than 4 Å RMSD were eliminate from the natural conformation.

As can further be seen in Table 5, the design method presented herein recapitulated the natural antibody conformation with high probability. Five of the nine antibodies in the benchmark set were at the top 10% ranking in terms of computed binding energy. Bound conformations with large buried surface area (more than 1800 Å$^2$) were predicted correctly more consistently than those with lower buried surface area.

As a representative example for a successfully recapitulated binding mode, designs that target the same surface as the humanized anti-tissue factor antibody D3H44 (PDB ID 1JPS) and the anti-transmembrane glycoprotein D5 neutralizing mAb (PDB ID 2CMR) were considered. All backbone conformation segments comprising the designed antibody belong to the same backbone clusters as the experimentally determined structure of 1JPS (L1.11_L2.8, L3.10.1, H1.14_H2.15, H3.16.5) and 2CMR (H1.14_H2.15, H3.18.7, L1.11_L2.8, L3.10.1). The backbone conformations and binding modes of these designs show a high level of agreement with the natural antibodies.

Cases where designs with similar conformations to the natural antibody have a poor predicted binding energy ranking highlight potential biases in the design method. In the case of the anti-lysozyme antibody F10.6.6 (PDB ID 1P2C) the natural antibody buries a relatively small surface area (see, Table 5). Most of the top ranked designs that target the same lysozyme epitope bury larger surfaces (more than 1600 Å$^2$) by using longer L1 segments. Longer segments that bury larger surfaces and maintain high complementarity for the target were preferentially chosen by the filtering procedure; experiments were required to demonstrate whether such designs indeed have higher affinity for their target then the natural antibody. The anti-hepatocyte growth factor activator antibody (PDB ID 3K2U) has a binding surface area of 1980 Å$^2$, while the best-ranked similar-conformation design buries only 1700 Å$^2$ (see, Table 5). This difference in buried surface area is due to a difference in the packing angle between the light and heavy variable domains of the natural and designed antibodies; more extensive modeling of the packing angle between the variable domains can be carried out in order to address such inaccuracies.

The sequence-recapitulation rates were in the range of previously described design benchmarks. The values were not directly comparable, however, since previously described attempts at design work dealt with either functional-site design or the protein core, whereas the antibody-design benchmark presented herein deals with both, and since in the method presented herein is carried out while constraining sequence variations and conformation choices based on experimental data. Sequence within the antibody core was recapitulated to within roughly 60-80% identity, as in previously described benchmark studies, and the binding surface sequence identity was about 30%, similar to protein-binding, and enzyme-design benchmarks.

Two prominent examples of the high recapitulation of the natural interaction were the anti-tissue factor designed antibody and the anti-transmembrane glycoprotein designed antibody. In both cases the interface-sequence recapitulation was above 30% (see, Table 5), and conserved residues at the interface also conserves the side chain conformations. As observed for natural antibodies, most sequence variation in the set of designed antibodies was restricted to the target binding surface; antibody core positions were considerably more conserved. This high sequence conservation is also reflected in high recapitulation of the side-chain conformations in the antibody core.

Since amino acid conformational plasticity has the potential to reduce binding specificity and affinity, design algorithms that rigidify side-chains at the binding surface are generally successful in designing protein inhibitors and protein and small-molecule binders. A computational metric to assess side-chain rigidity was suggested which computes the Boltzmann weight of the bound side-chain conformation in the ensemble of all side-chain conformations when the binder is dissociated from its target. Designed binders using existing strategies typically show lower side-chain Boltzmann weights, and presumably lower rigidity, than natural binders. Previous design attempts, which have incorporated side-chain rigidity into their design scheme, have either explicitly accounted for it during design or have used it as an additional filter for design evaluation. It is hypothesized that the sequence-structure rules encoded in the backbone-conformation library and the related PSSMs implicitly constrain residues in the designed antibody binding surfaces to more rigid choices. A comparison of the side-chain conformational plasticity at the binding surfaces of 303 natural high-affinity antibodies with the presently designed antibodies using the method described herein, show that designed aromatic residues at the binding surface, which contribute more than 1 R.e.u to the predicted binding energy, exhibited conformation-probability densities very close to natural antibodies. The proportion of very-low probability side-chain conformations (less than 5% probability), which were unlikely to be in their intended conformation in the unbound state, is less than 10%, and more than half of all designed antibodies' interface residues exhibited side-chain conformations with probabilities above 15%.

Example 3

Expression of De-Novo Designed Antibody

By use of the method described herein, thousands of protein sequences were obtained, out of which 19 have been chosen for experimental expression and activity testing. The amino acid sequences were transcribed into DNA as single-chain variable fragments with GS-linkers connecting the C-terminus of the $V_H$ chain to the N-terminus of the $V_L$ chain, codon optimized for expression in the baker's yeast *S. cerevisiae*. After external custom synthesis, the DNA segments with upstream and downstream flanking regions were amplified by PCR and inserted into the pETCON plasmid by homologous recombination in *S. cerevisiae* strain EBY100. The obtained plasmid was verified by sequencing and used for testing in yeast-surface display, where expression is monitored by fluorescent staining of the designed antibody while ligand recognition was monitored by fluorescent labeling of the biotinylated ligand.

The relatively low affinity of the initial designs was then enhanced by in-vitro evolution; the original design was amplified by error-prone PCR under conditions to yield 1-3 mutations per gene, and a yeast library (in *S. cerevisiae* strain EBY100) generated from the resulting DNA. By several rounds of FACS sorting, clones with increased affinity were isolated and, if necessary, the process was repeated.

According to embodiments of the present invention, designed proteins that exhibit expression levels of 75% and above were obtained. These rates were formerly not achieved by presently known computational design methods, and were comparable to the expression level of the anti-fluorescein antibody 4m5.3, which served as a template in the design process as well as a gold standard for high expression and stability as an scFv in yeast surface display.

In addition, the method presented herein yielded antibody structures that recognized the target they were designed to bind at notably higher affinity compared to the affinity afforded by random antibody structures.

FIG. 7 presents a scatter plot of yeast surface display with cells stained for expression levels and binding for testing two antibodies, "Design #1" (SEQ ID NO. 1), designed using the herein described algorithm, to bind ACP (marked by gray dots) and an anti-tissue-factor antibody "4m5.3" that does not bind ACP (marked by black dots) that served as the template structure and as the control in the binding test to demonstrate that the binding between ACP and Design #1 (SEQ ID NO. 1) is specific, wherein expression levels are characterized by a left shift on the X-axis, and binding is characterized by an upward shift on the Y-axis.

As can be seen in FIG. 7, the cells expressing anti-ACP Design #1 (SEQ ID NO. 1) exhibit stronger binding to 10 µM ACP than the control 4m5.3 as can be derived from the y-shift of this population. The binder subsequently underwent in-vitro evolution which lead to identification of clones with single amino-acid substitutions that increase affinity.

FIGS. 8A-B present titration curves of anti-ACP design before and after introduction of point mutations (Design #1-5; SEQ ID NOs. 1-5, FIG. 8A) and the titration curves of anti-ACP design (Design #1 SEQ ID NO. 1) with its designed substrate ACP (marked by circles in FIG. 8B) and negative controls (TEM, marked by squares in FIG. 8B).

Point mutations were introduced to the binding interface of Design #1 (SEQ ID NO. 1) according to the model generated using the described algorithm. These mutations were predicted to be detrimental to the binding. Two separate point mutations were introduced: A34N (Design #2; SEQ ID NO. 2) and S100W (Design #3; SEQ ID NO. 3) as well as complete segment changes, introducing loops H2 and H3, separately, from an anti-fluorescein antibody (4m5.3) that does not bind ACP (Design #4 (SEQ ID NO. 4) and Design #5 (SEQ ID NO. 5), respectively).

As can be seen in FIGS. 8 A-B, a second binder for ACP has been generated with the presented algorithm with an initial estimated kD of 885 nM, which could be increased by in-vitro evolution to 45 nM. As can further be seen in FIGS. 8 A-B, the introduction of a single amino acid and loop exchanges which are predicted to disturb binding were shown to drastically reduce binding.

As can also be seen in FIG. 8A, all changes to the binding interface of Design #1 (SEQ ID NO. 1) abolish binding to ACP, thereby supporting the modeled interaction between Design #1 (SEQ ID NO. 1) and ACP. To demonstrate that Design #1 (SEQ ID NO. 1) specifically binds ACP and is not promiscuous ("sticky") binding against another substrate (TEM) was tested and exhibited no binding (FIG. 8B).

Example 4

Modifying the Specificity of a Phosphotriesterase (PTE) Enzyme

The method described herein was used to generate a model of the active site of a phosphotriesterase (PTE), a bi-nuclear metal dependent enzyme belonging to the common protein fold of TIM-barrels. PTE's can hydrolyze paraoxon, a widely used pesticide, at diffusion limit. It has been hypothesized the PTE's have evolved from another TIM-barrel fold enzyme that hydrolyzes lactone [Afriat-Jurnou, L. et al., *Biochemistry*, 2012, 51, 6047-6055]. Although PTE cannot hydrolyze lactone, lactonases are known to exhibit promiscuous PTE activity [Hiblot, J., *Sci. Rep.*, 2012, 2, p. 779]. It was hypothezied that PTE cannot hydrolyze lactone due to a clash between the lactone acyl chain and loop 7 of the enzyme.

The method presented herein has been used to generate a phosphotriesterase TIM-barrel with a modified conformation of blade 7 while preserving all other parts of the structure conformationally unchanged. Parathion hydrolase from *Pseudomonas diminuta* (PDB ID: 1HZY) was used as the template protein. The stem residues (locations of highest structural conservation) for blade 7 are 216 and 263 (numbering according to PDB structure).

One hundred seventy seven (177) possible conformation variants were generated, of which nine (9) were selected for experimental testing after visual inspection using Pymol and addition of mutations manually, mainly to increase protein packing using Foldit [Khatib, F. et al., *Proc. Natl. Acad. Sci.*, 2011, 108, pp. 18949-18953]. Since all designed structures share the same N-terminus region (amino acid residues 1-196) the N-terminal gene and the variable C-termini regions were ordered separately and combined them using PCR. All designs were fused with N-terminal MBP to aid in cleaning and stability of the proteins and expressed in *E. coli* BL21 cells with no chaperones.

Out of the nine designed structures, two were expressed at wild type levels, as seen in Polyacrylamide gel electrophoresis (data not shown). For the two well-expressed designs, Design #6 (SEQ ID NO. 6) possesses a blade 7 conformation derived from *Geobacillus kaustophilus* lactonase (PDB ID: 4HA0) and Design #7 (SEQ ID NO. 7) possesses a blade conformation derived from *Listeria monocytogenes* lactonase (PDB ID: 3PNZ). Both designs displayed PTE activity with paraoxon above background but no detectable lactonase activity, as tested with thio-alkyl butyrolactone substrate (TBBL) substrate. Inspection of the designs revealed that at position 220 there should be an arginine that has previously been reported to be important for lactonase activity. An arginine residue was reintroduced at position 220 in both designs, and both revised designs displayed similar expression level as before.

After the mutation, Design #6 (SEQ ID NO. 6) exhibited lactonase activity as well as paraoxon activity. Design #6 displayed altered substrate specificity; the original template (Parathion hydrolase from *Pseudomonas diminuta*) has a TBBL/paraoxon ratio of about 3×10−5 while Design #6 (SEQ ID NO. 6) has a TBBL/paraoxon ratio of 0.15 which is a $10^3$ fold change. While Design #7 (SEQ ID NO. 7) displayed no detectable activity with paraoxon or the other tested lactone substrates.

Example 5

Modifying the Specificity of a Lactonase Enzyme

In order to further demonstrate that the method can afford complete control over the enzyme specificity using backbone design, the method was used to alter the substrate specificity of a lactonase enzyme. A hyper thermostable lactonase from *Sulfolobus solfataricus* (PDB ID: 2VC7) was chosen as a template structure. The template structure has moderate $K_{cat}/K_m$ efficiency towards paraoxon (see, Table 6 above). Generating the designed conformations was similar to the method described above for phosphotriesterase expect for two differences: (i) four blades (blades 4-7) were altered during backbone design, while blades 1, 2, 3 and 8 form a part of the dimerization interface and therefore were kept unaltered, and (ii) the conformations of blade 7 were limited to those derived from known PTE's.

The original docked orientation of paraoxon was generated by aligning the crystal structures of a PTE bound to a paraoxon analog (PDB ID: 2R1N) to the crystal structure of the template protein and copying the ligand coordinates to the template protein structure.

Five designed structures with different blade 7 conformation and sequence design choices were chosen for experimental testing (SEQ ID NOs. 8-12).

Figure 9:
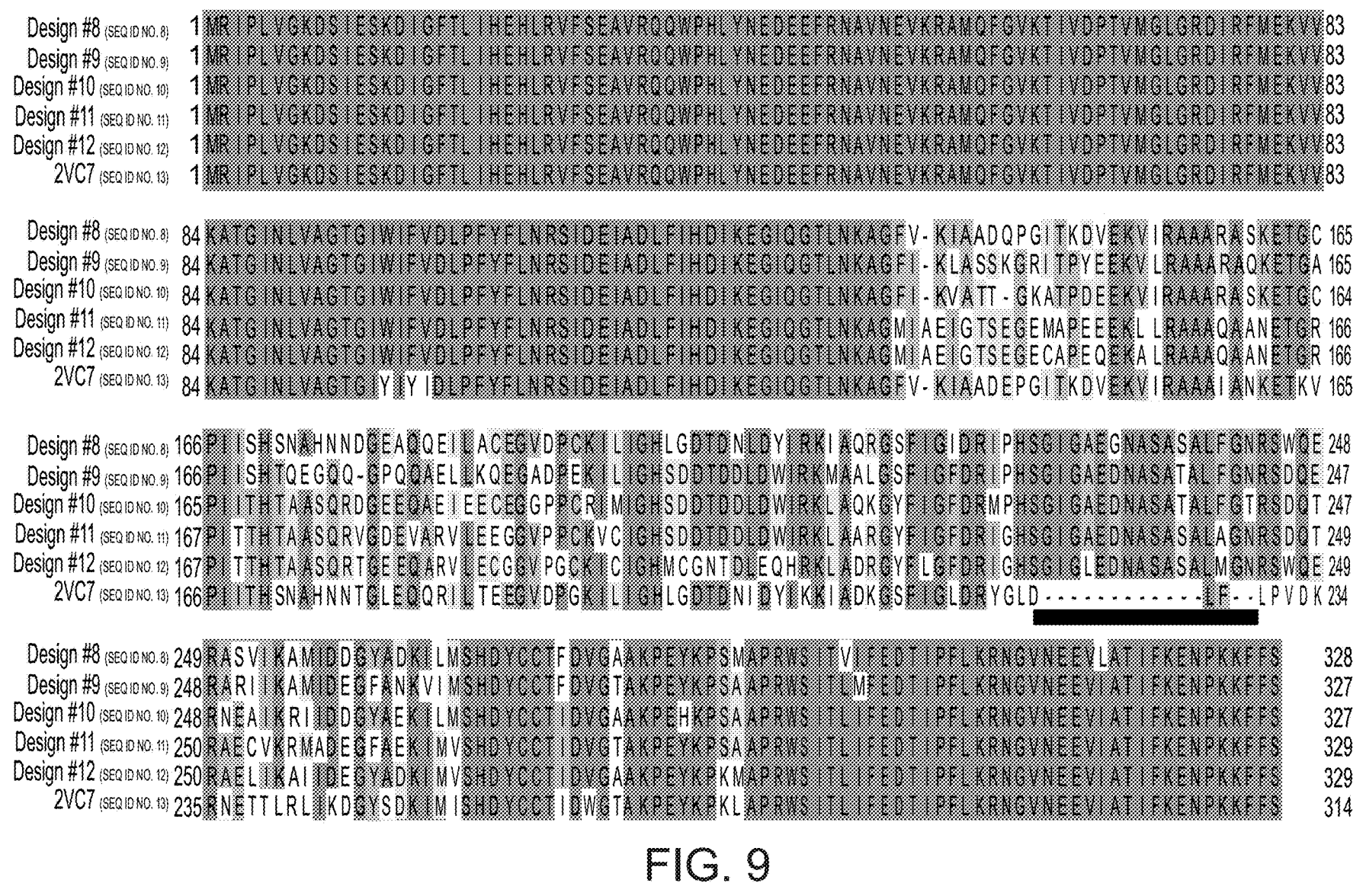

FIG. 9 presents sequence alignment of the five TIM-barrel fold designs denoted Design #8-12 (SEQ ID NOs. 8-12 respectively), with designed altered substrate specificity, compared with the sequence of the original enzyme which served as the design template (lactonase from *Sulfolobus solfataricus*; PDB ID: 2VC7; SEQ ID NO. 13).

As can be seen in FIG. 9, fourteen amino acids were inserted to the template protein and that additional sequence modifications were introduced around the inserted segment (marked with a bold line) to accommodate the insertion. Previous attempts to introduce insertions from other members in the PTE family have resulted in nonfunctional proteins [Afriat-Jurnou, L. et al., *Biochemistry*, 2012, 51, 6047-6055].

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of producing a designed protein having a desired affinity to a molecular surface of interest, the method comprising:

(i) providing a plurality of source polypeptide structures having a common structural fold, said common structural fold having conserved structural regions and diverse structural regions, said conserved structural regions having locations of highest structural conservation, said locations are backbone atoms positions that are identified by aligning said plurality of source polypeptide structures, and defining Cα atoms having relatively small root mean squared deviation (RMSD) value within each of said conserved structural regions as said locations;

(ii) segmenting each of said plurality of source polypeptide into structurally homologous segments, each of said segments is a continuous section of a backbone of any one of said source polypeptide structures, which starts at one location of highest structural conservation and ends at a consecutive location of highest structural conservation and having a diverse structural region between said consecutive locations, thereby obtaining a plurality of groups of structurally homologous segments, each said groups being defined by said two consecutive locations;

(iii) arbitrarily selecting a template structure from said plurality of source polypeptide structures;

for each of said groups:

(iv) splitting at least one segment at a randomly selected position in said diverse structural region between and several positions away from said two consecutive locations so as to obtain a split segment;

(v) superimposing respective positions in each of two sub-segments of said split segment onto corresponding positions in said template structure, and grafting each of said two sub-segments on said specific positions, thereby displacing a corresponding segment in said template structure with said two sub-segments of said split segment;

(vi) subjecting said template structure having said split segment to computational structure refinement in order to achieve segment closure, thereby obtaining a reclosed segment in said template structure, wherein said computational structure refinement comprises at least one operation selected from the group consisting of geometrical optimization, spatial optimization, energy optimization, modulation of backbone dihedral angles, atomic positions, amino acid side-chain packing and PSSM-derived constrained change of amino acids;

(vii) optionally repeating steps (iv)-(vi), while splitting at a different site or aborting further manipulation of said structurally homologous segment;

(viii) repeating steps (iv)-(vii) for at least one additional structurally homologous segment, so as to obtain at least one additional reclosed segment corresponding to each of said groups;

optionally sorting each said reclosed segment corresponding to each of said groups into at least one structural cluster, and selecting a representative reclosed segment for said structural cluster, whereby each said reclosed segment of step (ix) is said representative reclosed segment;

(ix) using said reclosed segments corresponding to each of said groups for reconstructing a plurality of reconstructed structures, each of said reconstructed structures having the common structural fold having conserved structural regions defining said structural framework and said diverse structural regions and positions corresponding to said locations of highest structural conservation;

(x) matching at least one of said reconstructed structures onto the molecular surface of interest, so as to design a plurality of reconstructed structures-molecular surface complexes each having a matching score, and optionally repeating step (x) for said reconstructed structure in said complex, wherein said matching comprises at least one operation selected from the group consisting of rigid body orientation, modulation of backbone dihedral angles, amino acid side-chain packing and change of amino acids, and wherein said matching score comprises at least one an attribute selected from the group consisting of buried surface area, shape complementary, binding energy (affinity), and any combination thereof;

(xi) optionally substituting at least one of said segment in said reconstructed structure of at least one of said complexes with another corresponding reclosed segment and repeating step (x) so as to design a substituted-reconstructed structure-molecular surface complex having a matching score; and (xii) based on said matching score, selecting the amino-acid sequence having the desired affinity to the molecular surface of interest of the molecular entity;

expressing the amino-acid sequence in an expression system;

thereby producing the amino-acid sequence having the desired affinity to the molecular surface of interest.

2. The method of claim 1, further comprising:

defining in said plurality of source structures terminal segments, each of said terminal segments being defined by one location of said locations of highest structural conservation and a terminal location of the common structural fold, so as to define said terminal segments; and regarding at least one of said terminal segments as a split segment in step (v).

3. The method of claim 1, wherein said sorting is conducted by a segment length.

4. The method of claim 3, wherein said sorting is further conducted by a root mean squared deviation of aligned polypeptide backbone positions.

5. The method of claim 1, wherein said change of amino acids is effected for amino acids of said split segment, and for amino acids in said template structure being at least partly inside a shell surrounding said split segment.

6. The method of claim 5, wherein said change of amino acids is dictated by rules, said rules comprise a position-specific scoring matrix.

7. The method of claim 1, wherein said change of amino acids is effected for amino acids of said another corresponding fitted reclosed segment, and for amino acids in said template structure being at least partly inside a shell surrounding said another corresponding fitted reclosed segment.

8. The method of claim 7, wherein said change of amino acids is dictated by rules, said rules comprise a position-specific scoring matrix.

* * * * *